United States Patent [19]

Kawamoto et al.

[11] Patent Number: 5,104,867
[45] Date of Patent: Apr. 14, 1992

[54] 2-(HETEROCYCLYLTHIO)CARBAPENEM DERIVATIVES, THEIR PREPARATION AND THEIR USE AS ANTIBIOTICS

[75] Inventors: Isao Kawamoto; Teruo Tanaka; Rokuro Endo; Masayuki Iwata; Masao Miyauchi, all of Hiromachi, Japan

[73] Assignee: Sankyo Company, Limited, Tokyo, Japan

[21] Appl. No.: 540,878

[22] Filed: Jun. 20, 1990

Related U.S. Application Data

[63] Continuation of Ser. No. 332,884. Apr. 3, 1989, abandoned.

[30] Foreign Application Priority Data

Apr. 1, 1988 [JP] Japan .................. 63-80974
May 10, 1988 [JP] Japan .................. 63-111640

[51] Int. Cl.$^5$ .................. C07D 487/04; A61K 31/40
[52] U.S. Cl. .................. 514/210; 540/350
[58] Field of Search .................. 540/350; 514/210

[56] References Cited

U.S. PATENT DOCUMENTS

| | | | |
|---|---|---|---|
| 4,460,799 | 7/1984 | Perrin et al. | 540/350 |
| 4,552,873 | 11/1985 | Miyadera et al. | 540/350 |
| 4,613,595 | 9/1986 | Miyadera et al. | 540/350 |
| 4,640,799 | 2/1987 | Kim et al. | 540/350 |
| 4,665,170 | 5/1987 | Kim et al. | 540/350 |

FOREIGN PATENT DOCUMENTS

| | | | |
|---|---|---|---|
| 0017992 | 10/1980 | European Pat. Off. | |
| 0126587 | 11/1984 | European Pat. Off. | |
| 160391 | 11/1985 | European Pat. Off. | 514/210 |
| 0167139 | 1/1986 | European Pat. Off. | |
| 0235823 | 9/1987 | European Pat. Off. | |

*Primary Examiner*—Robert Gerstl
*Attorney, Agent, or Firm*—Frishauf, Holtz, Goodman & Woodward

[57] ABSTRACT

Compounds of formula (I):

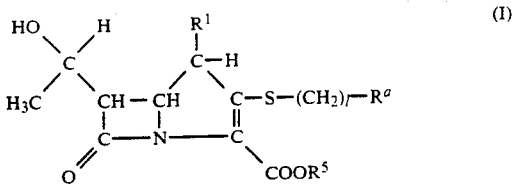

in which $R^a$ is a group of formula (II):

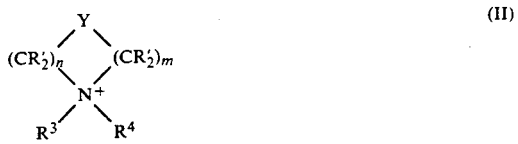

or a group of formula (III):

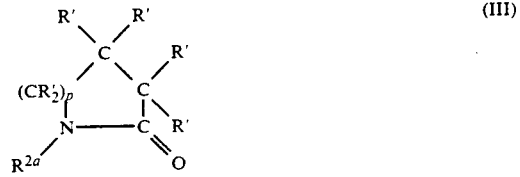

(where one of R' is a bond to the remainder of the compound, one more of R' is $R^2$ and the others of R' are all hydrogen), $R^1$ is hydrogen or methyl, $R^2$ is hydrogen, optionally substituted alkyl, halogen, hydroxy, alkoxy, amino, alkanoylamino, alkanoyloxy, alkanoyl, carboxy, alkoxycarbonyl, cyano, —S(O)$_j$R$^9$ (where j is 0, 1 or 2 and $R^9$ is alkyl), or —CONR$^6$R$^7$ (which is optionally substituted carbamoyl or heterocyclyl-carbonyl), $R^{2a}$ is hydrogen, alkyl or alkanoyl, —NR$^3$R$^4$ is optionally substituted amino or heterocyclic, and —COOR$^5$ is carboxy, —COO$^-$, —COOM$_x$ (where M is a cation and x is the reciprocal of the valence of the cation M) or protected carboxy and, where —COOR$^5$ is carboxy, —COOM$_x$ or protected carboxy, the compound of formula (I) also contains an anion; l, m and n are independently 0, 1, 2 or 3, provided that (m+n) is an integer from 2 to 6; p is 0, 1 or 2; Y is a single bond, oxygen, sulfur or $R^8$N< (wherein $R^8$ is hydrogen, alkyl or alkanoyl) and pharmaceutically acceptable salts and esters thereof are potentially valuable antibiotics.

28 Claims, No Drawings

2-(HETEROCYCLYLTHIO)CARBAPENEM DERIVATIVES, THEIR PREPARATION AND THEIR USE AS ANTIBIOTICS

This application is a continuation of application Ser. No. 332,884, filed Apr. 3, 1989, now abandoned.

BACKGROUND OF THE INVENTION

1. Field of the Invention

The present invention relates to a series of new carbapenem compounds, to methods using these compounds and to compositions containing these compounds, and provides processes for preparing these compounds.

2. Background and Information

The penicillins form a well known class of antibiotics, which have found considerable use in human and animal therapy for many years. Chemically, the penicillins have in common a β-lactam structure, commonly referred to as "penam", which may be represented by the following formula:

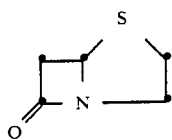

(A)

However, although the penicillins still form a valuable weapon in the pharmaceutical armory, the development of new, and often penicillin-resistant, strains of pathogenic bacteria has increasingly made it necessary to search for new types of antibiotic.

In recent years, great interest has been shown in compounds having a carbapenem structure, that is compounds having a carbon atom in place of the sulfur atom at the 1-position and having a double bond between the carbon atoms in the 2- and 3-positions of the basic penam structure. The carbapenem structure may be represented by the following formula:

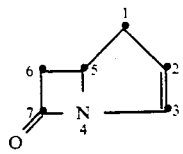

(B)

These penam and carbapenem structures form the basis for the semi-systematic nomenclature of the penicillin derivatives in accordance with the recommendations of the International Union of Pure and Applied Chemistry (IUPAC), and this nomenclature is generally accepted by those skilled in the art throughout the world and is used herein. The numbering system employed herein is that illustrated on the above formula (B).

Of the known carbapenem derivatives, the best known is a compound called "thienamycin", whose semi-systematic name is 2-(2-aminoethylthio)-6-(1-hydroxyethyl)carbapen-2-em-3-carboxylic acid. Although thienamycin is known to have remarkably potent and broad antibacterial activity, its chemical stability in the human body is poor, which restricts its practical use. Various attempts have, therefore, been made to modify the chemical structure of thienamycin in order to improve its chemical stability whilst maintaining or improving its superior activity, but there is still a continuing need to develop further carbapenem antibiotics with improved properties.

The present invention provides a new group of carbapenem derivatives which possess superior absorption and metabolic stability (as evidenced by improved recovery rates in the urine), as well as a broad antibacterial spectrum and low toxicity. The invention also provides synthetic processes for the preparation of the new carbapenem derivatives, as well as pharmaceutical compositions comprising the said derivatives suitable for human and animal administration.

Of the prior art known to us, the following are believed to be the closest:

U.S. Pat. No. 4,640,799 and U.S. Pat. No. 4,665,170 disclose carbapenem compounds in which there is a group —S—A—N at the 2-position. "A" can be various groups, and N represents a quaternized nitrogen-containing heterocyclic group attached to A through its quaternary nitrogen atom. These compounds differ from those of the present invention in that, where the compounds of the present invention contain a quaternized nitrogen-containing heterocyclic group having a quaternary nitrogen atom, this is not attached to the rest of the molecule via the quaternary nitrogen atom, but is attached via a carbon atom of the heterocyclic group.

European patent Specification No. 126 587 discloses a series of carbapenem compounds having a pyrrolidinylthio group at the 2-position. These differ from the compounds of the present invention which are quaternary nitrogen compounds in that these prior art compounds are not quaternary nitrogen compounds and they differ from the non-quaternized compounds of the present invention in the nature of the substituents on the heterocyclic ring. Certain of the compounds disclosed in this prior art may have good activity, but they are believed to be less well absorbed in vivo than are the compounds of the present invention.

BRIEF SUMMARY OF INVENTION

The compounds of the present invention may be represented by the formula (I):

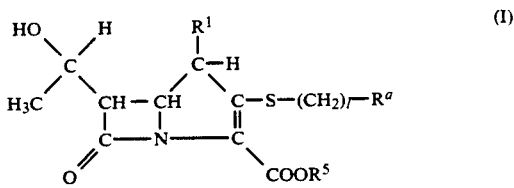

(I)

in which:

$R^a$ represents a group of formula (II):

(II)

or a group of formula (III):

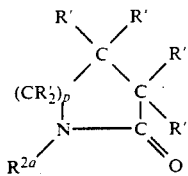

(III)

and in which:
one of the symbols R' represents a bond to the remainder of the compound of formula (I), in said group of formula (II) one of the symbols R' is $R^2$ and in both said groups of formula (II) and (III) the others of the symbols R' all represent hydrogen atoms;
where $R^a$ represents said group of formula (II), then $R^1$ represents a hydrogen atom or a methyl group, or, where $R^a$ represents said group of formula (III), then $R^1$ represents a methyl group;
$R^2$ represents a hydrogen atom, a $C_1-C_6$ alkyl group, a $C_1-C_6$ alkyl group having at least one substituent selected from the group consisting of substituents (a), a halogen atom, a hydroxy group, a $C_1-C_6$ alkoxy group, an amino group, a $C_1-C_6$ alkanoylamino group, a $C_1-C_6$ alkanoyloxy group, a $C_1-C_6$ alkanoyl group, a carboxy group, a $C_2-C_7$ alkoxycarbonyl group, a cyano group, a group of formula $-S(O)_iR^9$
  wherein i is zero or an integer 1 or 2 and $R^9$ represents a $C_1-C_6$ alkyl group;
or a group of formula $-CONR^6R^7$
  wherein $R^6$ and $R^7$ are independently selected from the group consisting of hydrogen atoms, $C_1-C_6$ alkyl groups, $C_3-C_6$ cycloalkyl groups, $C_2-C_6$ alkenyl groups, $C_2-C_6$ alkynyl groups and $C_1-C_6$ alkyl groups having at least one substituent selected from the group consisting of substituents (a), or $R^6$ and $R^7$ together represent a $C_1-C_6$ alkylene group or a $C_1-C_6$ alkylene group whose carbon chain is interrupted by an oxygen or sulfur atom or by a group of formula $R^8N<$.
    wherein $R^8$ represents a hydrogen atom, a $C_1-C_6$ alkyl group or a $C_1-C_6$ alkanoyl group,
  or $R^6$ and $R^7$ together represent said alkylene group having at least one substituent selected from the group consisting of substituents (b), defined below;
$R^{2a}$ represents a hydrogen atom, a $C_1-C_6$ alkyl group or a $C_1-C_6$ alkanoyl group;
$R^3$ and $R^4$ are independently selected from the group consisting of $C_1-C_6$ alkyl groups, $C_2-C_6$ alkenyl groups, $C_2-C_6$ alkynyl groups, aralkyl groups where the alkyl part is $C_1-C_3$ alkyl and the aryl part is $C_1-C_{10}$ carbocyclic aromatic which is unsubstituted or has at least one substituent selected from the group consisting of substituents (c), cycloalkylalkyl groups where the alkyl part is $C_1-C_3$ alkyl and the cycloalkyl part is $C_1-C_6$, and $C_1-C_6$ alkyl groups having at least one substituent selected from the group consisting of substituents (a), or one of $R^3$ and $R^4$, together with $R^2$, represents a $C_1-C_6$ alkylene group or a $C_1-C_6$ alkylene group whose carbon chain is interrupted by an oxygen or sulfur atom or by a group of formula $R^8N<$.
wherein is as defined above,
or one of $R^3$ and $R^4$, together with $R^2$, represents said alkylene group having at least one substituent selected from the group consisting of substituents (b), defined below; and
$-COOR^5$ represents a carboxy group, a group of formula $-COO^-$, a group of formula $-COOM_x$, where M is a cation and x is the reciprocal of the valence of the cation M, or a protected carboxy group and, where $-COOR^5$ represents a carboxy group, a group of formula $-COOM_x$ or a protected carboxy group, the compound of formula (I) also contains an anion;
l, m and n are independently zero, or an integer from 1 to 3, provided that (m+n) is an integer from 2 to 6;
p is zero or the integer 1 or 2;
Y represents a single bond, an oxygen atom, a sulfur atom or a group of formula $R^8N<$.
  wherein $R^8$ is as defined above,
substituents (a):
hydroxy groups, cyano groups, carbamoyloxy groups, azido groups, carboxy groups, nitro groups, oxo groups, halogen atoms, $C_1-C_6$ alkoxy groups, $C_1-C_6$ alkanoyl groups, $C_1-C_6$ alkanoyloxy groups, $C_1-C_6$ alkanoylamino groups, $C_1-C_7$ alkoxycarbonyl groups, groups of formula $-NR^{10}R^{11}$ and $-CONR^{12}R^{13}$
  in which $R^{10}$, $R^{11}$, and $R^{13}$ are independently selected from the group consisting of hydrogen atoms, $C_1-C_6$ alkyl groups and $C_1-C_6$ alkanoyl groups,
groups of formula $-SO_2NR^{14}R^{15}$ and $-S(O)_kR^{16}$
  wherein $R^{14}$, $R^{15}$ and $R^{16}$ are independently selected from the group consisting of $C_1-C_6$ alkyl groups and k is zero or an integer 1 or 2, and groups of formula $-NHSO_2R^{17}$, $-N=CR^{18}NR^{19}R^{20}$, $-N=CR^{21}CR^{22}=NR^{23}$ and $-C(=NH)NR^{24}R^{25}$
  wherein $R^{17}$ to $R^{25}$ are independently selected from the group consisting of hydrogen atoms and $C_1-C_6$ alkyl groups;
substituents (b):
hydroxy groups, cyano groups, carbamoyl groups, oxo groups, halogen atoms, $C_1-C_6$ alkyl groups and $C_1-C_6$ alkoxy groups;
substituents (c):
$C_1-C_4$ alkyl groups, $C_1-C_4$ alkoxy groups, $C_1-C_4$ haloalkyl groups, $C_1-C_3$ alkylenedioxy groups, halogen atoms, cyano groups and nitro groups;
and pharmaceutically acceptable salts and esters thereof.

The invention also provides a pharmaceutical composition comprising an effective amount of an antibiotic in admixture with a pharmaceutically acceptable carrier or diluent, wherein the antibiotic is at least one compound selected from the group consisting of compounds of formula (I) and pharmaceutically acceptable salts and esters thereof.

The invention still further provides a method for the treatment or prevention of microbial infection by the administration to a mammal, which may be human, of an effective amount of an antibiotic, wherein the antibiotic is at least one compound selected from the group consisting of compounds of formula (I) and pharmaceutically acceptable salts and esters thereof.

The invention also provides processes for preparing the compounds of the present invention, which are described in more detail hereinafter.

DETAILED DESCRIPTION OF INVENTION

In the compounds of the present invention, where $R^2$, $R^{2a}$, $R^3$, $R^4$, $R^6$, $R^7$, $R^8$, $R^9$, $R^{10}$ $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$ or substituent (b) represents an alkyl group, this may be a straight or branched chain alkyl group containing from 1 to 6 carbon atoms, and examples include the methyl, ethyl, propyl, isopropyl, butyl, isobutyl, sec-butyl, t-butyl, pentyl, isopentyl, 2-methylbutyl, hexyl, isohexyl and 2-methylpentyl groups, of which the methyl, ethyl, propyl and butyl groups are preferred, the methyl group generally being most preferred.

In the case of $R^2$ and $R^{2a}$, the most preferred of the unsubstituted alkyl groups is the methyl group. In the case of $R^3$ and $R^4$, the most preferred of the unsubstituted alkyl groups are the methyl and ethyl groups, the methyl group being preferred of these. In the care of $R^6$ and $R^7$, the most preferred of the unsubstituted alkyl groups are the methyl, ethyl and isopropyl groups, the methyl and ethyl groups being especially preferred of these.

Where $R^2$, $R^{2a}$, $R^8$, $R^{10}$, $R^{11}$, $R^{12}$, $R^{13}$ or substituent (a) represents an alkanoyl group, this may be a straight or branched chain alkanoyl group containing from 1 to 6 carbon atoms, and examples include the formyl, acetyl, propionyl, butyryl, isobutyryl, valeryl, isovaleryl, pivaloyl and hexanoyl groups, of which the formyl and acetyl groups are more preferred.

Where $R^2$ or substituent (a) represents an alkanoylamino group, this may be a straight or branched chain alkanoylamino group containing from 1 to 6 carbon atoms, and examples include the formamido, acetamido, propionamido, butyramido, isobutyramido, valerylamino, isovalerylamino, pivaloylamino and hexanoylamino groups, of which the acetamido group is more preferred.

Where $R^2$ or substituent (a) represents an alkanoyloxy group, this may be a straight or branched chain alkanoyloxy group containing from 1 to 6 carbon atoms, and examples include the formyloxy, acetoxy, propionyloxy, butyryloxy, isobutyryloxy, valeryloxy, isovaleryloxy, pivaloyloxy and hexanoyloxy groups, of which the acetoxy, propionyloxy, butyryloxy, isobutyryloxy and pivaloyloxy groups are more preferred, and the acetoxy group is most preferred.

Where $R^2$ or substituent (a) or (b) represents a halogen atom, this may be a fluorine, chlorine, iodine or bromine atom, of which the fluorine, chlorine and bromine atoms are preferred, the fluorine and chlorine atoms being most preferred.

Where $R^2$ or substituent (a) or (b) represents an alkoxy group, this may be a straight or branched chain alkoxy group containing from 1 to 6 carbon atoms, and examples include the methoxy, ethoxy, propoxy, isopropoxy, butoxy, isobutoxy, sec-butoxy, t-butoxy, pentyloxy, isopentyloxy, 2-methylbutoxy, hexyloxy, isohexyloxy and 2-methylpentyloxy groups, of which the methoxy, ethoxy, propoxy and butoxy groups are preferred, the methoxy group generally being most preferred.

Where $R^2$ or substituent (a) represents an alkoxycarbonyl group, this may be a straight or branched chain alkoxy group containing, in total, from 2 to 7 carbon atoms, including the carbon atom of the carbonyl group (i.e. the alkoxy part contains from 1 to 6 carbon atoms), and examples include the methoxycarbonyl, ethoxycarbonyl, propoxycarbonyl, isopropoxycarbonyl, butoxycarbonyl, isobutoxycarbonyl, sec-butoxycarbonyl, t-butoxycarbonyl, pentyloxycarbonyl, isopentyloxycarbonyl, 2-methylbutoxycarbonyl, hexyloxycarbonyl, isohexyloxycarbonyl and 2-methylpentyloxycarbonyl groups, of which the methoxycarbonyl and ethoxycarbonyl groups are most preferred.

Where $R^2$ represents a group of formula $-S(O)_jR^9$, where j is 0, the group is an alkylthio group, when j is 1, the group is an alkylsulfinyl group, and, when j is 2, the group is an alkylsulfonyl group. The alkyl parts of these groups may be as already exemplified, and specific examples of these groups include the methylthio, ethylthio, propylthio, isopropylthio, butylthio, isobutylthio, sec-butylthio, t-butylthio, pentylthio, isopentylthio, 2-methylbutylthio, hexylthio, isohexylthio, 2-methylpentylthio, methylsulfinyl, ethylsulfinyl, propylsulfinyl, isopropylsulfinyl, butylsulfinyl, isobutylsulfinyl, sec-butylsulfinyl, t-butylsulfinyl, pentylsulfinyl, isopentylsulfinyl, 2-methylbutylsulfinyl, hexylsulfinyl, isohexylsulfinyl, 2-methylpentylsulfinyl, methylsulfonyl, ethylsulfonyl, propylsulfonyl, isopropylsulfonyl, butylsulfonyl, isobutylsulfonyl, sec-butylsulfonyl, t-butylsulfonyl, pentylsulfonyl, isopentylsulfonyl, 2-methylbutylsulfonyl, hexylsulfonyl, isohexylsulfonyl and 2-methylpentylsulfonyl groups, of which the methylthio, methylsulfinyl and methylsulfonyl groups are most preferred.

Where $R^6$ and/or $R^7$ represents a cycloalkyl group, this has from 3 to 6 ring carbon atoms, and examples include the cyclopropyl, cyclobutyl, cyclopentyl and cyclohexyl groups, of which the cyclopropyl, cyclopentyl and cyclohexyl groups are more preferred and the cyclopropyl group is most preferred.

Where $R^3$, $R^4$, $R^6$ or $R^7$ represents an alkenyl group, this has from 2 to 6 carbon atoms and may be a straight or branched chain group. Examples include the vinyl, 1-propenyl, allyl, isopropenyl, methallyl, 1-butenyl, 2-butenyl, 3-butenyl, 2-propylallyl, 1-pentenyl, 2-pentenyl, 3-pentenyl, 4-pentenyl, 1-butylvinyl, 2-methyl-3-pentenyl, 4-methyl-3-pentenyl, 1-methyl-4-pentenyl, 1-hexenyl, 2-hexenyl, 3-hexenyl, 4-hexenyl, 5-hexenyl, 3-methyl-1-butenyl, 3-methyl2-butenyl, 3-methyl-3-butenyl, 3-methyl-1-pentenyl, 3-methyl-2-pentenyl, 3-methyl-3-pentenyl, 3-methyl4-pentenyl and 3-methyl-1-hexenyl groups, of which the allyl, butenyl and pentenyl groups are preferred and the allyl group is most preferred.

Where $R^3$, $R^4$, $R^6$ or $R^7$ represents an alkenyl group, this has from 2 to 6 carbon atoms and may be a straight or branched chain group. Examples include the ethynyl, 1-propynyl, 2-propynyl (i.e. propargyl), 1-butynyl, 2-butynyl, 3-butynyl, 1-methyl-2-butynyl, 1-pentynyl, 2-pentynyl, 3-pentynyl, 4-pentynyl, 1-methyl-2-pentynyl, 1-methyl-3-pentynyl, 1-hexynyl, 2-hexynyl, 3-hexynyl, 4-hexynyl, 5-hexynyl, 3-methyl-1-butynyl, 3-methyl-2-butynyl, 3-methyl-3-butynyl, 3-methyl-1-pentynyl, 3-methyl-2-pentynyl, 3-methyl-3-pentynyl, 3-methyl-4-pentynyl and 3-methyl-1-hexynyl groups, of which the propargyl, butynyl and pentynyl groups are preferred and the propargyl group is most preferred.

Where $R^3$ or $R^4$ represents an aralkyl group, the alkyl part is a $C_1$–$C_3$ alkyl group and the aryl part is a $C_6$–$C_{10}$ carbocyclic aromatic group which may be substituted or unsubstituted and, if substituted, has at least one substituent selected from the group consisting of substituents (c) defined above and exemplified below. However, the unsubstituted groups are preferred. Examples of the alkyl parts of such aralkyl groups (which may be straight or branched chain groups) include the methyl, ethyl, propyl and isopropyl groups, of which the methyl and ethyl groups are preferred. Examples of the aryl parts include the phenyl and naphthyl (1- and 2-naphthyl) groups, of which the phenyl group is preferred. Examples of such aralkyl groups include the benzyl, phenethyl, 1-phenylethyl, 3-phenylpropyl, 2-phenylpropyl, 1-naphthylmethyl, 2-naphthylmethyl, 2-(1-naphthyl)ethyl and 2-(2-naphthyl)ethyl groups, of which the benzyl or phenethyl groups are preferred and the benzyl group is most preferred.

Where $R^3$ or $R^4$ represents a cycloalkylalkyl group, the alkyl part is a $C_1$–$C_3$ alkyl group and the cycloalkyl part is a $C_1$–$C_6$ cycloalkyl group. Examples of such alkyl groups are as given above in relation to the alkyl parts of aralkyl groups, and examples of such cycloalkyl groups are as given above in relation to the same groups which may be represented by $R^3$ and $R^4$. In this case, preferred alkyl parts are the methyl and ethyl, especially methyl, groups and preferred cycloalkyl groups are the cyclopropyl, cyclopentyl and cyclohexyl groups, of which the cyclopentyl and cyclohexyl groups are most preferred. Examples of such cycloalkylalkyl groups include the cyclopropylmethyl, cyclobutylmethyl, cyclopentylmethyl, cyclohexylmethyl, 2-cyclopropylethyl, 2-cyclobutylethyl, 2-cyclopentylethyl, 2-cyclohexylethyl, 1-cyclopropylethyl, 1-cyclobutylethyl, 1-cyclopentylethyl, 1-cyclohexylethyl, 2-cyclopropylpropyl, 2-cyclobutylpropyl, 2-cyclopentylpropyl, 2-cyclohexylpropyl, 1-cyclopropylpropyl, 1-cyclobutylpropyl, 1-cyclopentylpropyl, 1-cyclohexylpropyl, 3-cyclopropylpropyl, 3-cyclobutylpropyl, 3-cyclopentylpropyl, 3-cyclohexylpropyl, 1-methyl-1-cyclopropylethyl, 1-methyl-1-cyclobutylethyl, 1-methyl-1-cyclopentylethyl and 1-methyl-1-cyclohexylethyl groups, of which the cyclopropylmethyl, cyclopentylmethyl, cyclohexylmethyl and 2-cyclopropylethyl groups are preferred and the cyclopropylmethyl, cyclopentylmethyl and cyclohexylmethyl groups are most preferred.

Where either $R^3$ or $R^4$, taken together with $R^2$, represents an alkylene group which may contain an oxygen or sulfur atom or a group of formula $>NR^8$ (wherein $R^8$ represents a hydrogen atom, an alkyl group or an alkanoyl group), it contains from 1 to 6 carbon atoms in the chain and may, for example, be a group of formula —CH—, —(CH$_2$)$_2$—, —(CH$_2$)$_3$—, —(CH$_2$)$_4$—, —(CH$_2$)$_5$—, —(CH$_2$)$_6$—, —(CH$_2$)$_{20}$—, —(CH$_2$)$_2$OCH$_2$—, —CH$_2$OCH$_2$—, —(CH$_2$)$_2$O(CH$_2$)$_2$—, —(CH$_3$)O(CH$_2$)$_2$—, —(CH$_2$)$_3$O(CH$_2$)$_3$—, —CH$_2$NE$^8$—, —(CH$_2$)$_2$NR$^8$—, —CH$_2$NR$^8$CH$_2$—, —(CH$_2$)$_2$NR$^8$CH$_2$—, (CH$_2$)$_2$NR$^8$(CH$_2$)$_2$—, —CH$_2$S—, —(CH$_2$)$_2$S—, —CH$_2$SCH$_2$—, —(CH$_2$)$_2$SCH$_2$— or —(CH$_2$)$_2$S(CH$_2$)$_2$—, and is more preferably a group of formula —CH$_2$—, —(CH$_2$)$_2$—, —(CH$_2$)$_3$—, —(CH$_2$)$_4$—, —(CH$_2$)$_5$-, —(CH$_2$)$_2$O—, —(CH$_2$)$_2$OCH$_2$—, —(CH$_2$)$_2$O(CH$_2$)$_2$—, —(CH$_2$)$_2$NR$^8$—, —(CH$_2$)$_2$NR$^8$CH$_2$—, (CH$_2$)$_2$NR$^8$(CH$_2$)$_2$—, —(CH$_2$)$_2$S—, —(CH$_2$)$_2$SCH$_2$— or —(CH$_2$)$_2$S(CH$_2$)$_2$—, and such groups may be unsubstituted or may have at least one substituent selected from the group consisting of substituents (b), defined above and exemplified below. Including such substituted groups, the most preferred groups which may be represented by $R^3$ or $R^4$+$R^2$ are the groups of formula —CH$_2$—, —(CH$_2$)$_2$—, —(CH$_2$)$_3$—, —(CH$_2$)$_4$—, —(CH$_2$)$_2$OCH$_2$—, —(CH$_2$)$_2$SCH$_2$—, —(CH$_2$)$_2$NMeCH$_2$—, —(CH$_2$)$_2$NAcCH$_2$—, —(CH$_2$)$_2$NHCH$_2$—, —(CH$_2$)$_2$NHCO—, —(CH$_2$)$_2$NMeCO—, —CH$_2$—CO—NH—CO—, —CH$_2$—CHMe—NH—CH—, —CH$_2$—CHMe—CH$_2$—, —(CH$_2$)$_2$—CHOH— and —(CH$_2$)$_2$—CHF— (in which Me represents the methyl group and Ac represents the acetyl group).

Where $R^6$ together with $R^7$ represents an alkylene group which may contain an oxygen or sulfur atom or a group of formula $>NR^8$ (in which $R^8$ represents a hydrogen atom, an alkyl group or an alkanoyl group), it contains from 1 to 6 carbon atoms in the chain and may, for example, be a group of formula —CH$_2$—, —(CH$_2$)$_2$—, —(CH$_2$)$_3$—, —(CH$_2$)$_4$—, —(CH$_2$)$_5$—, —(CH$_2$)$_6$—, —(CH$_2$)$_2$O—, —(CH$_2$)$_2$OCH$_2$—, —CH$_2$OCH$_2$—, —(CH$_2$)$_2$O(CH$_2$)$_2$—, —(CH$_2$)$_3$O(CH$_2$)$_2$—, —(CH$_2$)$_3$O(CH$_2$)$_3$—, —CH$_2$NR$^8$—, —(CH$_2$) —CH$_2$NR$^8$—, —CH$_2$NR$^8$CH$_2$—, —(CH$_2$)$_2$NR$^8$CH$_2$—, (CH$_{22}$)NR$^8$(CH$_2$)$_2$—, —CH$_2$S—, —(CH$_2$)$_2$S—, —CH$_2$SCH$_2$—, —(CH$_2$)$_2$SCH$_2$— or —(CH$_2$)$_2$S(CH$_2$)$_2$—, and is more preferably a group of formula —(CH$_2$)$_2$—, —(CH$_2$)$_3$—, —(CH$_2$)$_4$—, —(CH$_2$)$_5$—, —(CH$_2$)$_2$OCH$_2$—, —(CH$_2$)$_2$O(CH$_2$)$_2$—, —(CH$_2$)$_2$NR$^8$CH$_2$—, —(CH$_2$)$_2$NR$^8$(CH$_2$)$_2$—, —(CH$_2$)$_2$SCH$_2$— or —CH$_2$)$_2$S(CH$_2$)$_2$, and such groups may be unsubstituted or may have at least one substituent selected from the group consisting of substituents (b), defined above and exemplified below. Including such substituted groups, the most preferred groups which may be represented by $R^6$ and $R^7$ together are groups of formula —(CH$_2$)$_2$—, —(CH$_2$)$_3$—, —(CH$_2$)$_4$—, —(CH$_2$)$_5$—, —(CH$_2$)$_2$O (CH$_2$)$_2$—, —(CH$_2$)$_2$S(CH$_2$)$_2$, —(CH$_2$)$_2$NHCH$_2$—, —(CH$_2$)$_2$NMeCH$_2$—, —(CH$_2$)$_2$NAcCH$_2$—, —CH$_2$—CHOH—(CH$_2$)$_2$—, —CH$_2$—CHMe—(CH$_2$)$_2$—, —CH$_2$—CHF—(CH$_2$)$_2$—, —CO—(CH$_2$)$_3$—, —CH(NH$_2$CO)—(CH$_2$)$_3$—, —CH$_2$—CH(MeO)—(CH$_2$)$_2$—, —CH$_2$—CO—(CH$_2$)$_2$— and —CH$_2$—CH(CN)—(CH$_2$)$_2$— groups.

Specific examples of atoms and groups which are included within substituents (a) include:

hydroxy groups, cyano groups, carbamoyloxy groups, azido groups, carboxy groups, nitro groups and oxo groups;

halogen atoms, such as the chlorine, fluorine, bromine and iodine atoms, especially the chlorine and fluorine atoms;

$C_1$–$C_6$ alkoxy groups, $C_1$–$C_6$ alkanoyl groups, $C_1$–$C_6$ alkanoyloxy groups, $C_1$–$C_6$ alkanoylamino groups and $C_2$–$C_7$ alkoxycarbonyl groups, as exemplified above;

groups of formula -NR$^{10}$R$^{11}$ and —CONR$^{12}$R$^{13}$, i.e. amino and carbamoyl groups and alkyl-substituted and alkanoyl-substituted derivatives thereof, such as the amino, methylamino, ethylamino, propylamino, isopropylamino, butylamino, isobutylamino, sec-butylamino, t-butylamino, dimethylamino, diethylamino, dipropylamino, diisopropylamino, dibutylamino, carbamoyl, methylcarbamoyl, ethylcarbamoyl, propylcarbamoyl, isopropylcarbamoyl, butylcarbamoyl, isobutylcarbamoyl, sec-butylcarbamoyl, t-butylcarbamoyl, dimethylcarbamoyl, diethylcarbamoyl, dipropylcarbamoyl, diisopropylcarbamoyl, dibutylcarbamoyl, formamido, acetamido, propionamido, butyramido, isobutyramido, valerylamino, isovalerylamino, pivaloylamino, hexanoylamino formylcarbamoyl, acetylcarbamoyl, propionylcarbamoyl, butyrylcarbamoyl, isobutyrylcarbamoyl, valerylamino, isovalerylamino, pivaloylcarbamoyl and hexanoylcarbamoyl groups;

groups of formula SO$_2$NR$^{14}$R$^{15}$ and —S(O)$_k$R$^{16}$, i.e. sulfamoyl, thio, sulfinyl and sulfonyl groups, for example the methylsulfamoyl, ethylsulfamoyl, propylsulfamoyl, isopropylsulfamoyl, butylsulfamoyl, isobutylsulfamoyl, sec-butylsulfamoyl, t-butylsulfamoyl, dimethylsulfamoyl, diethylsulfamoyl, dipropylsulfamoyl, diisopropylsulfamoyl, dibutylsulfamoyl, and the thio, sulfinyl and sulfonyl groups exemplified for $R^2$ where $R^2$ represents a group of formula —S(O)$_j$R$^9$:

groups of formula —NHSO$_2$R$^{17}$ —N=CR$^{18}$NR$^{19}$R$^{20}$, —N=CR$^{21}$CR$^{22}$=NR$^{23}$ and —C(=NH)NR$^{24}$R$^{25}$, in which R$^{17}$ to R$^{25}$ are as defined and exemplified above.

Specific examples of atoms and groups which are included within substituents (b) include:

hydroxy groups, cyano groups, carbamoyl groups, and oxo groups;

halogen atoms, C$_1$–C$_6$ alkoxy groups and C$_1$–C$_6$ alkyl groups, as exemplified above.

Where R$^2$, R$^3$, R$^4$, R$^6$ or R$^7$ represents an alkyl group having at least one substituent selected from the group consisting of substituents (a), these substituents are defined and exemplified above. Specific examples of such substituted groups include the fluoromethyl, difluoromethyl, trifluoromethyl, 2-fluoroethyl, 2,2,2-trifluoroethyl, 3-fluoropropyl, 2-chloroethyl, 5-fluoropentyl, 6-chlorohexyl, carbamoylmethyl, methylcarbamoylmethyl, N,N-dimethylcarbamoylmethyl, 2-carbamoylethyl, 3-carbamoylpropyl, carbamoyloxymethyl, 2-carbamoyloxyethyl, cyanomethyl, 2-cyanoethyl, 3-cyanopropyl, carboxymethyl, 2-carboxyethyl, 4-carboxybutyl, methoxycarbonylmethyl, 2-methoxycarbonylethyl, ethoxycarbonylmethyl, 2-ethoxycarbonylethyl, 3-methoxycarbonylpropyl, 3-ethoxycarbonylpropyl, hydroxymethyl, 2-hydroxyethyl, 3-hydroxypropyl, 4-hydroxybutyl, 5-hydroxypentyl, 6-hydroxyhexyl, methoxymethyl, 2-methoxyethyl, ethoxymethyl, 4-methoxybutyl, 2-pentoxyethyl, methylthiomethyl, 2-methylthioethyl, ethylthiomethyl, 4-methylthiobutyl, 3-butylthiopropyl, methylsulfinylmethyl, methylsulfonylmethyl, acetylmethyl, 2-acetylethyl, propionylmethyl, 2-propionylethyl, 3-propionylpropyl, 4-propionylbutyl, N$^1$,N$^1$-dimethylamidinomethyl, acetamidomethyl, sulfamoylmethyl, 2-(1-iminoethylamino)ethyl, nitromethyl, 2-(1-aminoethylideneamino)ethyl, 2-[N-(1-iminoethyl)-N-methylamino]ethyl, dimethylaminomethyl, methylsulfonylaminomethyl, amidinomethyl, (N-iminomethyl-N-methylamino)methyl, (1-aminoethylideneamino)methyl and N-(1-iminoethyl)-N-methylamino]methyl groups.

R$^5$ represents a hydrogen atom or a protecting group, which is capable of removal under chemically moderate conditions such as by means of a chemical reducing reagent or by catalytic reduction, or which is capable of removal by means of biological reactions. e.g. in vivo, to produce a carboxy group. There is no limitation upon the nature of such a protecting group. provided that, where the resulting compound is to be used for therapeutic purposes, it is pharmaceutically acceptable, which, as is well-known in the art, means that the compound does not have reduced activity (or unacceptably reduced activity) or increased toxicity (or unacceptably increased toxicity) compared with the corresponding compound of formula (I) where R$^5$ represents a hydrogen atom. Where, however, the compound is to be used for non-therapeutic purposes, e.g. as an intermediate in the preparation of other compounds, even this limitation does not apply, and the protecting group may be chosen having regard simply to process criteria. Examples of groups which may be represented by R$^5$ include:

C$_1$–C$_{20}$ alkyl groups, more preferably C$_1$–C$_6$ alkyl groups, such as those exemplified in relation to R$^2$ etc and higher alkyl groups as are well known in the art, such as the heptyl, octyl, nonyl and decyl groups, but most preferably the methyl, ethyl and t-butyl groups;

C$_3$–C$_7$ cycloalkyl groups, for example where the cycloalkyl group is any one of those C$_1$–C$_6$ cycloalkyl groups described herein in relation to R$^6$ and R$^7$ or the cycloheptyl group;

aralkyl groups. as defined and exemplified above in relation to R$^3$ and R$^4$ but in which the aromatic group is C$_6$–C$_{14}$, which may be substituted or unsubstituted, and, if substituted may have at least one substituent selected from the group consisting of substituents (c), defined above and exemplified below; examples of such aralkyl groups include the benzyl, phenethyl, 1-phenylethyl, 3-phenylpropyl, 2-phenylpropyl, 1-naphthylmethyl, 2-naphthylmethyl, 2-(1-naphthyl)ethyl, 2-(2-naphthyl)ethyl, benzhydryl (i.e. diphenylmethyl), triphenylmethyl, bis(o-nitrophenyl)methyl, 9-anthrylmethyl, 2,4,6-trimethylbenzyl, 4-bromobenzyl, 2-nitrobenzyl, 4-nitrobenzyl, 2-nitrobenzyl, 4-methoxybenzyl and piperonyl groups;

alkenyl groups such as those defined and exemplified above in relation to R$^3$ and R$^4$, but which may be substituted or unsubstituted and, if substituted have at least one substituent selected from the group consisting of substituents (a) defined above; examples of the unsubstituted groups are given above in relation to R$^3$ and R$^4$, and preferred groups include the allyl, 2-chloroallyl and 2-methylallyl groups;

halogenated C$_1$–C$_6$, preferably C$_1$–C$_4$, alkyl groups in which the alkyl part is as defined and exemplified in relation to the alkyl groups which may be represented by R$^2$ etc, and the halogen atom is chlorine, fluorine, bromine or iodine, such as the 2,2,2-trichloroethyl, 2-haloethyl (e.g. 2-chloroethyl, 2-fluoroethyl, 2-bromoethyl or 2-iodoethyl), 2,2-dibromoethyl and 2,2,2-tribromoethyl group;

substituted silylalkyl groups, in which the alkyl part is as defined and exemplified in relation to the alkyl groups which may be represented by R$^2$ etc, and the silyl group has up to 3 substituents selected from the group consisting of C$_1$–C$_6$ alkyl groups and phenyl groups which are unsubstituted or have at least one substituent selected from the group consisting of substituents (a) defined and exemplified above, for example a 2-trimethylsilylethyl group;

phenyl groups, in which the phenyl group is unsubstituted or substituted, preferably with at least one C$_1$—C$_4$ alkyl or acylamino group, for example the phenyl, tolyl and benzamidophenyl groups;

phenacyl groups, which may be unsubstituted or have at least one substituent selected from the group consisting of substituents (a) defined and exemplified above, for example the phenacyl group itself or the p-bromophenacyl group;

cyclic and acyclic terpenyl groups, for example the geranyl, neryl, linalyl, phytyl, menthyl (especially m- and p- menthyl), thujyl, caryl, pinanyl, bornyl, notcaryl, norpinanyl, norbornyl, menthenyl, camphenyl and norbornenyl groups;

alkoxymethyl groups, in which the alkoxy part is C$_1$–C$_6$, preferably C$_1$–C$_4$, and may itself be substituted by a single unsubstituted alkoxy group, such as the methoxymethyl, ethoxymethyl, propoxymethyl, isopropoxymethyl, butoxymethyl and methoxyethoxymethyl groups;

aliphatic acyloxymethyl groups, in which the acyl group is preferably an alkanoyl group and is more preferably a C$_2$–C$_6$ alkanoyl group, such as the acetoxymethyl, propionyloxymethyl, butyryloxymethyl, isobutyryloxymethyl and pivaloyloxymethyl groups;

higher aliphatic acyloxyalkyl groups in which the acyl group is preferably an alkanoyl group and is more preferably a $C_2$-$C_6$ alkanoyl group, and the alkyl part is $C_2$-$C_6$, and preferably $C_2$-$C_4$, such as the 1-pivaloyloxyethyl, 1-acetoxyethyl, 1-isobutyryloxyethyl, 1-pivaloyloxypropyl, 2-methyl-1-pivaloyloxypropyl, 2-pivaloyloxypropyl, 1-isobutyryloxyethyl, 1-isobutyryloxypropyl, 1-acetoxypropyl, 1-acetoxy-2-methylpropyl, 1-propionyloxyethyl, 1-propionyloxypropyl, 2-acetoxypropyl and 1-butyryloxyethyl groups;

cycloalkyl-substituted aliphatic acyloxyalkyl groups, in which the acyl group is preferably an alkanoyl group and is more preferably a $C_1$-$C_6$ alkanoyl group, the cycloalkyl substituent is $C_3$-$C_7$, and the alkyl part is a $C_1$-$C_6$ alkyl group, preferably a $C_1$-$C_4$ alkyl group, such as the (cyclohexylacetoxy)methyl, 1-(cyclohexylacetoxy)ethyl, 1-(cyclohexylacetoxy)propyl, 2-methyl-1-(cyclohexylacetoxy)propyl, (cyclopentylacetoxy)methyl, 1-(cyclopentylacetoxy)ethyl 1-(cyclopentylacetoxy)propyl and 2-methyl-1-(cyclopentylacetoxy)propyl, groups;

alkoxycarbonyloxyalkyl groups, especially 1-(alkoxycarbonyloxy)ethyl groups, in which the alkoxy part is $C_1$-$C_{10}$, preferably $C_1$-$C_6$, and more preferably $C_1$-$C_4$, and the alkyl part is $C_1$-$C_6$, preferably $C_1$-$C_4$, such as the 1-methoxycarbonyloxyethyl, 1-ethoxycarbonyloxyethyl, 1-propoxycarbonyloxyethyl, 1-isopropoxycarbonyloxyethyl, 1-butoxycarbonyloxyethyl, 1-isobutoxycarbonyloxyethyl, 1-sec-butoxycarbonyloxyethyl, 1-t-butoxycarbonyloxyethyl, 1-(1-ethylpropoxycarbonyloxy)ethyl and 1-(1,1-dipropylbutoxycarbonyloxy)ethyl groups, and other alkoxycarbonylalkyl groups, in which both the alkoxy and alkyl groups are $C_1$-$C_6$, preferably $C_1$-$C_4$, such as the 2-methyl-1-(isopropoxycarbonyloxy)propyl, 2-(isopropoxycarbonyloxy)propyl, isopropoxycarbonyloxymethyl, t-butoxycarbonyloxymethyl, methoxycarbonyloxymethyl and ethoxycarbonyloxymethyl groups;

cycloalkylcarbonyloxyalkyl and cycloalkyloxycarbonyloxyalkyl groups, in which the cycloalkyl group is $C_3$-$C_{10}$, preferably $C_3$-$C_7$, is mono- or polycyclic and is optionally substituted by at least one (and preferably only one) $C_1$-$C_4$ alkyl group (e.g. selected from those alkyl groups exemplified above) and the alkyl group is a $C_1$-$C_6$, more preferably $C_1$-$C_4$, alkyl group (e.g. selected from those alkyl groups exemplified above) and is most preferably methyl, ethyl or propyl, for example the 1-methylcyclohexylcarbonyloxymethyl, 1-methylcyclohexyoxycarbonyloxymethyl, cyclopentyloxycarbonyloxymethyl, cyclopentylcarbonyloxymethyl, 1-cyclohexyloxycarbonyloxyethyl, 1-cyclohexylcarbonyloxyethyl, 1-cyclopentyloxycarbonyloxyethyl, 1-cyclopentylcarbonyloxyethyl, 1-cycloheptyloxycarbonyloxyethyl, 1-cycloheptylcarbonyloxyethyl, 1-methylcyclopentylcarbonyloxymethyl, 1-methylcyclopentyloxycarbonyloxymethyl, 2-methyl-1-(1-methylcyclohexylcarbonyloxy)propyl, 1-(1-methylcyclohexylcarbonyloxy)propyl, 2-(1-methylcyclohexylcarbonyloxy)propyl, 1-(cyclohexylcarbonyloxy)propyl, 2-(cyclohexylcarbonyloxy)propyl, 2-methyl-1-(1-methylcyclopentylcarbonyloxy)propyl, 1-(1-methylcyclopentylcarbonyloxy)propyl, 2-(1-methylcyclopentylcarbonyloxy)propyl, 1-(cyclopentylcarbonyloxy)propyl, 2-(cyclopentylcarbonyloxy)propyl, 1-(1-methylcyclopentylcarbonyloxy)ethyl, 1-(1-methylcyclopentylcarbonyloxy)propyl, adamantyloxycarbonyloxymethyl, adamantylcarbonyloxymethyl, 1-adamantyloxycarbonyloxyethyl and 1-adamantylcarbonyloxyethyl groups;

cycloalkylalkoxycarbonyloxyalkyl groups in which the alkoxy group has a single cycloalkyl substituent, the cycloalkyl substituent being $C_1$-$C_{10}$, preferably $C_1$-$C_7$, and mono- or poly- cyclic, for example the cyclopropylmethoxycarbonyloxymethyl, cyclobutylmethoxycarbonyloxymethyl, cyclopentylmethoxycarbonyloxymethyl, cyclohexylmethoxycarbonyloxymethyl, 1-(cyclopropylmethoxycarbonyloxy)ethyl, 1-(cyclobutylmethoxycarbonyloxy)ethyl, 1-(cyclopentylmethoxycarbonyloxy)ethyl and 1-(cyclohexylmethoxycarbonyloxy)ethyl groups;

terpenylcarbonyloxyalkyl and terpenyloxycarbonyloxyalkyl groups, in which the terpenyl group is as exemplified above in relation to the terpenyl groups which may be represented by $R^5$, and is preferably a cyclic terpenyl group, for example the 1-(menthyloxycarbonyloxy)ethyl, 1-(menthylcarbonyloxy)ethyl, menthyloxycarbonyloxymethyl, menthylcarbonyloxymethyl, 1-(3-pinanyloxycarbonyloxy)ethyl, 1-(3-pinanylcarbonyloxy)ethyl, 3-pinanyloxycarbonyloxymethyl and 3-pinanylcarbonyloxymethyl groups;

5-alkyl or 5-phenyl [which may be substituted by at least one substituent selected from the group consisting of substituents (c)] (2-oxo-1,3-dioxolenyl)alkyl groups in which each alkyl group (which may be the same or different) is $C_1$-$C_6$, preferably $C_1$-$C_4$, for example the (5-methyl-2-oxo-1,3-dioxolen-4-yl)methyl, (5-phenyl-2-oxo-1,3-dioxolen-4-yl)methyl, (5-isopropyl-2-oxo-1,3-dioxolen-4-yl)methyl, (5-t-butyl-2-oxo-1,3-dioxolen-4-yl)methyl and 1-(5-methyl-2-oxo-1,3-dioxolen-4-yl)ethyl groups; and other groups, especially groups which are easily removed in vivo such as the phthalidyl, indanyl and 2-oxo-4,5,6,7-tetrahydro-1,3-benzodioxolen-4-yl groups.

Of the above groups, we especially prefer those groups which can be removed easily in vivo, and most preferably the aliphatic acyloxymethyl groups, higher aliphatic acyloxyalkyl groups, cycloalkyl-aliphatic acyloxyalkyl groups, alkoxycarbonyloxyalkyl groups, cycloalkylcarbonyloxyalkyl groups, and cycloalkylalkoxycarbonyloxyalkyl groups.

Where substituents (c) are $C_1$-$C_4$ alkyl groups, $C_1$-$C_4$ haloalkyl groups, halogen atoms, cyano groups and nitro groups, these may be as exemplified elsewhere above. Where substituent (c) is an alkylenedioxy group, this has from 1 to 3 carbon atoms and is preferably attached to 2 adjacent positions of the benzyl group which it substitutes. Examples include the methylenedioxy, dimethylenedioxy and trimethylenedioxy groups, of which the methylenedioxy group is preferred.

The compounds of the present invention can contain a basic group and can, therefore, form acid addition salts. Also, where $R^5$ represents a hydrogen atom, a cation or a protecting group and $R^a$ represents said group (II), an anion is required to balance the positive charge on the nitrogen atom in the group (II). This anion may be provided by an acid, as exemplified below. The nature of such salts and such acids is not critical to the invention, provided that, where the compound is intended for use therapeutically, the salt is pharmaceutically acceptable, which, as is well known, means that it does not have a lower (or significantly lower) activity or a higher (or significantly higher) toxicity than the free base. However, where the compound is intended for other uses, e.g. as an intermediate in the preparation of other compounds, even this limitation does not apply.

Examples of acids which can form such salts or can provide the balancing anion include: inorganic acids, such as hydrochloric acid, hydrobromic acid, hydroiodic acid, phosphoric acid, sulfuric acid or nitric acid; organic sulfonic acids, such as methanesulfonic acid, ethanesulfonic acid, benzenesulfonic acid or p-toluenesulfonic acid; and organic carboxylic acids, such as oxalic acid, tartaric acid, citric acid, maleic acid, succinic acid, acetic acid, benzoic acid, mandelic acid, ascorbic acid, lactic acid, gluconic acid and malic acid.

Examples of cations which may be represented M in the compounds of the present invention include: metal atoms, especially alkali metal atoms, such as the sodium and potassium atoms, and alkaline earth metal atoms, such as the calcium atom; the ammonium group; and cations derived from a trialkylamine, such as triethylamine, or from another organic base, such as procaine, dibenzylamine or phenethylamine.

Where the compound of the invention is an ester, i.e. $R^5$ represents a protecting group, we prefer those in which: $R^5$ represents: a $C_1-C_{20}$ alkyl group, more preferably a $C_1-C_6$ alkyl group; a $C_3-C_7$ cycloalkyl group; an aralkyl group in which the alkyl part is $C_1-C_3$ and the aromatic group is $C_6-C_{14}$ and is unsubstituted or has at least one substituent selected from the group consisting of substituents (c). defined above; a $C_2-C_6$ alkenyl group which is unsubstituted or has at least one substituent selected from the group consisting of substituents (a) defined above; a halogenated $C_1-C_6$, preferably $C_1-C_4$, alkyl group; a substituted silylalkyl group in which each alkyl part is $C_1-C_6$ and the silyl group has up to 3 substituents selected from the group consisting of $C_1-C_6$ alkyl groups and phenyl groups which are unsubstituted or have at least one substituent selected from the group consisting of substituents (a) defined above; a phenyl group which is unsubstituted or has at least one $C_1-C_4$ alkyl or acylamino substituent; a phenacyl group which is unsubstituted or has at least one substituent selected from the group consisting of substituents (a) defined above; a cyclic or acyclic terpenyl group; an alkoxymethyl group, in which the alkoxy part is $C_1-C_6$, preferably $C_1-C_4$, which is unsubstituted or is itself substituted by a single unsubstituted alkoxy group; an aliphatic acyloxymethyl group, in which the acyl group is preferably an alkanoyl group and is more preferably a $C_2-C_6$ alkanoyl group; a higher aliphatic acyloxyalkyl group in which the acyl group is preferably an alkanoyl group and is more preferably a $C_2-C_6$ alkanoyl group, and the alkyl part is $C_1-C_6$, and preferably $C_2-C_4$; a cycloalkyl-substituted aliphatic acyloxyalkyl group, in which the acyl group is preferably an alkanoyl group and is more preferably a $C_2-C_6$ alkanoyl group, the cycloalkyl substituent is $C_3-C_7$, and the alkyl part is a $C_1-C_6$ alkyl group, preferably a $C_1-C_4$ alkyl group; an alkoxycarbonyloxyalkyl group, especially a 1-(alkoxycarbonyloxy)ethyl group, in which the alkoxy part is $C_1-C_{10}$, preferably $C_1-C_6$, and more preferably $C_1-C_4$, and the alkyl part is $C_1-C_6$, preferably $C_1-C_4$; a cycloalkylcarbonyloxyalkyl or cycloalkyloxycarbonyloxyalkyl group, in which the cycloalkyl group is $C_3-C_{10}$, preferably $C_3-C_7$, is mono- or poly- cyclic and is optionally substituted by at least one $C_1-C_4$ alkyl group, and the alkyl group is a $C_1-C_6$, more preferably $C_1-C_4$, alkyl group; a cycloalkylalkoxycarbonyloxyalkyl group in which the alkoxy group has a single cycloalkyl substituent, the cycloalkyl substituent being $C_1-C_{10}$, preferably $C_3-C_7$, and mono- or poly- cyclic; a terpenylcarbonyloxyalkyl or terpenyloxycarbonyloxyalkyl group; a 5-alkyl- or 5-phenyl- substituted (2-oxo-1,3-dioxolen-4-yl)alkyl group in which each alkyl group is $C_1-C_6$, preferably $C_1-C_4$, and in which the phenyl group is unsubstituted or has at least one substituent selected from the group consisting of substituents (c); a phthalidyl group; an indanyl group; or a 2-oxo-4,5,6,7-tetrahydro-1,3-benzodioxolen-4-yl group.

Of all of the compounds of the present invention, we prefer those in which $R^a$ represents said group of formula (II). Of the compounds where $R^a$ represents said group of formula (II). the following are preferred:

(A) those compounds of formula (I), in which:
$R^a$ represents said group of formula (II), in which:
one of the symbols $R'$ represents a bond to the remainder of the compound of formula (I), one more of the symbols $R'$ is $R^2$ and the others of the symbols $R'$ all represent hydrogen atoms;
$R^1$ represents a hydrogen atom or a methyl group;
$R^2$ represents a hydrogen atom, a $C_1-C_4$ alkyl group, a $C_1-C_4$ alkyl group having at least one substituent selected from the group consisting of substituents (a'), a halogen atom, a hydroxy group, a $C_1-C_4$ alkoxy group, an amino group, a $C_1-C_6$ alkanoylamino group, a $C_1-C_6$ alkanoyloxy group, a $C_1-C_6$ alkanoyl group, a carboxy group, a $C_2-C_5$ alkoxycarbonyl group, a cyano group, a group of formula $-S(O)_jR^9$
  wherein j is zero or an integer 1 or 2 and $R^9$ represents a $C_1-C_4$ alkyl group;
or a group of formula $-CONR^6R^7$
  wherein $R^6$ and $R^7$ are independently selected from the group consisting of hydrogen atoms, $C_1-C_4$ alkyl groups, $C_3-C_6$ cycloalkyl groups, $C_2-C_4$ alkenyl groups, $C_3-C_4$ alkynyl groups and $C_1-C_4$ alkyl groups having at least one substituent selected from the group consisting of substituents (a'), or $R^6$ and $R^7$ together represent a $C_2-C_4$ alkylene group or a $C_1-C_4$ alkylene group whose carbon chain is interrupted by an oxygen or sulfur atom or by a group of formula $R^8N<$,
  wherein $R^8$ represents a hydrogen atom, a $C_1-C_4$ alkyl group or a $C_1-C_6$ alkanoyl group,
  or $R^6$ and $R^7$ together represent said alkylene group having at least one substituent selected from the group consisting of substituents (b), defined above;
$R^3$ and $R^4$ are independently selected from the group consisting of $C_1-C_4$ alkyl groups, $C_3-C_4$ alkenyl groups, $C_3-C_4$ alkynyl groups, benzyl groups, cycloalkylalkyl groups where the alkyl part is $C_1-C_3$ alkyl and the cycloalkyl part is $C_1-C$, and $C_1-C_4$ alkyl groups having at least one substituent selected from the group consisting of substituents (a'), or one of $R^3$ and $R^4$, together with $R^2$, represents a $C_2-C_4$ alkylene group or a $C_2-C_4$ alkylene group whose carbon chain is interrupted by an oxygen or sulfur atom or by a group of formula $R^8N<$,
  wherein R is as defined above, or one of $R^3$ and $R^4$, together with $R^2$, represents said alkylene group having at least one substituent selected from the group consisting of substituents (b), defined below; and —$COOR^5$ represents a carboxy group, a group of formula —$COO^-$ or a group of formula —$COOM_x$, where M is a cation and x is the reciprocal of the valence of the cation M, or $R^5$ is as defined in (A) above, and, where —$COOR^5$ represents a carboxy group, a group of formula —$COOM_x$ or a protected carboxy group, the compound of formula (I) also contains an anion;

l is zero or 1 and (m+n) is an integer from 2 to 6;

Y represents a single bond, an oxygen atom, a sulfur atom or a group of formula $R^8N<$, wherein $R^8$ is as defined above, substituents (a'):

hydroxy groups, cyano groups, carbamoyloxy groups, carboxy groups, nitro groups, halogen atoms, $C_1$-$C_3$ alkoxy groups, $C_1$-$C_6$ alkanoyl groups, $C_1$-$C_6$ alkanoyloxy groups, $C_1$-$C_6$ alkanoylamino groups, $C_2$-$C_5$ alkoxycarbonyl groups, groups of formula —$NR^{10}R^{11}$ and —$CONR^{12}R^{13}$, in which $R^{10}$, $R^{11}$, $R^{12}$ and $R^{13}$ are independently selected from the group consisting of hydrogen atoms, $C_1$-$C_4$ alkyl groups and $C_1$-$C_6$ alkanoyl groups, groups of formula and —$SO_1NR^{14}R^{15}$ and —$S(O)_kR^{16}$ wherein $R^{14}$, $R^{15}$ and $R^{16}$ are independently selected from the group consisting of $C_1$-$C_4$ alkyl groups and k is zero or an integer 1 or 2, and groups of formula —$NHSO_2R^{17}$, —$N=CR^{18}NR^{19}R^{20}$, —$N=CR^{21}CR^{22}=NR^{23}$ and —$C(=NH)NR^{24}R^{25}$ wherein $R^{17}$ to $R^{25}$ are independently selected from the group consisting of hydrogen atoms and $C_1$-$C_4$ alkyl groups;

and pharmaceutically acceptable salts and esters thereof.

The more preferred of these compounds are those in which:

(B) R represents a hydrogen atom or a methyl group; l is zero or an integer 1 or 2; (m+n) is an integer 2, 3, 4, 5 or 6; Y represents a single bond, an oxygen atom, a sulfur atom or a group of formula $R^8N<$ (wherein $R^8$ represents a hydrogen atom, a methyl group, an ethyl group, a formyl group or an acetyl group); $R^2$ represents a hydrogen atom, a fluorine atom, a hydroxy group, a methoxy group, an ethoxy group, an amino group, an acetamido group, an acetoxy group, a formyl group, an acetyl group, a carboxy group, a methoxycarbonyl group, an ethoxycarbonyl group, a cyano group, a group of formula —$CONR^6R^7$, wherein:

$R^6$ and $R^7$ are independently selected from the group consisting of hydrogen atoms, $C_1$-$C_3$ alkyl groups, allyl groups, propargyl groups and alkyl groups having at least one substituent selected from the group consisting of substituents (a), defined above, or $R^6$ and $R^7$ together represent a group of formula —$(CH_2)_3$—, —$(CH_2)_4$—, —$(CH_2)_5$—, —$(CH_2)_2OCH_2$—, —$(CH_2)_2O(OH_2)_2$—, —$(CH_2)_2NR^8(CH_2)_2$—, wherein:

$R^8$ represents a hydrogen atom, or a methyl, formyl or acetyl group,

—$(CH_2)_2SCH_2$— or —$(CH_2)_2S(CH_2)_2$—, a group of formula —$S(O)_jR^9$, wherein:

j is zero or an integer 1 or 2 and $R^9$ represents a methyl, ethyl or propyl group, a methyl group, an ethyl group or a propyl group; the substituent on the alkyl group in $R^3$ and $R^4$ is a hydroxy, cyano, carbamoyl, carboxy or nitro group, or a fluorine or chlorine atom, or a methoxy, ethoxy, acetyl, formyl, acetoxy, acetylamino, formylamino, methoxycarbonyl or ethoxycarbonyl group, or a group of formula —$NR^{10}R^{11}$, wherein:

$R^{10}$ and $R^{11}$ are independently selected from the group consisting of hydrogen atoms, methyl groups and ethyl groups, a group of formula —$CONR^{12}R^{13}$, wherein:

$R^{12}$ and $R^{13}$ are independently selected from the group consisting of hydrogen atoms, methyl groups and ethyl groups, a group of formula —$SO_2NR^{14}R^{15}$, wherein:

$R^{14}$ and $R^{15}$ are independently selected from the group consisting of hydrogen atoms, methyl groups and ethyl groups, a group of formula —$S(O)_tR^{16}$, wherein:

t is zero or an integer 1 or 2 and $R^{16}$ represents a methyl group, a group of formula —$NHSO_2R^{17}$, wherein:

$R^{17}$ represents a methyl or ethyl group, a group of formula —$N=CR^{18}NR^{19}R^{20}$ or —$NR^{21}CR^{22}=NR^{23}$, wherein:

$R^{18}$ to $R^{23}$ are independently selected from the group consisting of hydrogen atoms, methyl groups and ethyl groups, or a group of formula —$C(=NH)NR^{24}R^{25}$, wherein:

$R^{24}$ and $R^{25}$ and are independently selected from the group consisting of hydrogen atoms, methyl groups and ethyl groups;

$R^3$ and $R^4$ are independently selected from the group consisting of methyl, ethyl, propyl, allyl, propargyl, benzyl and cyclopropylmethyl groups, or together with $R^2$ represent a group of formula —$(CH_2)_2$—, —$(CH_2)_3$—, —$(CH_2)_4$—, —$(CH_2)_5$—, —$(CH_2)$—O—, —$(CH_2)_2$—OCH$_2$—, —$(CH_2)$—O—$(CH_2)_2$—, —$(CH_2)$—$NR^8$—, —$(CH_2)_2$—$NR^8CH_2$—, —$(CH_2)_2$—$NR^8$—$(CH_2)_2$—, wherein:

$R^8$ represents a hydrogen atom or a methyl, ethyl formyl or acetyl group, —$(CH_2)$—S—, —$(CH_2)_2SCH_2$— or —$(CH_2)_2$—S—$(CH_2)_2$—; and where $R^6$ together with $R^7$ represents an alkylene group which is substituted or either $R^3$ or $R^4$ together with $R^2$ represents an alkylene group which is substituted, the substituent is a methyl or ethyl group, a fluorine atom, a hydroxy group or an oxo group.

Of the compounds of the present invention where $R^a$ represents a group of formula (III), we prefer:

(C) those in which:

p is 1, and particularly where the group of formula (III) is a pyrrolidin-2-one-4-yl group, which has the group at its nitrogen atom; and is a hydrogen atom, a $C_1$-$C_4$ alkyl group, more preferably a methyl, ethyl, propyl or butyl group, or a $C_1$-$C_4$ alkanoyl group, more preferably a formyl, acetyl, propionyl or butyryl group, and is most preferably a hydrogen atom, i.e. the pyrrolidin-2-one-4-yl group is unsubstituted.

The compounds of formula (I) can exist in the form of various isomers because of the presence of asymmetric carbon atoms. Both the individual isomers and mixtures of two or more isomers are included in the present invention. Such mixtures may be prepared as a result of the synthesis reactions or by mixing. Where an individual isomer is required, this may be prepared by a stereospecific synthesis route or it may be prepared by separating a mixture of isomers, using separation techniques well known in the art. We particularly prefer those compounds in which the 1-hydroxyethyl group at the 6-penem position is in the same configuration as thienamycin, i.e. it is 1(R)-hydroxyethyl. Also, when $R^1$ represents a hydrogen atom, the (5R, 6S) configuration is preferred, and, when $R^1$ represents a methyl group, the (1R, 5S, 6S) configuration is preferred.

Specific Examples of compounds of the invention are given in the following formulae (I-1) to (I-9), in which the substituents are as defined in the corresponding one of Tables 1 to 9 [i.e. Table 1 relates to formula (I-1), Table 2 relates to formula (I-2) and so on]. In Table 4, where the group represented by Z is asymmetric, the atom attached to the nitrogen atom is shown first. In Table 6, where the group represented by Z' is asymmetric, the atom attached to the nitrogen atom is shown at the end. In Table 7, where the bond to the remainder of the molecule is at the position marked *, that position is occupied by a carbon atom (one of the bonds of which is attached to the remainder of the molecule), and the position marked  is occupied by a $H_2C<$ group; where the bond to the remainder of the molecule is at the position marked , that position is occupied by a $-CH<$ group (one of the bonds of which is attached to the remainder of the molecule), and the position marked * is occupied by a $-CH<$ group. In the Tables, the following abbreviations are used:

| | |
|---|---|
| Ac | acetyl |
| Ada | adamantyl |
| All | allyl |
| Azr | aziridinyl |
| Azt | azetidinyl |
| Bu | butyl |
| cBu | cyclobutyl |
| sBu | sec-butyl |
| tBu | t-butyl |
| Byr | butyryl |
| iByr | isobutyryl |
| Bz | benzyl |
| Car | carbamoyl |
| Dix | 2-oxo-1,3-dioxolen-4-yl |
| Dox | (5-methyl-2-oxo-1,3-dioxolen-4-yl)methyl |
| Et | ethyl |
| Etc | ethoxycarbonyl |
| cHp | cycloheptyl |
| cHx | cyclohexyl |
| Me | methyl |
| Mec | methoxycarbonyl |
| Men | menthyl |
| Mor | morpholino |
| Pdox | (5-phenyl-2-oxo-1,3-dioxolen-4-yl)methyl |
| Ph | phenyl |
| Phth | phthalidyl |
| Pip | piperidyl |
| Piv | pivaloyl |
| Piz | piperazinyl |
| cPn | cyclopentyl |
| Pr | propyl |
| cPr | cyclopropyl |
| iPr | isopropyl |
| Prg | propargyl (= 2-propynyl) |
| Prn | propionyl |
| Pyrd | pyrrolidinyl |
| Tfm | trifluoromethyl |
| Thz | perhydro-1,4-thiazin-4-yl (= thiomorpholino) |

TABLE 2

| Cpd. No. | $R^1$ | $R^3$ | $R^4$ | $l$ |
|---|---|---|---|---|
| 2-1 | Me | Me | Me | 0 |
| 2-2 | H | Me | Me | 0 |
| 2-3 | Me | —CH₂Car | Me | 0 |
| 2-4 | H | —CH₂Car | Me | 0 |
| 2-5 | Me | —CH₂CN | Me | 0 |
| 2-6 | H | —CH₂CN | Me | 0 |
| 2-7 | Me | —CH₂Ac | Me | 0 |
| 2-8 | H | —CH₂Ac | Me | 0 |
| 2-9 | Me | 2-FEt | Me | 0 |
| 2-10 | H | 2-FEt | Me | 0 |
| 2-11 | Me | 2-HOEt | Me | 0 |
| 2-12 | H | 2-HOEt | Me | 0 |
| 2-13 | Me | —CH₂—diMeCar | Me | 0 |
| 2-14 | H | —CH₂—diMeCar | Me | 0 |
| 2-15 | Me | All | Me | 0 |
| 2-16 | H | All | Me | 0 |
| 2-17 | Me | Prg | Me | 0 |
| 2-18 | H | Prg | Me | 0 |
| 2-19 | Me | —CH₂OMe | Me | 0 |
| 2-20 | H | —CH₂OMe | Me | 0 |
| 2-21 | Me | Et | Me | 0 |
| 2-22 | H | Et | Me | 0 |
| 2-23 | Me | —CH₂—MeCar | Me | 0 |
| 2-24 | H | —CH₂—MeCar | Me | 0 |
| 2-25 | Me | 2-CarOEt | Me | 0 |
| 2-26 | H | 2-CarOEt | Me | 0 |
| 2-27 | Me | Mec—CH₂— | Me | 0 |
| 2-28 | H | Mec—CH₂— | Me | 0 |
| 2-29 | Me | Et | Et | 0 |
| 2-30 | H | Et | Et | 0 |

TABLE 3

| Cpd. No. | $R^1$ | $R^3$ | $R^4$ | $m$ | $n$ |
|---|---|---|---|---|---|
| 3-1 | Me | Me | Me | 1 | 3 |
| 3-2 | H | Me | Me | 1 | 3 |
| 3-3 | Me | 2-FEt | Me | 1 | 3 |
| 3-4 | H | 2-FEt | Me | 1 | 3 |
| 3-5 | Me | Et | Me | 1 | 3 |
| 3-6 | H | Et | Me | 1 | 3 |
| 3-7 | Me | —CH₂Car | Me | 1 | 3 |
| 3-8 | H | —CH₂Car | Me | 1 | 3 |
| 3-9 | Me | —CH₂Ac | Me | 1 | 3 |
| 3-10 | H | —CH₂Ac | Me | 1 | 3 |
| 3-11 | Me | Me | Me | 1 | 1 |
| 3-12 | H | Me | Me | 1 | 1 |
| 3-13 | Me | Me | Me | 2 | 3 |
| 3-14 | H | Me | Me | 2 | 3 |
| 3-15 | Me | —CH₂Car | Me | 1 | 1 |
| 3-16 | H | —CH₂Car | Me | 1 | 1 |
| 3-17 | Me | Et | Me | 1 | 1 |
| 3-18 | H | Et | Me | 1 | 1 |
| 3-19 | Me | 2-FEt | Me | 1 | 1 |
| 3-20 | H | 2-FEt | Me | 1 | 1 |
| 3-21 | Me | Et | Et | 1 | 1 |
| 3-22 | H | Et | Et | 1 | 1 |

TABLE 4

| Cpd. No. | $R^1$ | Z |
|---|---|---|
| 4-1 | Me | —(CH₂)₃— |
| 4-2 | H | —(CH₂)₃— |
| 4-3 | Me | —(CH₂)₄— |
| 4-4 | H | —(CH₂)₄— |
| 4-5 | Me | —(CH₂)₂—O—CH₂— |
| 4-6 | H | —(CH₂)₂—O—CH₂— |
| 4-7 | Me | —(CH₂)₂—S—CH₂— |
| 4-8 | H | —(CH₂)₂—S—CH₂— |
| 4-9 | Me | —(CH₂)₂—NMe—CH₂— |
| 4-10 | H | —(CH₂)₂—NMe—CH₂— |
| 4-11 | Me | —(CH₂)₂—NAc—CH₂— |
| 4-12 | H | —(CH₂)₂—NAc—CH₂— |
| 4-13 | Me | —(CH₂)₂—NH—CH₂— |
| 4-14 | H | —(CH₂)₂—NH—CH₂— |
| 4-15 | Me | —(CH₂)₂—NH—CO— |
| 4-16 | H | —(CH₂)₂—NH—CO— |
| 4-17 | Me | —(CH₂)₂—NMe—CO— |
| 4-18 | H | —(CH₂)₂—NMe—CO— |
| 4-19 | Me | —CH₂—CO—NH—CO— |

TABLE 4-continued

| Cpd. No. | R¹ | Z |
|---|---|---|
| 4-20 | H | —CH₂—CO—NH—CO— |
| 4-21 | Me | —CH₂—CHMe—O—CH₂— |
| 4-22 | H | —CH₂—CHMe—O—CH₂— |
| 4-23 | Me | —CH₂—CHMe—CH₂— |
| 4-24 | H | —CH₂—CHMe—CH₂— |
| 4-25 | Me | —(CH₂)₂—CHOH— |
| 4-26 | H | —(CH₂)₂—CHOH— |
| 4-27 | Me | —(CH₂)₂—CHF— |
| 4-28 | H | —(CH₂)₂—CHF— |

TABLE 5

| Cpd. No. | R¹ | R² | R³ | R⁴ | l |
|---|---|---|---|---|---|
| 5-1 | Me | OH | Me | Me | 1 |
| 5-2 | H | OH | Me | Me | 1 |
| 5-3 | Me | F | Me | Me | 1 |
| 5-4 | H | F | Me | Me | 1 |
| 5-5 | Me | —NH₂ | Me | Me | 1 |
| 5-6 | H | —NH₂ | Me | Me | 1 |
| 5-7 | Me | —NHAc | Me | Me | 1 |
| 5-8 | H | —NHAc | Me | Me | 1 |
| 5-9 | Me | MeO | Me | Me | 1 |
| 5-10 | H | MeO | Me | Me | 1 |
| 5-11 | Me | EtO | Me | Me | 1 |
| 5-12 | H | EtO | Me | Me | 1 |
| 5-13 | Me | CarO | Me | Me | 1 |
| 5-14 | H | CarO | Me | Me | 1 |
| 5-15 | Me | CN | Me | Me | 1 |
| 5-16 | H | CN | Me | Me | 1 |
| 5-17 | Me | Car | Me | Me | 1 |
| 5-18 | H | Car | Me | Me | 1 |
| 5-19 | Me | MeCar | Me | Me | 1 |
| 5-20 | H | MeCar | Me | Me | 1 |
| 5-21 | Me | diMeCar | Me | Me | 1 |
| 5-22 | H | diMeCar | Me | Me | 1 |
| 5-23 | Me | Mec | Me | Me | 1 |
| 5-24 | H | Mec | Me | Me | 1 |
| 5-25 | Me | Me | Me | Me | 1 |
| 5-26 | H | Me | Me | Me | 1 |
| 5-27 | Me | Et | Me | Me | 1 |
| 5-28 | H | Et | Me | Me | 1 |
| 5-29 | Me | AcO | Me | Me | 1 |
| 5-30 | H | AcO | Me | Me | 1 |
| 5-31 | Me | —CH₂Ac | Me | Me | 1 |
| 5-32 | H | —CH₂Ac | Me | Me | 1 |
| 5-33 | Me | MeS | Me | Me | 1 |
| 5-34 | H | MeS | Me | Me | 1 |
| 5-35 | Me | MeS(O)— | Me | Me | 1 |
| 5-36 | H | MeS(O)— | Me | Me | 1 |
| 5-37 | Me | MeSO₂— | Me | Me | 1 |
| 5-38 | H | MeSO₂— | Me | Me | 1 |

TABLE 6

| Cpd. No. | R¹ | R³ | R⁴ | Z' | m |
|---|---|---|---|---|---|
| 6-1 | Me | Me | Me | —CH₂O(CH₂)₂— | 0 |
| 6-2 | H | Me | Me | —CH₂O(CH₂)₂— | 0 |
| 6-3 | Me | Me | Me | —O(CH₂)₂— | 1 |
| 6-4 | H | Me | Me | —O(CH₂)₂— | 1 |
| 6-5 | Me | Me | Me | —CH₂S(CH₂)₂— | 0 |
| 6-6 | H | Me | Me | —CH₂S(CH₂)₂— | 0 |
| 6-7 | Me | Me | Me | —S(CH₂)₂— | 1 |
| 6-8 | H | Me | Me | —S(CH₂)₂— | 1 |
| 6-9 | Me | Me | Me | —CH₂NMe(CH₂)₂— | 0 |
| 6-10 | H | Me | Me | —CH₂NMe(CH₂)₂— | 0 |
| 6-11 | Me | Me | Me | —CH₂NAc(CH₂)₂— | 0 |
| 6-12 | H | Me | Me | —CH₂NAc(CH₂)₂— | 0 |
| 6-13 | Me | Me | Me | —NAc(CH₂)₂— | 1 |
| 6-14 | H | Me | Me | —NAc(CH₂)₂— | 1 |

TABLE 7

| Cpd. No. | R¹ | R³ | Z'' | m | position of bond |
|---|---|---|---|---|---|
| 7-1 | Me | Me | —(CH₂)₂— | 2 | * |
| 7-2 | H | Me | —(CH₂)₂— | 2 | * |
| 7-3 | Me | Me | —CH₂— | 3 | * |
| 7-4 | H | Me | —CH₂— | 3 | * |
| 7-5 | Me | Me | —(CH₂)₂— | 2 | ** |
| 7-6 | H | Me | —(CH₂)₂— | 2 | ** |
| 7-7 | Me | Et | —(CH₂)₂— | 2 | * |
| 7-8 | H | Et | —(CH₂)₂— | 2 | * |
| 7-9 | Me | 2-FEt | —(CH₂)₂— | 2 | * |
| 7-10 | H | 2-FEt | —(CH₂)₂— | 2 | * |

TABLE 8

| Cpd. No. | R³ | R⁵ | p |
|---|---|---|---|
| 8-1 | H | Na | 2 |
| 8-2 | H | Dox | 2 |
| 8-3 | H | Na | 1 |
| 8-4 | H | PivO—CH₂— | 1 |
| 8-5 | H | —CH₂O—CO—(1-Me—cHx) | 1 |
| 8-6 | H | —CH(Me)O—CO—O—cPn | 1 |
| 8-7 | H | —CH(Me)O—CO—O—iPr | 1 |
| 8-8 | H | —CH(Me)O—CO—O—Men | 1 |
| 8-9 | H | —CH(Me)O—CO—O—CH₂cHx | 1 |
| 8-10 | H | —CH(Me)O—CO—O—cHx | 1 |
| 8-11 | H | —CH(Me)O—CO—cHx | 1 |
| 8-12 | H | —CH₂OAc | 1 |
| 8-13 | H | 1-EtcOEt | 1 |
| 8-14 | H | 1-PivOEt | 1 |
| 8-15 | H | Dox | 1 |
| 8-16 | H | Phth | 1 |
| 8-17 | Me | PivO—CH₂— | 1 |
| 8-18 | Me | —CH₂O—CO—(1-Me—cHx) | 1 |
| 8-19 | Me | —CH(Me)O—CO—O—cPn | 1 |
| 8-20 | Me | —CH(Me)O—CO—O—iPr | 1 |
| 8-21 | Me | —CH(Me)O—CO—O—CH₂cHx | 1 |
| 8-22 | Me | —CH(Me)O—CO—O—cHx | 1 |
| 8-23 | Me | —CH(Me)O—CO—cHx | 1 |
| 8-24 | Me | —CH₂OAc | 1 |
| 8-25 | Me | 1-EtcOEt | 1 |
| 8-26 | Me | 1-PivOEt | 1 |
| 8-27 | Me | Dox | 1 |
| 8-28 | Me | Phth | 1 |
| 8-29 | H | Na | 3 |
| 8-30 | H | PivO—CH₂— | 3 |
| 8-31 | H | 1-EtcOEt | 3 |
| 8-32 | H | Dox | 3 |
| 8-33 | H | Phth | 3 |
| 8-34 | H | PivO—CH₂— | 2 |
| 8-35 | H | 1-EtcOEt | 2 |

TABLE 9

| Cpd. No. | R³ | R⁵ |
|---|---|---|
| 9-1 | H | Na |
| 9-2 | H | PivO—CH₂— |
| 9-3 | H | —CH₂O—CO—(1-Me—cHx) |
| 9-4 | H | —CH₂O—CO—O—Men |
| 9-5 | H | —CH(Me)O—CO—cPn |
| 9-6 | H | —CH(Me)O—CO—O—iPr |
| 9-7 | H | —CH(Me)O—CO—O—Men |
| 9-8 | H | —CH(Me)O—CO—O—CH₂—cHx |
| 9-9 | H | —CH(Me)O—CO—O—cHx |
| 9-10 | H | —CH(Me)O—CO—O—tBu |
| 9-11 | H | —CH(Me)O—CO—cHx |
| 9-12 | H | 1-PivOEt |
| 9-13 | H | —CH₂OAc |
| 9-14 | H | 1-EtcOEt |
| 9-15 | H | —CH(Me)O—CO—O—CHEt₂ |
| 9-16 | H | —CH(Me)O—CO—O—CPr₃ |
| 9-17 | H | —CH(Me)O—CO—O—cHP |
| 9-18 | H | Dox |
| 9-19 | H | Phth |
| 9-20 | H | Pdox |
| 9-21 | H | 1-AcOEt |
| 9-22 | H | 1-iByrOEt |

TABLE 9-continued

| Cpd. No. | R³ | R⁵ |
|---|---|---|
| 9-23 | H | —CH₂O—CO—(1-Me—cPn) |
| 9-24 | H | 1-MecOEt |
| 9-25 | H | —CH(Me)O—CO—O—Ada |
| 9-26 | Me | PivO—CH₂— |
| 9-27 | Me | —CH₂O—CO—(1-Me—cHx) |
| 9-28 | Me | —CH(Me)O—CO—O—cPn |
| 9-29 | Me | —CH(Me)O—CO—O—iPr |
| 9-30 | Me | —CH(Me)O—CO—O—Men |
| 9-31 | Me | —CH(Me)O—CO—O—CH₂—cHx |
| 9-32 | Me | —CH(Me)O—CO—O—cHx |
| 9-33 | Me | —CH(Me)O—CO—cHx |
| 9-34 | Me | —CH₂OAc |
| 9-35 | Me | 1-EtcOEt |
| 9-36 | Me | 1-PivOEt |
| 9-37 | Me | Dox |
| 9-38 | Me | Na |
| 9-39 | Me | Phth |
| 9-40 | Ac | PivO—CH₂— |
| 9-41 | Ac | 1-EtcOEt |
| 9-42 | Ac | Dox |
| 9-43 | Ac | Phth |
| 9-44 | Et | PivO—CH₂— |
| 9-45 | Et | 1-EtcOEt |
| 9-46 | Et | Dox |
| 9-47 | Et | Na |
| 9-48 | Ac | Na |
| 9-49 | H | —CH(Me)O—CO—O—sBu |
| 9-50 | H | 1-AcOEt |
| 9-51 | H | —CH₂O—CO—O—CH₂—cPr |
| 9-52 | H | —CH₂O—CO—O—CH₂—cBu |
| 9-53 | H | —CH(Me)O—CH—O—CH₂—cPn |
| 9-54 | H | 2-oxo-4,5,6,7-tetrahydro-1,3-benzodioxolen-4-yl |
| 9-55 | H | 5-iPr—Dix—CH₂— |
| 9-56 | H | 5-tBu—Dix—CH₂— |
| 9-57 | H | 1-(5-Me—Dix)Et |
| 9-58 | H | 1-(iPrO—CO—O—)Et |
| 9-59 | H | 2-Me-1-(iPrO—CO—O—)Pr |
| 9-60 | H | 2-(iPrO—CO—O—)Pr |
| 9-61 | H | 1-PivOPr |
| 9-62 | H | 2-Me-1-PivOPr |
| 9-63 | H | 2-PivOPr |
| 9-64 | H | 1-(1-MecHx—CO—O—)Pr |
| 9-65 | H | 2-Me-1-(1-MecHx—CO—O—)Pr |
| 9-66 | H | 2-(1-MecHx—CO—O—)Pr |
| 9-67 | H | 1-(cHx—CO—O—)Pr |
| 9-68 | H | 2-Me-1-(cHx—CO—O—)Pr |
| 9-69 | H | (cHx—AcO)—CH₂— |
| 9-70 | H | 1-(cHx—AcO)Et |
| 9-71 | H | 1-(cHx—AcO)Pr |
| 9-72 | H | 2-Me-1-(cHx—AcO)Pr |
| 9-73 | H | 1-iByrOEt |
| 9-74 | H | 1-iByrOPr |
| 9-75 | H | (cPn—CO—O—)CH₂— |
| 9-76 | H | 1-(cPn—CO—O—)Et |
| 9-77 | H | 1-(cPn—CO—O—)Pr |
| 9-78 | H | 2-Me-1-(cPn—CO—O—)Pr |
| 9-79 | H | 1-AcOPr |
| 9-80 | H | 1-AcO-2-MePr |
| 9-81 | H | PrnO—CH₂— |
| 9-82 | H | 1-PrnOEt |
| 9-83 | H | 1-PrnOPr |
| 9-84 | H | 1-(1-MecPn—CO—O—)Et |
| 9-85 | H | 1-(1-MecPn—CO—O—)Pr |
| 9-86 | H | 2-AcOPr |
| 9-87 | H | ByrO—CH₂— |
| 9-88 | H | 1-ByrOEt |
| 9-89 | H | iPrO.CO.OCH₂— |
| 9-90 | H | cPnO.CO.OCH₂— |
| 9-91 | H | cHxO.CO.OCH₂— |
| 9-92 | H | tBuO.CO.OCH₂— |
| 9-93 | H | EtO.CO.OCH₂— |
| 9-94 | H | MeO.CO.OCH₂— |
| 9-95 | Me | cHx.CO.OCH₂— |
| 9-96 | Me | cPnO.CO.OCH₂— |
| 9-97 | Me | cHxO.CO.OCH₂— |
| 9-98 | Me | iPrO.CO.OCH₂— |
| 9-99 | Me | iByrOCH₂— |
| 9-100 | Me | 1-(iByrO)Et |
| 9-101 | Me | 1-(cPn.CO.O)Et |
| 9-102 | Me | cPn.CO.OCH₂— |
| 9-103 | H | cHx.CO.OCH₂— |

Of the compounds listed above, the following are preferred, that is to say Compounds No. 1-1, 1-2, 1-9, 1-23, 1-267, 1-269, 1-275, 9-2, 9-3, 9-5, 9-6 and 9-8, of which the following are most preferred:

1-1. 2-(2-Carbamoyl-1,1-dimethylpyrrolidinium-4-ylthio)-6-(1-hydroxyethyl)-1-methyl-1-carbapen-2-em-3-carboxylate, especially its (1R, 5S, 6S)-2-[(2S, 4S)-2-carbamoyl-1,1-dimethylpyrrolidinium-4-ylthio]-6-[(1R)-1-hydroxyethyl]-1-methyl-1-carbapen-2-em-3-carboxylate isomer;

1-2. 2-(2-Carbamoyl-1,1-dimethylpyrrolidinium-4-ylthio)-6-(1-hydroxyethyl)-1-carbapen-2-em-3-carboxylate, especially its (5R, 6S)-2-[(2S, 4S)-2-carbamoyl-1,1-dimethylpyrrolidinium-4-ylthio]-6-[(1R)-1-hydroxyethyl]-1-carbapen-2-em-3-carboxylate isomer;

1-23. 2-(1,1-Dimethyl-2-dimethylcarbamoylpyrrolidinium-4-ylthio)-6-(1-hydroxyethyl)-1-methyl-1-carbapen-2-em-3-carboxylate, especially its (1R, 5S, 6S)-2-[(2S, 4S)-1,1-dimethyl-2-dimethylcarbamoylpyrrolidinium-4-ylthio]-6-[(1R)-1-hydroxyethyl]-1-methyl-1-carbapen-2-em-3-carboxylate isomer;

1-267. 2-(1,1-Dimethyl-2-ethylcarbamoylpyrrolidinium-4-ylthio)-6-(1-hydroxyethyl)-1-methyl-1-carbapen-2-em-3-carboxylate, especially its (1R, 5S, 6S)-2-[(2S, 4S)-1,1-dimethyl-2-ethylcarbamoylpyrrolidinium-4-ylthio]-6-[(1R)-1-hydroxyethyl]-1-methyl-1-carbapen-2-em-3-carboxylate isomer;

1-275. 2-(2-Cyclopropylcarbamoyl-1,1-dimethylpyrrolidinium-4-ylthio)-6-(1-hydroxyethyl)-1-methyl-1-carbapen-2-em-3-carboxylate, especially its (1R, 5S, 6S)-2-[(2S, 4S)-2-cyclopropylcarbamoyl-1,1-dimethylpyrrolidinium-4-ylthio]-6-[(1R)-1-hydroxyethyl]-1-methyl-1-carbapen-2-em-3-carboxylate isomer;

9-2. pivaloyloxymethyl 2-(2-oxo-4-pyrrolidinylthio)-6-(1-hydroxyethyl)-1-methyl-1-carbapen-2-em-3-carboxylate, especially its pivaloyloxymethyl (1R, 5S, 6S)-2-(2-oxo-4-pyrrolidinylthio)-6-[(1R)-1-hydroxyethyl]-1-methyl-1-carbapen-2-em-3-carboxylate isomer;

9-3. (1-Methylcyclohexan-1-yl)carbonyloxymethyl 2-(2-oxo-4-pyrrolidinylthio)-6-(1-hydroxyethyl)-1-methyl-1-carbapen-2-em-3-carboxylate, especially its (1-methylcyclohexan-1-yl)carbonyloxymethyl (1R, 5S, 6S)-2-(2-oxo-4-pyrrolidinylthio)-6-[(1R)-1-hydroxyethyl]-1-methyl-1-carbapen-2-em-3-carboxylate isomer;

9-5. 1-(Cyclopentyloxycarbonyloxy)ethyl 2-(2-oxo-4-pyrrolidinylthio)-6-(1-hydroxyethyl)-1-methyl-1-carbapen-2-em-3-carboxylate, especially its 1-(cyclopentyloxycarbonyloxy)ethyl (1R, 5S, 6S)-2-(2-oxo-4-pyrrolidinylthio)-6-[(1R)-1-hydroxyethyl]-1-methyl-1-carbapen-2-em-3-carboxylate isomer;

and pharmaceutically acceptable salts thereof.

The compounds of the present invention can be prepared by a variety of methods well known for preparing this type of compound. For example, in general terms, the compounds may be prepared by reacting a compound of formula (IV):

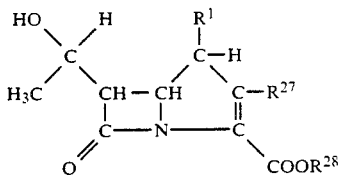

(in which R[1] is as defined above, R[27] represents a group of formula —OR[29] or —SO—R[30], in which:

R[29] represents an alkanesulfonyl group, an arylsulfonyl group, a dialkylphosphoryl group, or a diarylphosphoryl group; and R[30] represents an alkyl group, a haloalkyl group, a 2-acetylaminoethyl group, a 2-acetylaminovinyl group; an aryl group or a heteroaryl group (i.e. an aromatic heterocyclic group); and R[28] represents a protecting group for a carboxylic acid);

with a compound of formula (Va):

or with a compound of formula (Vb):

[in which $R^{II}$ represents said group of formula (II), in which, if required any active groups are protected, $R^{III}$ represents said group of formula (III), in which, if required any active groups are protected, l is as defined above, and $X^-$ is a balancing anion], to give a compound of formula (VI):

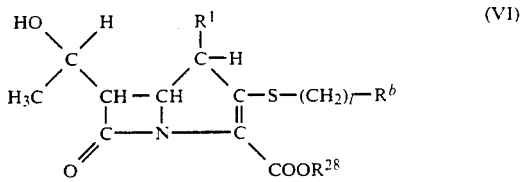

[in which R[1], R[28] and l are as defined above, and $R^b$ represents said group of formula (II) or (III), in which, if required any active groups are protected, and which, if necessary contains a balancing anion], and then, if necessary, removing protecting groups and/or esterifying and/or salifying the resulting compound to give a compound of formula (I) or a pharmaceutically acceptable salt or ester thereof.

In the above formulae, R[29] represents: an alkanesulfonyl group, such as a methanesulfonyl, ethanesulfonyl, propanesulfonyl, isopropanesulfonyl or butanesulfonyl group; an arylsulfonyl group, such as a phenylsulfonyl, tolylsulfonyl, especially p-tolylsulfonyl, or naphthylsulfonyl group; a dialkylphosphoryl group, such as a dimethylphosphoryl, diethylphosphoryl, dipropylphosphoryl, diisopropylphosphoryl, dibutylphosphoryl or dipentylphosphoryl group; or a diarylphosphoryl group, such as a diphenylphosphoryl or ditolylphosphoryl group;

R[30] represents an alkyl group, such as methyl, ethyl, propyl or isopropyl group; a haloalkyl group, such as a fluoromethyl, chloromethyl, fluoroethyl, difluoromethyl, difluoroethyl, dichloroethyl, trifluoromethyl or trifluoroethyl group; a 2-acetylaminoethyl group; a 2-acetylaminovinyl group; an aryl group, such as a phenyl or naphthyl group which may optionally be substituted with from 1 to 3 substituents, which may be the same or different and examples of the substituent include the fluorine, chlorine and bromine atoms, and the methyl, ethyl, propyl, isopropyl, methoxy, ethoxy, propoxy, isopropoxy, methoxycarbonyl, ethoxycarbonyl, t-butoxycarbonyl, nitro, hydroxy and cyano groups; a heteroaryl group such as a pyridyl or pyrimidinyl group which may optionally be substituted with from 1 to 3 substituents, which may be the same or different and examples of the substituent include the fluorine, chlorine and bromine atoms and the methyl, ethyl, propyl and isopropyl groups; and R[28] represents a protecting group for a carboxylic acid, examples of the protecting group include, for example an alkyl group such as a methyl, ethyl or t-butyl group; an aralkyl group such as a benzyl, diphenylmethyl, 4-nitrobenzyl or 2-nitrobenzyl group; an alkenyl group such as an allyl, 2-chloroallyl or 2-methylallyl group; a haloalkyl group such as a 2,2,2-trichloroethyl, 2,2-dibromoethyl or 2,2,2-tribromoethyl group or a 2-trimethylsilylethyl group.

In more detail, the compounds may be prepared as illustrated in the following Methods A and B.

Method A:

This is as shown in the following Reaction Scheme A:

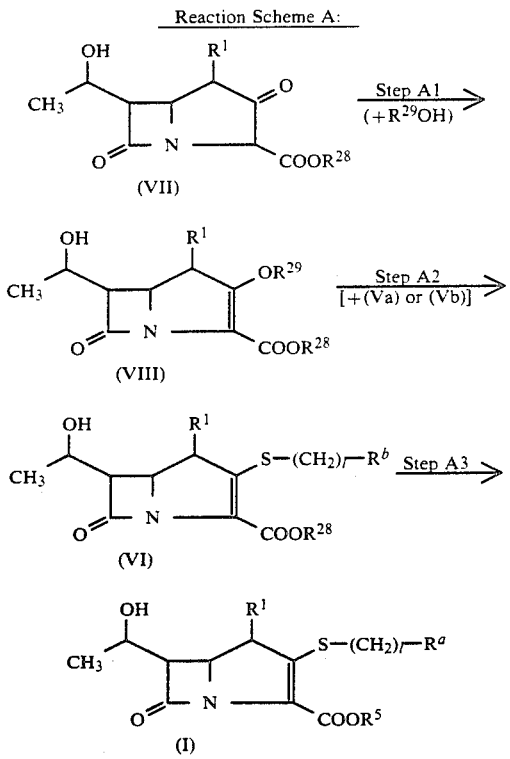

In the above formulae: R[1], R[5], $R^a$, $R^b$, R[28], R[29], and l are as defined above.

In the compound of formula (Va), $X^-$ represents a balancing anion, which is preferably a halogen atom (e.g. a chlorine, bromine or iodine atom) or an alkylsulfonyloxy, arylsulfonyloxy or halosulfonyloxy group (e.g. a methanesulfonyloxy, p-toluenesulfonyloxy, trifluoromethanesulfonyloxy or fluorosulfonyloxy group).

In Step A1 of this reaction scheme, the compound of formula (VII), which is the starting material, is reacted with an active derivative of an alkanesulfonic, arylsulfonic, dialkylphosphoric or diarylphosphoric acid $R^{29}OH$, e.g. an alkanesulfonic or arylsulfonic acid anhydride or a dialkylphosphoryl or diarylphosphoryl halide in the presence of a base. In Step A2, the resulting compound of formula (VIII) is then reacted without isolation with a mercaptan derivative of formula (Va) or (Vb) in the presence of a base to give a compound of formula (VI). The desired compound of formula (I) may then be prepared, if necessary, by removal of the protecting group, $R^{28}$, from the carboxyl group in the compound of formula (VI).

In Step A1, examples of the reactive derivative of the reagent of formula $R^{29}OH$ which may be employed include: alkanesulfonic acid anhydrides, such as methanesulfonic or ethanesulfonic acid anhydride; arylsulfonic acid anhydrides, such as benzenesulfonic or p-toluenesulfonic acid anhydride; dialkylphosphoryl halides, such as dimethylphosphoryl or diethylphosphoryl chloride; diarylphosphryl halides, such as diphenylphosphoryl chloride or diphenylphosphoryl bromide. Of these reagents, p-toluenesulfonic acid anhydride or diphenylphosphoryl chloride is preferred. There is no particular restriction on the nature of the solvent to be employed, provided that it has no adverse effect on the reaction or on the reagents involved. Examples of suitable solvents include: halogenated hydrocarbons, especially halogenated aliphatic hydrocarbons, such as methylene chloride, 1,2-dichloroethane or chloroform; nitriles such as acetonitrile; amides such as N,N-dimethylformamide or N,N-dimethylacetamide. There is likewise no particular limitation on the nature of the base to be employed, provided that it has no adverse effect upon other parts of the molecule, particularly the $\beta$-lactam ring, preferred bases which may be employed in this reaction include such organic bases as triethylamine, diisopropylethylamine or 4-dimethylaminopyridine.

The reaction can take place over a wide range of temperatures, and the precise reaction temperature is not critical to the invention. In general, we find it convenient to carry out the reaction at a relatively low temperature in order to prevent side reactions, usually at a temperature from $-20°$ C. to $40°$ C. The time required for the reaction may also vary widely, depending on many factors, notably the reaction temperature and the nature of the reagents. However, provided that the reaction is effected under the preferred conditions outlined above, a period of from 10 minutes to 5 hours will usually suffice.

It is not necessary to isolate the resulting compound of formula (VIII) before the next step in the reaction scheme. Thus, in Step A2, the reaction mixture may be treated with a mercaptan derivative of formula (Va) or (Vb) in the presence of a base. The nature of the base to be employed in the reaction is not critical but preferred bases include organic bases, such as triethylamine or diisopropylamine, and inorganic bases, such as potassium carbonate or sodium carbonate.

The reaction can take place over a wide range of temperatures, and the precise reaction temperature is not critical to the invention. In general, however, we find it best to carry out the reaction at a relatively low temperature, e.g. at a temperature from $-20°$ C. to room temperature. The time required for the reaction may also vary widely, depending on many factors, notably the reaction temperature and the nature of the reagents. However, provided that the reaction is effected under the preferred conditions outlined above, a period of from 30 minutes to 5 days will usually suffice.

After completion of the reaction, the desired compound of formula (VI) may be recovered from the reaction mixture by conventional means, for example, one suitable recovery procedure comprises simply distilling off the solvent from the reaction mixture. The resulting compound may be further purified, if necessary, by conventional means, for example by recrystallization, reprecipitation or the various chromatography techniques, such as column chromatography or preparative thin layer chromatography.

If desired, before or after such further purification, the carboxy-protecting group may be removed. This is preferably effected without isolation of the compound of formula (VI).

The final reaction step of process A comprises the removal of the carboxy-protecting group $R^{28}$ from the compound of formula (VI), to give the corresponding carboxylic acid of formula (I), and, if required, conversion of the resulting free acid to another salt or ester. This step is optional, and it will be appreciated that the removal of the carboxy-protecting group may not always be necessary or desired, for example when the compound of formula (VI) is a pharmaceutically acceptable ester within the scope of the present invention. If it is desired to remove the carboxy-protecting group, this may be done by the use of conventional methods, the choice of which will depend upon the nature of the protecting group employed.

If the protecting group is removable by reduction, for example if it is a haloalkyl group, an aralkyl group or a benzhydryl group, it may be removed by contact with a reducing agent. In the case of haloalkyl groups, such as the 2,2-dibromoethyl or 2,2,2-trichloroethyl groups, the preferred reducing agent is a combination of zinc with acetic acid. If the protecting group is an aralkyl group (such as a benzyl or p-nitrobenzyl group) or a benzhydryl group, it is preferred to remove it either by catalytic reduction using hydrogen and a suitable catalyst, such as platinum or palladium on carbon; or by reduction with an alkali metal sulfide, such as sodium sulfide or potassium sulfide. Whatever the reduction technique, the reduction process is preferably effected in the presence of a solvent, the nature of which is not critical, provided that it has no adverse effect upon the reaction. Suitable solvents include alcohols (such as methanol or ethanol), ethers (such as tetrahydrofuran or dioxane), aliphatic carboxylic acids (such as acetic acid), or a mixture of one or more of these organic solvents with water. The reaction temperature is not critical but will normally be in the range from $0°$ C. to room temperature. The time required for the reaction will vary, depending upon the nature of the starting materials and reducing agents, as well as upon the reaction temperature, but a period of from 5 minutes to 12 hours will normally suffice.

After completion of the reaction, the desired compound, which will contain a free carboxy group, may be recovered by conventional means from the reaction mixture. For example, a suitable recovery technique comprises: separating off any insolubles; and then distilling off the solvent to give the desired product. This may, if necessary, be further purified by conventional means, for example recrystallization or the various chromatography techniques, such as preparative thin layer chromatography or column chromatography.

If desired, a carboxy group in the compound prepared as described above can be converted to an ester group hydrolysable under physiological conditions. This may be effected by conventional means. If $R^5$ represents an ester which is hydrolysable under physiological conditions, e.g. a pivaloyloxymethyl, acetoxymethyl, phthalidyl, indanyl, methoxymethyl or 2-oxo-5-methyl-1,3-dioxolen-4-ylmethyl group, the compounds of formula (I) can be hydrolyzed in vivo under physiological conditions. Accordingly such a compound may be administered directly to a patient without deprotection.

Method B:

This is as shown in the following Reaction Scheme B:

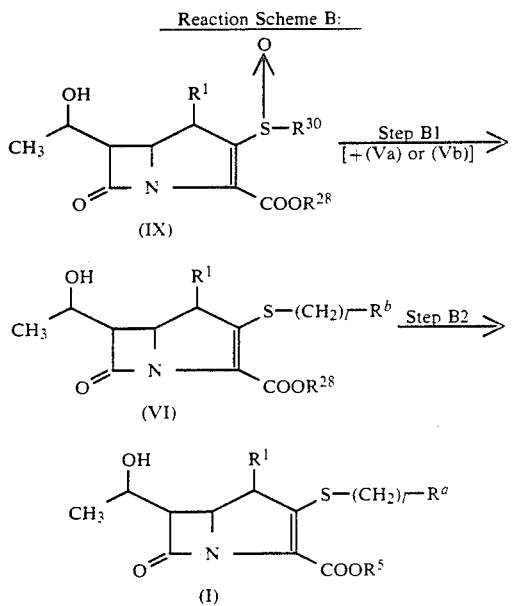

In the above formulae $R^1$, $R^a$, $R^b$, $R^{28}$, $R^{30}$ and $l$ are as defined above.

The compounds of formula (IX) used as starting materials in this reaction scheme can be prepared as described in Japanese patent Application Kokai No. Sho 62-30781.

In Step B1, the compound of formula (VI) can be prepared by reacting a compound of formula (IX) with a mercaptan compound of formula (Va) or (Vb) in the presence of a base and in an inert solvent. There is no particular restriction on the nature of the solvent to be employed, provided that it has no adverse effect on the reaction or on the reagents involved. Examples of suitable solvents include: ethers, such as tetrahydrofuran; nitriles, such as acetonitrile; fatty acid amides, such as dimethylformamide; sulfoxides, such as dimethyl sulfoxide; water; or a mixture of any two or more thereof. The base used in the reaction is likewise not critical, provided that it does not affect other parts of the molecule, particularly the β-lactam ring. Examples of suitable bases include: organic bases, such as diisopropylethylamine, triethylamine, N-methylpiperidine or 4-(N,N-dimethylamino)pyridine; and inorganic bases, particularly alkali metal carbonates, such as potassium carbonate or sodium bicarbonate. The reaction can take place over a wide range of temperatures, and the precise reaction temperature is not critical to the invention, although we prefer that the reaction is carried out at relatively low temperature in order to prevent side reactions. In general, we find it convenient to carry out the reaction at a temperature from $-20°$ C. to $40°$ C. The time required for the reaction may also vary widely, depending on many factors, notably the reaction temperature and the nature of the reagents. However, provided that the reaction is effected under the preferred conditions outlined above, a period of from 5 minutes to 5 days will usually suffice.

After completion of the reaction, the desired compound of formula (VI) can be recovered from the reaction mixture by conventional means. Also, the compounds of formula (I) can, if necessary, be prepared by deprotection of a compound of formula (VI) using the procedure described in Method A. Further separation and purification of the resulting compound may be effected as described in Method A.

Compounds of formula (Va) and (Vb), which are also starting materials in the above reaction schemes may be obtained by conventional and well known means for preparing this type of compound. In the case of those compounds of formula (Vb), where these are not otherwise available, they may be prepared as follows:

First, a compound of formula (X):

$$L-R^c \qquad (X)$$

[in which L represents a leaving group, such as a hydroxy group, a halogen atom (such as a chlorine, bromine or iodine atom) or a sulfonyloxy group (e.g. a methanesulfonyloxy, propanesulfonyloxy, trifluoromethanesulfonyloxy or toluenesulfonyloxy group) and $R^c$ represents a 2-oxopyrrolidinyl group, as defined in relation to the group of formula (III)] is converted to the corresponding protected thio compound of formula (XI):

$$R^d-R^c \qquad (XI)$$

[in which $R^d$ represents a thio-protecting group such as an alkanoyl group (e.g. an acetyl or propionyl group) or an aralkyl group (e.g. a 4-methoxybenzyl, 3,4-dimethoxybenzyl, benzhydryl, triphenylmethyl or di(4-methoxyphenyl)methyl group)].

When L represents a hydroxy group, this may be performed by means of the Mitsunobu reaction, which may be performed under conditions known per se, in the presence of diethyl azodicarboxylate, triphenyl phosphine and thioacetic acid.

When L represents a halogen atom or a sulfonyloxy group, the reaction may be performed by reacting the compound of formula (X) with a sodium or potassium salt of $R^d$-SH.

The second step is a conventional hydrolysis reaction and may be performed under conditions known per se. For example, when $R^d$ is an alkanoyl group, it may be removed under alkaline or acidic conditions, for example, with sodium hydroxide in aqueous methanol. When $R^d$ is an aralkyl group, it may be removed, e.g. with trifluoromethanesulfonic acid in the presence of trifluoroacetic acid and anisole.

The mercaptan compound of formula (Va) may be prepared as illustrated in the following Reaction Scheme C:

Reaction Scheme C:

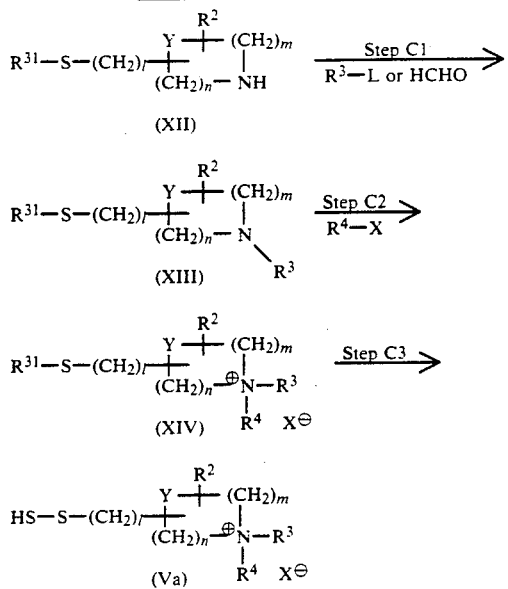

In the above formulae, $R^{31}$ represents a mercapto-protecting group, such as an aralkyl group [e.g. a 4-methoxybenzyl, triphenylmethyl, benzhydryl, 3,4-dimethoxybenzyl or di(4-methoxyphenyl)methyl group], an alkanoyl group (e.g. an acetyl, propionyl or pivaloyl group) or an aromatic acyl group (e.g. an o- or p-toluoyl group or a benzoyl group); L represents a leaving group, such as a halogen atom (e.g. a chlorine, fluorine or iodine atom) or a sulfonyloxy group (e.g. a methanesulfonyloxy, toluenesulfonyloxy, trifluoromethanesulfonyloxy or fluorosulfonyloxy group); and $R^2$, $R^3$, $R^4$, l, m, n and $X^-$ are as defined above.

The compound of formula (XII) used as the starting material in this reaction scheme may be prepared by known methods, for example, as described in Japanese patent Application Kokai No. Sho 60-233076.

In Step C1, a compound of formula (XIII) is prepared by reacting the compound of formula (XII) with a compound of formula $R^3$-L (XV) in the presence of a base. Alternatively, where $R^3$ is a methyl group, the compound of formula (XII) is reacted with formaldehyde (normally in the form of formalin or paraformaldehyde) and then with sodium cyanoborohydride; or it may be reacted with formaldehyde and the reaction product may then be subjected to catalytic hydrogenation with palladium-on-charcoal; or it may be reacted with formaldehyde and formic acid, with heating.

The reaction is preferably carried out in the presence of an inert solvent. There is no particular restriction on the nature of the solvent to be employed, provided that it has no adverse effect on the reaction or on the reagents involved. Examples of suitable solvents include: amides, especially fatty acid amides, such as N,N-dimethylformamide or N,N-dimethylacetamide; halogenated hydrocarbons, especially halogenated aliphatic hydrocarbons, such as methylene chloride, 1,2-dichloroethane or chloroform; ethers such as tetrahydrofuran, dioxane or diethyl ether; nitriles such as acetonitrile; and mixtures of any one or more of these solvents with water.

The reaction can take place over a wide range of temperatures, and the precise reaction temperature is not critical to the invention. In general, we find it convenient to carry out the reaction at a temperature from −20° C. to 100° C., but the reaction is preferably effected at a relatively low temperature, in order to avoid side reactions. The time required for the reaction may also vary widely, depending on many factors, notably the reaction temperature and the nature of the reagents. However, provided that the reaction is effected under the preferred conditions outlined above, a period of from 10 minutes to 2 days will usually suffice.

In Step 2 of this reaction scheme, the compound of formula (XIII) is reacted with a compound of formula $R^4$-X (XVI). The reaction is preferably carried out in the presence of an inert solvent. There is no particular restriction on the nature of the solvent to be employed, provided that it has no adverse effect on the reaction or on the reagents involved. Examples of suitable solvents include: aromatic hydrocarbons, such as benzene, toluene or xylene; halogenated hydrocarbons, especially halogenated aliphatic hydrocarbons, such as methylene chloride, 1,2-dichloroethane or chloroform; amides, especially fatty acid amides, such as N,N-dimethylformamide or N,N-dimethylacetamide; ethers such as tetrahydrofuran, dioxane or diethyl ether; nitriles such as acetonitrile; and mixtures of any one or more of these solvents with water.

The reaction can take place over a wide range of temperatures, and the precise reaction temperature is not critical to the invention. In general, we find it convenient to carry out the reaction at a temperature from −20° C. to 180° C., but the reaction is preferably effected at a relatively low temperature, in order to avoid side reactions. The time required for the reaction may also vary widely, depending on many factors, notably the reaction temperature and the nature of the reagents. However, provided that the reaction is effected under the preferred conditions outlined above, a period of from 10 minutes to 3 days will usually suffice.

In Step C3 of the reaction scheme, the compound of formula (XIV), prepared as described in Step C2, is deprotected to afford a compound of formula (Va).

The method of deprotection will vary, depending on the nature of the protecting group $R^{31}$. Thus, where $R^{31}$ is an aralkyl group, the deprotection may conveniently be carried out by reacting the compound of formula (XIV) with trifluoromethanesulfonic acid in the presence of trifluoroacetic acid and anisole.

On the other hand, where $R^{31}$ is an alkanoyl group or an aromatic acyl group, the deprotection may conveniently be carried out by treating the compound of formula (XIV) with hydrogen chloride or hydrogen bromide in a suitable solvent such as an alcohol (e.g. methanol or ethanol), water or an aqueous ether (e.g. aqueous tetrahydrofuran or aqueous diethyl ether).

The reaction can take place over a wide range of temperatures, and the precise reaction temperature is not critical to the invention. In general, we find it convenient to carry out the reaction at a temperature from −20° C. to 200° C., but the reaction is preferably effected at a relatively low temperature, in order to avoid side reactions. The time required for the reaction may also vary widely, depending on many factors, notably the reaction temperature and the nature of the reagents. However, provided that the reaction is effected under the preferred conditions outlined above, a period of from 10 minutes to 24 hours will usually suffice.

After completion of the reaction, the desired compound of formula (Va) may be recovered from the reaction mixture by conventional means, for example, simply by distilling the solvent from the reaction mixture. The desired compound may be further purified, if necessary, by conventional means such as reprecipitation or the various chromatographic techniques, such as column chromatography or preparative thin layer chromatography.

In the compound of formula (Va), the counteranion $X^-$ will vary, depending on the nature of the reagent employed in Step C3.

The compounds of the present invention exhibit outstanding antibacterial activity with a wide spectrum of activity, and they are also resistant to β-lactamase. As assessed by the agar plate dilution method, they have been shown to be active against a wide range of pathogenic microorganisms, including both Gram-positive bacteria (such as *Staphylococcus aureus* and *Bacillus subtilis*) and Gram-negative bacteria (such as *Escherichia coli, Shigella flexneri, Klebsiella pneumoniae, Proteus vulgaris,* Serratia species e.g. *Serratia marcescens,* Enterobacter species e.g. *Enterobacter cloacae, Salmonella enteritidis* and *Pseudomonas aeruginosa*) and are thus very useful for the treatment of diseases caused by such microorganisms in humans and non-human animals. Whereas thienamycin and its analogs are inactivated in vivo in mammals by dehydropeptidase I, the compounds of the invention are much more stable to this enzyme and exhibit good urinary recovery, and thus possess good biological activity. They also exhibit low toxicity when tested in laboratory animals.

Table 10 sets out the activities of several of the compounds of the present invention against various bacteria, in terms of their minimal inhibitory concentrations (μg/ml).

TABLE 10

| Cpd of Example | Microorganism | | |
|---|---|---|---|
| | A | B | C |
| 1 | 0.01* | 0.05 | 1.5 |
| 4 | 0.05 | 0.1 | 0.8 |
| 16 | 0.01* | 0.05 | 1.5 |
| 20 | 0.02 | 0.1 | 0.8 |
| 36 | 0.01* | 0.01* | 25 |

A: *Staphylococcus aureus* 209
B: *Escherichia coli* NIHJ
C: *Pseudomonas aeruginosa* 1001
0.01*: no higher than 0.01

The results given above indicate that the compounds of the present invention may be used to treat or prevent diseases caused by a wide range of pathogenic bacteria.

The esters produced as described in Examples 39, 40 and 41 were incubated at 37° C. for 1 hour with horse serum, after which the MIC values were determined. The values were all exactly the same as those of Example 36 and reported above. This means that the esters are easily cleaved by the esterase in the small intestines, after they have been orally administered, and that they are thus absorbed well through the digestive tract, and exhibit in full the activity possessed by the free acid.

The compounds of the invention may be administered either orally or parenterally for the treatment of diseases in humans and other animals caused by pathogenic microorganisms. The compounds may be formulated into any conventional forms for administration. For example, for oral administration, suitable formulations include tablets, granules capsules, powders and syrups, whilst formulations for parenteral administration include injectable solutions for intramuscular or, more preferably intravenous, injection.

The compounds of the invention are preferably administered parenterally, particularly in the form of an intravenous injection.

The dose of the compound of the invention will vary, depending upon the age, body weight and condition of the patient, as well as upon the form and times of administration. However, in general the adult daily dose is expected to be from 100 to 3000 mg of the compound, which may be administered in a single dose or in divided doses.

EXAMPLE 1

(1R, 5S, 6S)-2-[(2S, 4S)-2-Carbamoyl-1,1-dimethylpyrrolidinium-4-ylthio]-6-[(1R)-1-hydroxyethyl]-1-methyl-1-carbapen-2-em-3-carboxylate (1) 5.14 ml of trifluoroacetic acid and 0.13 ml of trifluoromethanesulfonic acid were added dropwise, whilst ice-cooling, to a suspension of 520 mg of (2S, 4S)-2-carbamoyl-4-(4-methoxybenzylthio)-1,1-dimethylpyrrolidinium fluorosulfonate (prepared as described in preparation 1) in 1.45 ml of anisol, and the mixture was stirred at the same temperature for 40 minutes. At the end of this time, the solvent was distilled off, and the residue was washed repeatedly by decantation using diethyl ether and dried under reduced pressure to afford 420 mg of a (2S, 4S)-2-carbamoyl-4-mercapto-1,1-dimethylpyrrolidinium salt as an oil. The anion of this salt was not identified; the same applies hereafter.

(2) 0.20 ml of diisopropylethylamine and 0.24 ml of diphenylphosphoryl chloride were added dropwise, whilst ice-cooling, to a solution of 400 mg of 4-nitrobenzyl (1R, 5R, 6S)-6-[(1R)-1-hydroxyethyl]-1-methyl-2-oxo-1-carbapenam-3-carboxylate in 4 ml of dry acetonitrile, and the mixture was stirred at the same temperature for 1 hour. At the end of this time, 0.46 ml of diisopropylethylamine and a solution of the salt prepared in step (1) above in 3 ml of acetonitrile were added to the reaction mixture, whilst ice-cooling, and the mixture was then stirred for 7 hours and then allowed to stand for 2 days at the same temperature. The solvent was then distilled off under reduced pressure, and the residue was washed repeatedly by decantation using diethyl ether and dried under reduced pressure to afford a crude product. This crude product was then dissolved in a mixture of 30 ml of tetrahydrofuran and 30 ml of a 0.1M phosphate buffer (pH 7.0) and hydrogenated at room temperature for 2.5 hours in the presence of 555 mg of 10% w/w palladium-on-charcoal. At the end of this time, an insoluble material was removed by filtration with the help of a Celite (trade mark) filter aid, and the filtrate was washed with diethyl ether. The aqueous layer was then concentrated by evaporation under reduced pressure. The residue was adsorbed on a column of Diaion (trade mark) HP-20AG (Mitsubishi Chemical Industries, Ltd.) and the fractions eluted with a 5% by volume aqueous acetone solution were concentrated by evaporation under reduced pressure, and the residue was lyophilized to afford a crude product as a yellow powder. This crude product was purified by chromatography using a Lobar column (Merck Co., LiChroprep RP-8, size B). The fractions eluted with 5% and 10% by volume aqueous methanolic solutions were collected and concentrated by evaporation under reduced pressure, and the residue was lyophilized to afford 100 mg of the title compound.

Ultraviolet Absorption Spectrum (H₂O) $\lambda_{max}$ nm: 297.

Nuclear Magnetic Resonance Spectrum (D₂O, 270 MHz) δ ppm: 1.02 (3H, doublet, J=7.33 Hz); 1.10 (3H, doublet, J=6.23 Hz); 2.20-2.31 (1H, multiplet); 2.87-3.22 (2H, multiplet); 3.10 (3H, singlet); 3.14 (3H, singlet); 3.28 (1H, doublet of doublets, J=6.05 & 2.18 Hz); 3.67-3.73 (1H, multiplet); 3.86-4.08 (4H, multiplet); 4.22 (1H, doublet of doublets, J=9.35 & 7.50 Hz).

EXAMPLE 2

(1R, 5S, 6S)-2-[(2S, 4S)-2-Carbamoyl-1-(2-fluoroethyl)-1-methylpyrrolidinium-4-ylthio]-6-[(1R)-1-hydroxyethyl]-1-methyl-1-carbapen-2-em-3-carboxylate (1) 10.0 ml of trifluoroacetic acid and 0.25 ml of trifluoromethanesulfonic acid were added dropwise, whilst ice-cooling, to a suspension of 1.11 g of (2R, 4R)-2-carbamoyl-4-(4-methoxybenzylthio)-1-(2-fluoroethyl)-1-methylpyrrolidinium fluorosulfonate (prepared as described in preparation 2) in 2.83 ml of anisole, and the mixture was then stirred at the same temperature for 1 hour. At the end of this time, the solvent was distilled off, and the residue was repeatedly washed by decantation with diethyl ether and then dried under reduced pressure, to afford 927 mg of a (2S, 4S)-2-carbamoyl-4-mercapto-1-(2-fluoromethyl)-1-methylpyrrolidinium salt.

(2) 0.37 ml of diisopropylethylamine and 0.44 ml of diphenylphosphoryl chloride were added dropwise, whilst ice-cooling, to a solution of 720 mg of 4-nitrobenzyl (1R, 5R, 6S)-6-[(1R)-1-hydroxyethyl]-1-methyl-2-oxo-1-carbapenam-3-carboxylate in 7 ml of dry acetonitrile, and the mixture was stirred at the same temperature for 1 hour. At the end of this time, 0.88 ml of diisopropylethylamine and a solution of the salt prepared as described in step (1) above in 5 ml of acetonitrile were added dropwise to the reaction mixture, whilst ice-cooling, and then the mixture was allowed to stand for 2 days at the same temperature. The solvent was the removed by distillation under reduced pressure, and the residue was washed repeatedly by decantation using diethyl ether and then dried under reduced pressure to afford a crude product. This crude product was dissolved in a mixture of 55 ml of tetrahydrofuran and 55 ml of a 0.1M phosphate buffer (pH 7.0) and then hydrogenated at room temperature for 2 hours in the presence of 1 g of 10% w/w palladium-on-charcoal. At the end of this time, an insoluble material was removed by filtration using a Celite filter aid, and the filtrate was washed with diethyl ether. The aqueous layer was concentrated by evaporation under reduced pressure, and the residue was adsorbed on a column of Diaion HP-20AG (Mitsubishi Chemical Industries, Ltd.). Those fractions eluted with a 5% by volume aqueous acetone solution were concentrated by evaporation under reduced pressure and lyophilized to afford a crude product as a yellow powder. This crude product was purified by chromatography using Lobar column (Merck Co. LiChroprep RP-8, size B). The fractions eluted with a 2% by volume aqueous methanolic solution were collected, concentrated by evaporation under reduced pressure and lyophilized to afford 40 mg of the title compound.

Ultraviolet Absorption Spectrum (H₂O) $\lambda_{max}$ nm: 297.

Nuclear Magnetic Resonance Spectrum (D₂O, 270 MHz) δ ppm: 1.03 (3H, doublet, J=7.33 Hz); 1.10 (3H, doublet, J=6.59 Hz); 2.27-2.35 (1H, multiplet); 2.92-3.12 (2H, multiplet); 3.19 (3H, singlet); 3.29 (1H, doublet of doublets, J=6.05 & 2.75 Hz); 3.67-3.78 (2H, multiplet); 3.91-4.09 (5H, multiplet); 4.37 (1H, doublet of doublets, J=10.81 & 7.50 Hz); 4.69-4.91 (2H, multiplet).

EXAMPLE 3

(1R, 5S, 6S)-2-[(2S, 4S)-1,1-Dimethyl-2-methylcarbamoylpyrrolidinium-4-ylthio]-6-[(1R)-1-hydroxyethyl]-1-methyl-1-carbapen-2-em-3-carboxylate (1) 2.64 ml of trifluoroacetic acid and 0.132 ml of trifluoromethanesulfonic acid were added dropwise, whilst ice-cooling, to a suspension of 280 mg of (2S, 4S)-1,1-dimethyl-2-methylcarbamoyl-4-(4-methoxybenzylthio)pyrrolidinium fluorosulfonate (prepared as described in preparation 3) in 0.744 ml of anisole, and the mixture was stirred at the same temperature for 2 hours. At the end of this time, the solvent was distilled off, and the residue was washed twice by decantation with diethyl ether and then dried by evaporation under reduced pressure, to afford 230 mg of a crude (2S, 4S)-1,1-dimethyl-2-methylcarbamoyl-4-mercaptopyrrolidinium salt as an oil.

(2) 108 μl of diisopropylethylamine and 129 μl of diphenylphosphoryl chloride were added dropwise simultaneously, whilst ice-cooling, to a solution of 225 mg of 4-nitrobenzyl (1R, 5R, 6S)-6-[(1R)-1-hydroxyethyl]-1-methyl-2-oxo-1-carbapenam-3-carboxylate in 3 ml of dry acetonitrile and the mixture was stirred at the same temperature for 1 hour. At the end of this time, 118 μl of diisopropylethylamine and a solution of the salt prepared as described in step (1) above in 2 ml of acetonitrile were added the reaction mixture, whilst ice-cooling. The mixture was then allowed to stand at 0° to 5° C. for 2 hours and for 48 hours in a refrigerator. At the end of this time, the solvent was distilled off, and the residue was washed repeatedly by decantation with diethyl ether and dried under reduced pressure to afford a crude product. This crude product was dissolved in a mixture of 20 ml of tetrahydrofuran and 20 ml of a 0.1M phosphate buffer (pH 7.0) and hydrogenated at room temperature for 2.5 hours in the presence of 254 mg of 10% w/w palladium-on-charcoal. At the end of this time, an insoluble material was removed by filtration using a Celite filter aid, and the filtrate was washed using diethyl ether. The aqueous layer was concentrated by evaporation under reduced pressure. The resulting residue was adsorbed on a column of Diaion HP-20AG (Mitsubishi Chemical Industries, Ltd.) and the fractions eluted with a 5% by volume aqueous acetone solution were concentrated by evaporation under reduced pressure. The resulting residue was then lyophilized to afford a crude product as a powder. This crude product was purified by chromatography using a Lobar column (Merck Co. LiChroprep RP-8, size B). The fractions eluted with 10% and 15% by volume aqueous methanolic solutions were collected and concentrated by evaporation under reduced pressure. The resulting residue was lyophilized to afford 9.0 mg of the title compound.

Ultraviolet Absorption Spectrum (H₂O) $\lambda_{max}$ nm: 297.5.

Nuclear Magnetic Resonance Spectrum (D₂O, 270 MHz) δ ppm: 1.02 (3H, doublet, J=7.33 Hz); 1.10 (3H, doublet, J=6.59 Hz); 2.19–2.31 (1H, multiplet); 2.63 (3H, singlet); 2.82–3.23 (2H, multiplet); 3.05 (3H, singlet); 3.12 (3H, singlet); 3.29 (1H, doublet of doublets, J=6.22 & 2.93 Hz); 3.70 (1H, doublet of doublets, J=12.46 & 5.13 Hz); 3.83–4.20 (5H, multiplet).

EXAMPLE 4

(1R, 5S, 6S)-2-[(2S, 4S)-1,1-Dimethyl-2-(N,N-dimethylcarbamoyl)pyrrolidinium-4-ylthio]-6-[(1R)-1-hydroxyethyl]-1-methyl-1-carbapen-2-em-3-carboxylate (1) 3.3 ml of trifluoroacetic acid and 0.12ml of trifluoromethanesulfonic acid were added dropwise, whilst ice-cooling, to a suspension of 350 mg of (2S, 4S)-1,1-dimethyl-2-(N,N-dimethylcarbamoyl)-4-(4-methoxybenzylthio)pyrrolidinium fluorosulfonate (prepared as described in preparation 4) in 0.66 ml of anisole, and the mixture was stirred at room temperature for 2 hours. At the end of this time, the solvent was removed by distillation under reduced pressure, and the residue was washed twice by decantation with hexane and diethyl ether, in that order, and dried under reduced pressure to afford 316 mg of a crude (2S, 4S)-1,1-dimethyl-2-(N,N-dimethylcarbamoyl)-4-mercaptopyrrolidinium salt as an oil. This was used in the following reaction without further purification.

(2) 164 μl of diisopropylethylamine and 196 μl of diphenylphosphoryl chloride were added simultaneously, whilst ice-cooling, to a solution of 326 mg of 4-nitrobenzyl (1R, 5R, 6S)-6-[(1R)-1-hydroxyethyl]-1-methyl-2-oxo-1-carbapenam-3-carboxylate in 4 ml of dry acetonitrile, and the mixture was stirred at the same temperature for 1 hour. At the end of this time, 248 μl of diisopropylethylamine and a solution of the salt prepared as described in step (1) above in 3 ml of acetonitrile were added to the reaction mixture, whilst ice-cooling. The mixture was then allowed to stand at 0° to 5° C. for 1 hour and then in a refrigerator for a further 2 days. At the end of this time, the reaction mixture was treated in a similar manner to that described in Example 1-(2). The resulting crude product was then dissolved in a mixture of 20 ml of tetrahydrofuran and 20 ml of a 0.1M phosphate buffer (pH 7.0) and hydrogenated at room temperature for 2.5 hours in the presence of 400 mg of 10% w/w palladium-on-charcoal. Reduction and purification were then carried out in a similar manner to that described in Example 1-(2), to afford 101 mg of the title compound.

Ultraviolet Absorption Spectrum (H₂O) λ$_{max}$ nm: 298.

Nuclear Magnetic Resonance Spectrum (D₂O, 270 MHz) δppm: 1.03 (3H, doublet, J=7.33 Hz); 1.11 (3H, doublet, J=6.22 Hz); 2.19 (1H, quintet, J=7.20 Hz); 2.83 (3H, singlet); 2.90–3.18 (2H, multiplet); 3.01 (3H, singlet); 3.10 (3H, singlet); 3.12 (3H, singlet); 3.29 (1H, doublet of doublets, J=6.23 & 2.56 Hz); 3.74–3.91 (2H, multiplet); 3.96–4.11 (3H, multiplet); 4.76 (1H, triplet, J=7.70 Hz).

EXAMPLE 5

(1R, 5S, 6S)-2-[(3S)-1,1-Dimethylpyrrolidinium-3-ylthio]-6-[(1R)-1-hydroxyethyl]-1-methyl-1-carbapen-2-em-3-carboxylate (1) 4.97 ml of trifluoroacetic acid and 0.249 ml of trifluoromethanesulfonic acid were added dropwise, whilst ice-cooling, to a suspension of 453 mg of (3S)-1,1-dimethyl-3-(4-methoxybenzylthio)pyrrolidinium fluorosulfonate (prepared as described in preparation 5) in 1.40 ml of anisole, and the mixture was stirred at the same temperature for 2 hours. At the end of this time, the solvent was distilled off, and the residue was washed twice by decantation with diethyl ether and dried under reduced pressure to afford 250 mg of a crude (3S)-1,1-dimethyl-3-mercaptopyrrolidinium salt as an oil.

(2) 126 μl of diisopropylethylamine and 150 μl of diphenylphosphoryl chloride were added simultaneously, whilst ice-cooling, to a solution of 250 mg of 4-nitrobenzyl (1R, 5R, 6S)-6-[(1R)-1-hydroxyethyl]-1-methyl-2-oxo-1-carbapenam-3-carboxylate in 2 ml of dry acetonitrile, and the mixture was stirred at the same temperature for 1 hour. At the end of this time, 145 μl of diisopropylethylamine and a solution of the salt prepared as described in step (1) above in 4 ml of acetonitrile were added the reaction mixture, whilst ice-cooling. The reaction mixture was then allowed to stand at 0° to 5° C. for 2 hours and for 2 days in a refrigerator. At the end of this time, the solvent was removed by distillation under reduced pressure, and the residue was mixed with diethyl ether and then decanted. The resulting crude product was dissolved in a mixture of 20 ml of tetrahydrofuran and 20 ml of a 0.1M phosphate buffer (pH 7.0) and hydrogenated at room temperature for 2.5 hours in the presence of 300 mg of 10% w/w palladium-on-charcoal. At the end of this time, an insoluble material was removed by filtration using a Celite filter aid, and the filtrate was washed using diethyl ether. The aqueous layer was concentrated by evaporation under reduced pressure. The residue was adsorbed on a column of Diaion HP-20AG (Mitsubishi Chemical Industries, Ltd.) and the fractions eluted with a 5% by volume aqueous acetone solution were concentrated by evaporation under reduced pressure and lyophilized to afford a crude product as a powder. This crude product was purified by chromatography using a Lobar column (Merck Co. LiChroprep RP-8, size B). The fractions eluted with 10% and 15% by volume aqueous methanolic solutions were collected, concentrated by evaporation under reduced pressure and lyophilized to afford 90 mg of the title compound.

Ultraviolet Absorption Spectrum (H₂O) λ$_{max}$ nm: 297.3

Nuclear Magnetic Resonance Spectrum (D₂O, 270 MHz) δ ppm: 1.02 (3H, doublet, J=7.33 Hz); 1.09 (3H, doublet, J=6.59 Hz); 1.96–2.14 (1H, multiplet); 2.52–2.70 (1H, multiplet); 3.00 (3H, singlet); 3.09 (3H, singlet); 3.04–3.18 (1H, multiplet); 3.28 (1H, doublet of doublets, J=6.05 & 2.75 Hz), 3.38–3.67 (3H, multiplet); 3.80 (1H, doublet of doublets, J=12.46 & 7.70 Hz), 3.91–4.11 (3H, multiplet).

EXAMPLE 6

(5R, 6S)-2-[(3S)-1,1-Dimethylpyrrolidinium-3-ylthio]-6-[(1R)-1-hydroxyethyl]-1-carbapen-2-em-3-carboxylate 183 μl of diisopropylethylamine and 218 μl of diphenylphosphoryl chloride were simultaneously added, whilst ice-cooling, to a solution of 348 mg of 4-nitrobenzyl (5R, 6S)-6-[(1R)-1-hydroxyethyl]-2oxo-1-carbapenam-3-carboxylate dissolved in 4 ml of dry acetonitrile, and the mixture was stirred at the same temperature for 1 hour. At the end of this time a solution of 338 mg of the crude (3S)-1,1-dimethyl-3-mercaptopyrrolidinium salt prepared as described in Example 5-(1) in 4 ml of dry acetonitrile and 201 μl of diisopropylamine were added to the mixture, whilst ice-cooling. The mixture was then allowed to stand at the same temperature for 1 hour and then for two days in a refrigerator. At the end of this time, the reaction mixture was washed by decantation with diethyl ether. The resulting product was dissolved in a mixture of 30 ml of tetrahydrofuran and 30 ml of a 0.1M phosphate buffer (pH 7.0) and hydrogenated at room temperature for 2.5 hours in the presence of 400 mg of 10% w/w palladium-on-charcoal. At the end of this time, an insoluble material was removed by filtration and the filtrate was washed with diethyl ether. The aqueous layer was concentrated by evaporation under reduced pressure and then subjected to column chromatography through Diaion HP-20AG (Mitsubishi Chemicals Industries Inc.). The title compound was prepared as a crude product from the fractions eluted with water. The crude compound was then further purified by chromatography through a Lobar column (Merck, LiChroprep RP-8, size B) and the fractions eluted with 5% by volume aqueous methanol were collected, concentrated by evaporation under reduced pressure and lyophilized to afford 60 mg of the title compound.

Ultraviolet Absorption Spectrum (H2O) $\lambda_{max}$ nm: 298.

Nuclear magnetic resonance spectrum (270 MHz, D$_2$O) δ ppm: 1.09 (3H, doublet, J=6.23 Hz); 2.01–2.18 (1H, multiplet); 2.53–2.72 (1H, multiplet); 2.89–3.04 (2H, multiplet); 3.01 (3H, singlet); 3.09 (3H, singlet); 3.23 (1H, doublet of doublets, J=6.05 & 2.75 Hz); 3.36–3.67 (3H, multiplet); 3.85 (1H, doublet of doublets, J=12.64 & 8.24 Hz); 3.93–4.09 (3H, multiplet).

EXAMPLE 7

(1R, 5S, 6S)-2-[1,1-Dimethylpiperidinium-4-ylthio]-6-[(1R)-1-hydroxyethyl]-1-methyl-1-carbapen-2-em-3-carboxylate 7-(1) 31.6 ml of trifluoroacetic acid and 1.6 ml of trifluoromethanesulfonic acid were added, whilst ice-cooling, to a suspension of 3.0 g of 1,1-dimethyl-4-(4-methoxybenzylthio)piperidinium fluorosulfonate (prepared as described in preparation 6) in 8.9 ml of anisole. The mixture was then stirred for 3 hours, after which it was freed from the solvent by distillation under reduced pressure. The residue was repeatedly washed by decantation with diethyl ether and dried under reduced pressure to afford 2.4 g of a crude 1,1-dimethyl-4-mercaptopiperidinium salt as an oil.

7-(2) 126 μl of diisopropylethylamine and 150 μl of diphenylsulfonyl chloride were added simultaneously, whilst ice-cooling, to a solution of 250 mg of 4-nitrobenzyl (1R, 5R, 6S)-6-[(1R)-1-hydroxyethyl]-1-methyl-2-oxo-1-carbapenam-3-carboxylate dissolved in 2 ml of dry acetonitrile, and the mixture was stirred at the same temperature for 1 hour. At the end of his time, 288 μl of diisopropylethylamine and a solution of 245 μl of the salt prepared as described in step (1) in 4 ml of dry acetonitrile were added to the mixture, which was then allowed to stand for 2 days in a refrigerator. The reaction mixture was then poured into diethyl ether and the resulting precipitate was washed by decantation. The resulting crude product was then dissolved in 20 ml of a 0.1M phosphate buffer (pH 7.0) and hydrogenated at room temperature for 2 hours in the presence of 331 mg of 10% w/w palladium-on-charcoal. At the end of this time, the reaction mixture was worked up in a similar manner to that described in Example 5 -(2) to afford 11.3 mg of the title compound.

Ultraviolet Absorption Spectrum (H2O) $\lambda_{max}$ nm: 278.

Nuclear Magnetic Resonance Spectrum (D$_2$O, 270 MHz) δ ppm: 1.02 (3H, doublet, J=6.96 Hz); 1.10 (3H, doublet, J=6.23 Hz); 1.70–1.93 (2H, multiplet); 2.03–2.20 (2H, multiplet); 2.97 (6H, singlet); 3.11–3.48 (7H, multiplet); 4.01–4.12 (2H, multiplet).

EXAMPLE 8

(5R, 6S)-2-[1,1-Dimethylpiperidinium-4-ylthio]-6-[(1R)-1-hydroxyethyl]-1-carbapen-2-em-3-carboxylate Following a procedure similar to that described in Example 6, but using 368 mg of the crude 1,1-dimethyl-4-mercaptopiperidinium salt prepared as described in Example 7-(1) and, 363 mg of 4-nitrobenzyl (5R, 6S)-6-[(1R)-1-hydroxyethyl]-2-oxo-1-carbapenam-3-carboxylate, 24 mg of the title compound were obtained.

Ultraviolet Absorption Spectrum (H2O) $\lambda_{max}$ nm: 299.

Nuclear Magnetic Resonance Spectrum (D$_2$O, 270 MHz) δ ppm: 1.09 (3H, doublet, J=6.23 Hz); 1.74–1.93 (2H, multiplet); 2.02–2.16 (2H, multiplet); 2.86–3.43 (8H, multiplet); 2.96 (6H, singlet); 3.97–4.08 (2H, multiplet).

EXAMPLE 9

(1R, 5S, 6S)-2-[(2S, 4S)-2-(N,N-dimethylcarbamoyl)-1-ethyl-1-methylpyrrolidinium-4-ylthio-6-[(1R)-1-hydroxyethyl]-1-methyl-1-carbapen-2-em-3-carboxylate 9-(1) 4.94 ml of trifluoroacetic acid and 248 μl of trifluoromethanesulfonic acid were added, whilst ice-cooling, to a suspension of 560 mg of (2S, 4S)-2-(N,N-dimethylcarbamoyl)-1-ethyl-1-methyl-4-(4-methoxybenzylthio)pyrrolidinium fluorosulfonate (prepared as described in preparation 7) in 1.39 ml of anisole, and the mixture was stirred at the same temperature for 2 hours. At the end of this time, the solvent was removed by distillation under reduced pressure, and the residue was washed twice by decantation with diethyl ether and then dried under reduced pressure, to afford 460 mg of a crude (2S, 4S)-2-(N,N-dimethylcarbamoyl)-1-ethyl-1-methyl-4-mercaptopyrrolidinium salt as an oil.

Nuclear Magnetic Resonance Spectrum (D$_2$O, 270 MHz) δ ppm: 1.21 (3H. triplet, J=7.33 Hz); 2.14 (1H, doublet of triplets, J=14.29 & 7.15 Hz); 2.82 (3H, singlet); 2.98 (3H, singlet); 3.00 (3H, singlet); 2.86–3.94 (6H, multiplet); 4.69 (1H, triplet, J=7.15 Hz).

9-(2) 152 μl of diisopropylethylamine and 181 μl of diphenylphosphoryl chloride were added simultaneously, whilst ice-cooling, to a solution of 310 mg of 4-nitrobenzyl (1R, 5R, 6S)-6-[(1R)-1-hydroxyethyl]-1-methyl-2-oxo-1-carbapenam-3-carboxylate dissolved in 4 ml of dry acetonitrile, and the mixture was stirred for 1 hour, whilst ice-cooling. At the end of this time, 174 μl of diisopropylethylamine and a solution of 366 mg of the salt prepared as described in step (1) in 4 ml of dry acetonitrile were added to the mixture, which was then allowed to stand for 1 hour at 0° to 5° C. and then for 2 days in a refrigerator. At the end of this time, the reaction mixture was poured into diethyl ether and washed by decantation. The crude products thus obtained were dissolved in a mixture of 25 ml of tetrahydrofuran and 25 ml of a 0.1M phosphate buffer (pH 7.0) and hydrogenated at room temperature for 2.5 hours in the presence of 340 mg of 10% w/w palladium-on-charcoal. At the end of this time, the reaction mixture was worked up and purified in a similar manner to that described in Example 1-(2), to afford 127 mg of the title compound.

Ultraviolet Absorption Spectrum (H$_2$O) $\lambda_{max}$ nm: 297.0.

Nuclear Magnetic Resonance Spectrum (D$_2$O, 270 MHz) δ ppm: 1.02 (3H, doublet, J=6.96 Hz); 1.10 (3H, doublet, J=6.22 Hz); 1.22 (3H, triplet, J=7.32 Hz); 2.12–2.25 (1H, multiplet); 2.82 (3H, singlet); 2.83–3.50, (5H, multiplet); 3.00 (3H, singlet); 3.05 (3H, singlet); 3.65 (1H, doublet of doublets, J=12.45 & 5.3 Hz); 3.85 (1H, doublet of doublets, J=12.45 & 8.42 Hz); 3.91–4.12 (3H, multiplet); 4.68–4.75 (1H, multiplet).

EXAMPLE 10

(5R, 6S)-2-(2S, 4S)-1-Ethyl-1-methyl-2-(N,N-dimethylcarbamoyl)pyrrolidinium-4-ylthio]-6-[(1R)-1-hydroxyethyl]-1-carbapen-2-em-3-carboxylate Following a procedure similar to that described in Example 6, but using 459 mg of 4-nitrobenzyl (5R, 6S)-6-[(1R)-1-hydroxyethyl]-2-oxo-1-carbapenam-3-carboxylate and 580 mg of the crude (2S, 4S)-2-(N,N-dimethylcarbamoyl)-1-ethyl-1-methyl-4-mercaptopyrrolidinium salt [prepared as described in Example 9-(2)], 55 mg of the title compound were obtained.

Ultraviolet Absorption Spectrum (H$_2$O) $\lambda_{max}$ nm: 298.

Nuclear Magnetic Resonance Spectrum (D$_2$O, 270 MHz) δ ppm: 1.10 (3H, doublet, J=6.59 Hz); 1.23 (3H, triplet, J=7.15 Hz); 2.17–2.30 (1H, multiplet); 2.83 (3H, singlet); 2.83–3.07 (2H, multiplet); 3.00 (3H, singlet); 3.01 (3H, singlet); 3.05 (3H, singlet); 3.24 (1H, doublet of doublets, J=6.04 & 2.75 Hz); 3.27–4.18 (7H, multiplet); 4.72 (1H, triplet, J=8.06 Hz).

EXAMPLE 11

(5R, 6S)-2-[(2S, 4S)-1,1,-Dimethyl-2-(N,N-dimethylcarbamoyl)pyrrolidinium-4-ylthio]-6-[(1R)-1-hydroxyethyl]-1-carbapen-2-em-3-carboxylate 126 μl of diisopropylethylamine and 132 μl of diphenylphophoryl chloride were simultaneously added, whilst ice-cooling, to a solution of 218 mg of 4-nitrobenzyl (5R, 6S)-6-[(1R)-1-hydroxyethyl]-2-oxo-1-carbapenam-3-carboxylate dissolved in 3 ml of dry acetonitrile, and the mixture was stirred at the same temperature for 1 hour. At the end of this time a solution of 243 mg of the crude (2S, 4S)-2-(N,N-dimethylcarbamoyl)-1,1-dimethyl-4-mercaptopyrrolidinium salt [prepared as described in Example 4-(1)] in 2 ml of dry acetonitrile and 144 μl of diisopropylethylamine were added to the mixture, whilst ice-cooling. The mixture was then allowed to stand at the same temperature for 5 hours and then for 2 days in a refrigerator. At the end of this time, the reaction mixture was worked up in a similar manner to that described in Example 6. The crude product was dissolved in a mixture of 15 ml of tetrahydrofuran and 15 ml of a 0.1M phosphate buffer (pH 7.0) and hydrogenated at room temperature for 2 hours in the presence of 200 mg of 10% w/w palladium-on-charcoal. At the end of this time, the reaction mixture was worked up and purified in a similar manner to that described in Example 6, to afford 56 mg of the title compound.

Ultraviolet Absorption Spectrum (H$_2$O) $\lambda_{max}$ nm: 299.

Nuclear Magnetic Resonance Spectrum (D$_2$O, 270 MHz) δ ppm: 1.10 (3H, doublet, J=6.23 Hz); 2.17–2.28 (1H, multiplet); 2.79–3.04 (3H, multiplet); 2.83 (3H, singlet); 3.00 (3H, singlet); 3.11 (3H, singlet); 3.12 (3H, singlet); 3.24 (1H, doublet of doublets, J=6.05 & 2.75 Hz); 3.76–3.96 (2H, multiplet); 3.97–4.12 (3H, multiplet); 4.76 (1H, triplet, J=7.33 Hz).

EXAMPLE 12

(1R, 5S, 6S)-2-[(2S, 4S)-1,1-Dimethyl-2-(4-morpholinocarbonyl)pyrrolidinium-4-ylthio]-6-[(1R)-1-hydroxyethyl]-1-methyl-1-carbapen-2-em-3-carboxylate Following a procedure similar to that described in Example 4, but using 446 mg of (2S, 4S)-1,1-dimethyl-4-(4-methoxybenzylthio)-2-(4-morpholinocarbonyl)pyrrolidinium fluorosulfonate (prepared as described in Preparation 8) [in step (1)] and 192 mg of 4-nitrobenzyl (1R, 5R, 6S)-6-[(1R)-1-hydroxyethyl]-1-methyl-2-oxo-1-carbapenam-3-carboxylate [in step (2)], 16 mg of the title compound were obtained.

Ultraviolet Absorption Spectrum (H$_2$O) $\lambda_{max}$ nm: 297.

Nuclear Magnetic Resonance Spectrum (D$_2$O, 270 MHz) δ ppm: 1.02 (3H, doublet, J=7.32 Hz); 1.10 (3H, doublet, J=6.59 Hz); 2.16–2.28 (1H, multiplet); 2.90–3.18 (2H, multiplet); 3.10 (3H, singlet); 3.15 (3H, singlet); 3.29 (1H, doublet of doublets, J=6.23 & 2.93 Hz); 3.43–3.65 (8H, multiplet); 3.76–3.93 (2H, multiplet); 3.96–4.12 (3H, multiplet); 4.76 (1H, triplet, J=7.69 Hz).

EXAMPLE 13

(1R, 5S, 6S)-2-[(2S, 4S)-1,1-Dimethyl-2-(1-pyrrolidinocarbonyl)pyrrolidinium-4-ylthio]-6-[(1R)-1-hydroxyethyl]-1-methyl-1-carbapen-2-em-3-carboxylate Following a procedure similar to that described in Example 4, but using 472 mg of (2S, 4S)-1,1-dimethyl-4-(4-methoxybenzylthio)-2-(1-pyrrolidinocarbonyl)pyrrolidinium fluorosulfonate (prepared as described in preparation 9) [in step (1)] and 220 mg of 4-nitrobenzyl (1R, 5R, 6S)-6-[(1R)-1-hydroxyethyl]-1-methyl-2-oxo-1-carbapenam-3-carboxylate [in step (2)], 24 mg of the title compound were obtained.

Ultraviolet Absorption Spectrum (H$_2$O) $\lambda_{max}$ nm: 298.

Nuclear Magnetic Resonance Spectrum (D$_2$O, 270 MHz) δ ppm: 1.02 (3H, doublet, J=6.96 Hz); 1.10 (3H, doublet, J=6.23 Hz); 1.65–1.84 (4H, multiplet); 2.14–2.24 (1H, multiplet); 2.92–3.04 (1H, multiplet); 3.10 (3H, singlet); 3.12 (3H, singlet); 3.20–3.57 (5H, multiplet); 3.74–4.11 (6H, multiplet); 4.47–4.63 (1H, multiplet).

EXAMPLE 14

(1R, 5S, 6S)-2-[(2S, 4S)-2-Carbamoyl-1-ethyl-1-methylpyrrolidinium-4-ylthio]-6-[(1R)-1-hydroxyethyl]-1-methyl-1-carbapen-2-em-3-carboxylate 14-(1) 4.2 ml of trifluoroacetic acid and 0.11 ml of trifluoromethanesulfonic acid were added dropwise, whilst ice-cooling, to a suspension of 450 mg of (2S, 4S)-2-carbamoyl-4-(4-methoxybenzylthio)-1-ethyl-1-methylpyrrolidinium fluorosulfonate (prepared as described in preparation 10) in 1.2 ml of anisole. The mixture was then stirred at the same temperature for 90 minutes, after which it was freed from the solvent by distillation under reduced pressure. The residue was washed by decantation with diethyl ether and dried under reduced pressure, to afford 370 mg of a (2S, 4S)-2-carbamoyl-4-mercapto-1-ethyl-1-methylpyrrolidinium salt as an oil.

Infrared Absorption Spectrum (liquid film) $\nu_{max}$ cm$^{-1}$; 1699, 1247, 1169.

Nuclear Magnetic Resonance Spectrum (D$_2$O, 270 MHz) δ ppm: 1.20 (3H, triplet, J=7.32 Hz); 2.13–2.25 (1H, multiplet); 2.80–3.92 (6H, multiplet); 2.98 (3H, singlet); 4.11–4.17 (1H, multiplet).

14-(2) Following a procedure similar to that described in Example 9, but using 300 mg of 4-nitrobenzyl (1R, 5R, 6S)-6-[(1R)-1-hydroxyethyl]-1-methyl-2-oxo-1-carbapenam-3-carboxylate and 340 mg of the salt prepared as described in step (1). 120 mg of the title compound were obtained.

Ultraviolet Absorption Spectrum (H$_2$O) $\lambda_{max}$ nm: 297.

Nuclear Magnetic Resonance Spectrum (D$_2$O, 270 MHz) δ ppm; 1.02 (3H, doublet, J=6.96 Hz); 1.10 (3H, doublet, J=6.23 Hz); 1.23 (3H, triplet, J=7.33 Hz); 2.21–2.35 (1H, multiplet); 2.88–3.25 (2H, multiplet); 3.04 (3H, singlet); 3.26–4.08 (8H, multiplet); 4.22 (1H, doublet of doublets, J=10.26 & 7.32 Hz).

EXAMPLE 15

(5R, 6S)-2-[(2S, 4S)-2-Carbamoyl-1-ethyl-1-methylpyrrolidinium-4-ylthio]-6-[(1R)-1-hydroxyethyl]-+-carbapen-2-em-3-carboxylate Following a procedure similar to that described in Example 11, but using 450 mg of 4-nitrobenzyl (5R, 6S)-6-[(1R)-1-hydroxyethyl]-2-oxo-1-carbapenam-3-carboxylate and 530 mg of the salt prepared as described in Example 14-(1), 205 mg of the title compound were obtained.

Ultraviolet Absorption Spectrum (H$_2$O) $\lambda_{max}$ nm: 298.

Nuclear Magnetic Resonance Spectrum (D$_2$O, 270 MHz) δ ppm: 1.09 (3H, doublet, J=6.60 Hz); 1.24 (3H, triplet, J=7.33 Hz); 2.26–2.38 (1H, multiplet); 2.84–3.07 (2H, multiplet); 3.03 (3H, singlet); 3.24 (1H, doublet of doublets, J=6.05 & 2.93 Hz); 3.27–4.06 (8H, multiplet); 4.22 (1H, doublet of doublets, J=10.26 & 7.33 Hz).

EXAMPLE 16

(5R, 6S)-2-[(2S, 4S)-2-Carbamoyl-1,1-dimethylpyrrolidinium-4-ylthio]-6-[(1R)-1-hydroxyethyl]-1-carbapen-2-em-3-carboxylate 210 μl of diisopropylethylamine and 250 μl of diphenylphosphoryl chloride were simultaneously added, whilst ice-cooling, to a solution of 400 mg of 4-nitrobenzyl (5R, 6S)-6-[(1R)-1-hydroxyethyl]-2oxo-1-carbapenam-3-carboxylate dissolved in 5 ml of dry acetonitrile, and the mixture was stirred for 1 hour, whilst ice-cooling. At the end of this time, a solution of 447 mg of the crude (2S, 4S)-2-carbamoyl-1,1-dimethyl-4-mercaptopyrrolidinium salt prepared as described in Example 1-(1) in 5 ml of dry acetonitrile was added to the mixture, whilst ice-cooling, and then the mixture was allowed to stand for 4 hours at the same temperature and then for 2 days in a refrigerator. The reaction mixture was then poured into diethyl ether and the resulting deposit was washed repeatedly by decantation. The crude product was dissolved in a mixture of 30 ml of tetrahydrofuran and 30 ml of a 0.1M phosphate buffer (pH 7.0) and hydrogenated at room temperature for 2.5 hours in the presence of 450 mg of 10% w/w palladium-on-charcoal. At the end of this time, insoluble materials were removed by filtration using a Celite filter aid. The aqueous layer was concentrated by evaporation under reduced pressure, and the residue was transferred to a column packed with Diaion HP-20AG (Mitsubishi Chemicals Industries, Ltd.). Fractions eluted with water were collected and lyophilized to afford the title compound as a powder. This was further purified using a Lobar column (Merck, LiChroprep RP-8 size B) and fractions eluted with a 5% by volume aqueous methanolic solution were collected and concentrated by evaporation under reduced pressure followed by lyophilization, to afford 208 mg of the title compound.

Ultraviolet Absorption Spectrum (H$_2$O) $\lambda_{max}$ nm: 297.7.

Nuclear Magnetic Resonance Spectrum (D$_2$O, 270 MHz) δ ppm: 1.09 (3H, doublet, J=6.59 Hz); 2.23–2.36 (1H, multiplet); 2.86–3.04 (3H, multiplet); 3.10 (3H, singlet); 3.15 (3H, singlet); 3.23 (1H, doublet of doublets, J=5.86 & 2.57 Hz); 3.73 (1H, doublet of doublets, J=12.09 & 5.50 Hz); 3.90–4.08 (4H, multiplet); 4.22 (1H, doublet of doublets, J=9.16 & 7.69 Hz).

EXAMPLE 17

(1R, 5S, 6S)-2-(2S, 4S)-2-Ethylcarbamoyl-1-ethyl-1-methylpyrrolidinium-4-ylthio]-6-(1R)-1-hydroxyethyl)-1-methyl-1-carbapen-2-em-3-carboxylate 17-(1) 10.86 ml of trifluoroacetic acid and 544 μl of trifluoromethanesulfonic acid were added, whilst ice-cooling, to a suspension of 1.23 g of (2S, 4S)-2-ethylcarbamoyl-1-ethyl-1-methyl-4-(4-methoxybenzylthio)pyrrolidinium fluorosulfonate (prepared as described in preparation 11) in 3.06 ml of anisole, and the mixture was stirred for 2 hours under the same conditions. The solvent was then removed by distillation under reduced pressure, and the residue was washed thrice by decantation with diethyl ether and dried under reduced pressure, to afford 0.96 g of a crude (2S, 4S)-2-ethylcarbamoyl-1-ethyl-1-methyl-4-mercaptopyrrolidinium salt.

Nuclear Magnetic Resonance Spectrum (D$_2$O, 270 MHz) δ ppm: 0.96 (3H, triplet, J=7.33 Hz); 1.21 (3H, triplet, J=7.33 Hz); 2.13–2.26 (1H, multiplet); 2.95 (3H, singlet); 2.73–4.16 (9H, multiplet).

17-(2) Following a procedure similar to that described in Example 1, but using 250 mg of 4-nitrobenzyl (1R, 5S, 6S)-6-[(1R)-1-hydroxyethyl]-1-methyl-2-oxo-1-carbapenam-3-carboxylate and 304 mg of the salt prepared as described in step (1), 69 mg of the title oompound were obtained.

Ultraviolet Absorption Spectrum (H$_2$O) $\lambda_{max}$ nm: 296.6.

Nuclear Magnetic Resonance Spectrum (D$_2$O, 270 MHz) δ ppm: 0.95 (3H, triplet, J=7.32 Hz); 1.02 (3H, doublet, J=7.33 Hz); 1.10 (3H, doublet, J=6.59 Hz); 1.22 (3H, triplet, J=7.33 Hz); 2.12–2.34 (1H, multiplet); 2.99 (3H, singlet); 3.03–4.18 (12 H, multiplet).

EXAMPLE 18

(5R, 6S)-2-[(2S, 4S)-2-Ethylcarbamoyl-1-ethyl-1-methylpyrrolidinium-4-ylthio]-6-[(1R)-1-hydroxyethyl]-1-carbapen-2-em-3-carboxylate Following a procedure similar to that described in Example 16, but using 348 mg of 4-nitrobenzyl (5R, 6S)-6-[(1R)-1-hydroxyethyl]-2-oxo-1-carbapenam-3-carboxylate and 440 mg of the crude (2S, 4S)-2-ethylcarbamoyl-1-ethyl-1-methyl-4-mercaptopyrrolidinium salt prepared as described in Example 17-(1), 80 mg of the title compound were obtained.

Ultraviolet Absorption Spectrum (H$_2$O) λ$_{max}$ nm: 298.2.

Nuclear Magnetic Resonance Spectrum (D$_2$O, 270 MHz) δ ppm: 0.95 (3H, triplet, J=7.32 Hz); 1.09 (3H, doublet, J=6.59 Hz); 1.23 (3H, triplet, J=7.33 Hz); 2.13–2.37 (1H, multiplet); 2.76–3.05 (3H, multiplet); 2.98 (3H, singlet); 3.09 (2H, quartet, J=7.33 Hz); 3.23 (1H, doublet of doublets, J=6.05 & 2.75 Hz); 3.22–4.18 (8H, multiplet).

EXAMPLE 19

(1R, 5S, 6S)-2-[(2S, 4S)-1-Ethyl-1-methyl-2-methylcarbamoylpyrrolidinium-4-ylthio-6-[(1R)-1-hydroxyethyl]-1-methyl-1-carbapen-2-em-3-carboxylate Following a procedure similar to that described in Example 1, but using 986 mg of (2S, 4S)-1-ethyl-1-methyl-2-methylcarbamoyl-4-(4-methoxybenzylthio)pyrrolidinium fluorosulfonate (prepared as described in preparation 12) [in step (1)] and 362 mg of methyl-2-oxo-1-carbapenam-3-carboxylate [in step (2)], 74 mg of the title compound were obtained.

Ultraviolet Absorption Spectrum (H$_2$O) λ$_{max}$ nm: 296.6.

Nuclear Magnetic Resonance Spectrum (D$_2$O, 270 MHz) δ ppm: 1.02 (3H, doublet, J=7.33 Hz); 1.10 (3H, doublet, J=6.59 Hz); 1.21 (3H, triplet, J=7.33 Hz); 2.11–2.33 (1H, multiplet); 2.62 (3H, singlet); 2.77–2.90, (1H, multiplet); 2.98 (3H, singlet); 3.00–4.23 (10H, multiplet).

EXAMPLE 20

(1R, 5S, 6S)-2-[(2S, 4S)-1,1-Dimethyl-2-ethylcarbamoylpyrrolidinium-4-ylthio]-6-[(1R)-1-hydroxyethyl]-1-methyl-1-carbapen-2-em-3-carboxylate 20-(1) 11.56 ml of trifluoroacetic acid and 580 μl of trifluoromethanesulfonic acid were added, whilst ice-cooling, to a suspension of 1.27 g of (2S, 4S)-1,1-dimethyl-2-ethylcarbamoyl-4-(4-methoxybenzylthio)pyrrolidinium fluorosulfonate (prepared as described in preparation 13) in 3.26 ml of anisole, and the mixture was stirred for 2 hours under the same conditions. At the end of this time, the solvent was removed by distillation under reduced pressure, and the residue was washed thrice by decantation with diethyl ether and then dried under reduced pressure, to afford 802 mg of a crude (2S, 4S)-1,1-dimethyl-2-ethylcarbamoyl-4-mercaptopyrrolidinium salt as an oil.

Nuclear Magnetic Resonance Spectrum (D$_2$O, 270 MHz) δ ppm: 0.96 (3H, triplet, J=7.33 Hz); 2.18 (1H, doublet of triplets, J=14.66, 7.33 Hz); 2.79–2.98 (1H, multiplet); 3.03 (3H, singlet); 3.06 (3H, singlet); 3.10 (2H, quartet, J=7.33 Hz); 3.46–3.92 (3H, multiplet); 4.06 (1H, triplet, J=7.33Hz).

20-(2) 340 mg of diisopropylethylamine and 405 μl of diphenylphosphoryl chloride were added simultaneously, whilst ice-cooling, to a solution of 674 mg of 4-nitrobenzyl (1R, 5R, 6S)-6-[(1R)-1-hydroxyethyl]-1-methyl-2-oxo-1-carbapenam-3-carboxylate dissolved in 10 ml of dry acetonitrile, and the mixture was stirred at the same temperature for 1 hour. At the end of this time, a solution of 390 μl of diisopropylethylamine and 790 mg of the salt prepared as described in step (1) in 8 ml of dry acetonitrile were added to the reaction mixture, which was then allowed to stand at 0° to 5° C. for 2 hours and then for 2 days in a refrigerator. At the end of this time, the reaction mixture was poured into diethyl ether and washed by decantation. The resulting crude product was dissolved in a mixture of 30 ml of tetrahydrofuran and 30 ml of a 0.1M phosphate buffer (pH 7.0) and hydrogenated at room temperature for 2 hours in the presence of 650 mg of 10% w/w palladium-on-charcoal. At the end of this time, the reaction mixture was worked up and purified in a similar manner to that described in Example 1-(2) to afford 289 mg of the title compound.

Ultraviolet Absorption Spectrum (H$_2$O) λ$_{max}$ nm: 297.0.

Nuclear Magnetic Resonance Spectrum (D$_2$O, 270 MHz) δ ppm: 0.95 (3H, triplet, J=7.15 Hz); 1.02 (3H, doublet, J=7.33 Hz); 1.10 (3H, doublet, J=6.23 Hz); 2.17–2.30 (1H, multiplet); 2.81–3.18 (2H, multiplet); 3.05 (3H, singlet); 3.10 (2H, quartet, J=7.33 Hz); 3.11 (3H, singlet); 3.28 (1H, doublet of doublets, J=6.05 & 2.76 Hz); 3.69 (1H, doublet of doublets, J=12.09 & 5.49 Hz); 3.84–4.16 (5H, multiplet).

EXAMPLE 21

(1R, 5S, 6S)-2-[(2S)-1,1-Dimethyl-2-pyrrolidiniummethylthio]-6-[(1R)-1-hydroxyethyl]-1-methyl-1-carbapen-2-em-3-carboxylate 21-(1) The procedure described in Example 7-(1) was repeated, but using 1.1 g of (2S)-1,1-dimethyl-4-(4-methoxybenzylthiomethyl)pyrrolidinium fluorosulfonate (prepared as described in Preparation 14), 3.3 ml of anisole, 11.6 ml of trifluoroacetic acid and 581 μl of trifluorosulfonic acid, to afford 666 mg of a crude (2S)-1,1-dimethyl-4-mercaptomethylpyrrolidinium salt as an oil.

21-(2) 76 μl of diisopropylethylamine and 90 μl of diphenylphosphoryl chloride were added simultaneously, whilst ice-cooling, to a solution of 150 mg of 4-nitrobenzyl (1R, 5R, 6S)-6-[(1R)-1-hydroxyethyl]-1-methyl-2-oxo-1-carbapenam-3-carboxylate dissolved in 3 ml of dry acetonitrile, and the mixture was stirred at the same temperature for 1 hour. At the end of this time, 87 μl of diisopropylethylamine and a solution of 148 mg of the salt prepared as described in step (1) in 2 ml of dry acetonitrile were added to the mixture, whilst ice-cooling, and the mixture was allowed to stand at 0° to 5° C. for 2 hours and then for 1 day in a refrigerator. At the end of this time, the reaction mixture was poured into diethyl ether cooled to −78° C. and was washed by decantation. The resulting crude product was dissolved in a mixture of 13 ml of tetrahydrofuran and 13 ml of a 0.1M phosphate buffer (pH 7.0) and hydrogenated at room temperature for 2 hours in the presence of 210 mg of 10% w/w palladium-on-charcoal. Insoluble materials were removed by filtration with the assistance of a Celite filter aid and the filtrate was concentrated by evaporation under reduced pressure. The residue was subjected to column chromatography through CHP-20P (Mitsubishi Chemicals Industries, Ltd.) and fractions eluted with a 5% by volume aqueous acetone solution were collected, concentrated by evaporation under reduced pressure and lyophilized. The resulting crude product was subjected to column chromatography through a column packed with Dowex SOW-X4 (Dow Chemicals Co.) and fractions eluted with water were collected, concentrated by evaporation under reduced pressure and lyophilized. The resulting crude product was further purified using a Lobar column RP-8 (Merck) and 45 mg of the title compound were obtained from the fractions eluted with a 8% by volume aqueous methanolic solution.

Ultraviolet Absorption Spectrum ($H_2O$) $\lambda_{max}$ nm: 297.

Nuclear Magnetic Resonance Spectrum ($D_2O$, 270 MHz) $\delta$ ppm: 1.04 (3H, doublet, J=7.33 Hz); 1.11 (3H, doublet, J=6.60 Hz); 1.70-2.08 (3H, multiplet); 2.35-2.56 (1H, multiplet); 2.70 (1H, doublet of doublets, J=13.18 & 10.99 Hz); 2.77 (3H, singlet); 3.04 (3H, singlet); 3.08-3.60 (6H, multiplet); 4.04-4.09 (2H, multiplet).

EXAMPLE 22

(1R, 5S, 6S)-2-(2R)-1,1-Dimethyl-2-pyrrolidiniummethylthio]-6-(1R)-1-hydroxyethyl]-1-methyl-1-carbapen-2-em-3-carboxylate Following a procedure similar to that described in Example 21, but using 0.94 g of (2R)-1,1-dimethyl-4-(4-methoxybenzylthiomethyl)pyrrolidinium fluorosulfonate (prepared as described in preparation 15) [in step (1)] and 470 mg of 4-nitrobenzyl (1R, 5R, 6S)-6-[(1R)-1-hydroxyethyl]-1-methyl-2-oxo-1-carbapenem-3-carboxylate [in step (2)]. 70 mg of the title compound were obtained.

Ultraviolet Absorption Spectrum ($H_2O$) $\lambda_{max}$ nm: 297.

Nuclear Magnetic Resonance Spectrum ($D_2O$, 270 MHz) $\delta$ ppm: 1.01 (3H, doublet, J=7.33 Hz); 1.10 (3H, doublet, J=6.23 Hz); 1.69-2.08 (3H, multiplet); 2.28-2.45 (1H, multiplet); 2.79 (3H, singlet); 2.94-3.12 (2H, multiplet); 3.07 (3H, singlet); 3.18-3.64 (5H, multiplet); 4.01-4.11 (2H, multiplet).

EXAMPLE 23

(1R, 5S, 6S)-2-[(2S, 4S)-2-Carbamoyl-1-(2-hydroxyethyl)-1-methylpyrrolidinium-4-ylthio]-6-[(1R)-1-hydroxyethyl]-1-methyl-1-carbapen-2-em-3-carboxylate Following a procedure similar to that described in Example 7, but using 0.37 g of (2S, 4S)-2-carbamoyl-1-(2-hydroxyethyl)-4-(4-methoxybenzylthio)-1-methyl-pyrrolidinium fluorosulfonate (prepared as described in preparation 16) [in step (1)] and 260 mg of -nitrobenzyl (1R, 5R, 6S)-6-[(1R)-1-hydroxyethyl]-1-methyl-2-oxo-1-carbapenam-3-carboxylate [in step (2)], 17 mg of the title compound were obtained.

Ultraviolet Absorption Spectrum ($H_2O$) $\lambda_{max}$ nm: 298.

EXAMPLE 24

(1R, 5S, 6S)-2-(1-Methylquinuclidinium-3-ylthio)-6-(1R)-1-hydroxyethyl]-1-methyl-1-carbapen-2-em-3-carboxylate 24-(1) The procedure described in Example 7-(1) was repeated, but using 1.08 g of 3-(4-methoxybenzylthio)-1-methylquinuclidinium fluorosulfonate (prepared as described in preparation 17), 3.12 ml of anisole, 15 ml of trifluoroacetic acid and 278 μl of trifluoromethanesulfonic acid, to afford 880 mg of a crude 3-mercapto-1-methylquinuclidinium salt as an oil.

24-(2) 135 μl of diisopropylethylamine and 160 μl of diphenylphosphoryl chloride were added simultaneously to a solution of 268 mg of 4-nitrobenzyl (1R, 5R, 6S)-6-[(1R)-1-hydroxyethyl]-1-methyl-2-oxo-1-carbapenam-3-carboxylate dissolved in 3 ml of dry acetonitrile, and the mixture was stirred at the same temperature for 1 hour. At the end of this time, 185 μl of diisopropylethylamine and a solution of 271 mg of the salt prepared as described in step (1) dissolved in 2 ml of dry acetonitrile were added to the reaction mixture. The procedure described in Example 21-(2) was then repeated, to afford 35 mg of the title compound.

Ultraviolet Absorption Spectrum ($H_2O$) $\lambda_{max}$ nm: 297.

Nuclear Magnetic Resonance Spectrum ($D_2O$, 270 MHz) $\delta$ ppm: 1.02 (3H, doublet, J=7.32 Hz); 1.10 (3H, doublet, J=6.60 Hz); 1.66-2.32 (5H, multiplet); 2.80 (3H, singlet); 2.98-3.36 (7H, multiplet); 3.57-3.73 (2H, multiplet); 4.00-4.12 (2H, multiplet).

1 EXAMPLE 25

(1R, 5S, 6S)-2-(6S, 8S)-1,4-Dimethyl-5-oxo-4-aza-1-azoniabicyclo[4,3,0]-non-8-ylthio]-6-[(1R)-1-hydroxyethyl]-1-methyl-1-carbapen-2-em-3-carboxylate 25-(1) The procedure described in Example 7-(1) was repeated, but using 841 mg of (6S, 8S)-1,4-dimethyl-8-(4-methoxybenzylthio)-5-oxo-4-aza-1-azoniabicyclo[4.3.0]nonane fluorosulfonate (prepared as described in preparation 18), 2.17 ml of anisole, 7.70 ml of trifluoroacetic acid and 386 μl of trifluoromethanesulfonic acid, to afford 700 mg of a crude (6S, 8S)-1,4-dimethyl-8-mercapto-5-oxo-4-aza-1-azoniabicyclo[4.3.0]nonane salt as an oil.

Nuclear Magnetic Resonance Spectrum ($D_2O$, 270 MHz) $\delta$ ppm: 2.18 (1H, doublet of triplets, J=13.92 & 9.16 Hz); 2.85 (3H, singlet); 2.86-3.04 (1H, multiplet); 3.16 (3H, singlet); 3.51-3.90 (6H, multiplet); 3.98 (1H, doublet of doublets, J=12.09, 7.69 Hz); 4.26 (1H, triplet, J=8.61 Hz).

25-(2) 183 μl of diisopropylethylamine and 218 μl of diphenylphosphoryl chloride were added simultaneously, whilst ice-cooling, to a solution of 362 mg of 4-nitrobenzyl (1R, 5R, 6S)-6-[(1R)-1-hydroxyethyl]-1-methyl-2-oxo-1-carbapenam-3-carboxylate dissolved in 5 ml of dry acetonitrile, and the mixture was stirred at the same temperature for 1 hour. At the end of this time, 209 μl of diisopropylethylamine and a solution of 420 mg of the salt prepared as described in step (1) in 3 ml of dry acetonitrile were added to the mixture, whilst ice-cooling, and then the procedure described in Example 20-(2) was repeated to afford 195 mg of the title compound.

Ultraviolet Absorption Spectrum ($H_2O$) $\lambda_{max}$ nm: 295.2.

Nuclear Magnetic Resonance Spectrum (D₂O, 270 MHz) δ ppm: 1.02 (3H, doublet, J=7.33 Hz); 1.10 (3H, doublet, J=6.59 Hz); 2.23-2.37 (1H, multiplet); 2.86 (3H, singlet); 2.96-3.14 (2H, multiplet); 3.20 (3H, singlet); 3.31 (1H, doublet of doublets, J=5.86, 2.93 Hz); 3.47-3.80 (4H, multiplet); 3.83-4.12 (5H, multiplet); 4.34 (1H, triplet, J=7.88 Hz).

EXAMPLE 26

(1R, 5S, 6S, )-2-[(2RS, 4S)-1,1-Dimethyl-2-methoxycarbonylpyrrolidinium-4-ylthio]-6[(1R)-1-hydroxyethyl]-1-methyl-1-carbapen-2-em-3-carboxylate Following a method similar to that described in Example 1, but using (2S, 4S)-1,1-dimethyl-4-(4-methoxybenzylthio)-2-methoxycarbonylpyrrolidinum fluorosulfonate (prepared by a similar process to that described in Preparations 1 to 4), the title compound was obtained.

Ultraviolet Absorption Spectrum (H₂)) λ$_{max}$ nm: 298.

Nuclear Magnetic Resonance Spectrum (D₂O, 270 MHz) δ ppm: 1.02, 1.03 (3H, doublet, J=7.33 Hz); 1.10 (3H, doublet, J=6.23 Hz); 2.27-2.45 (1H, multiplet); 2.83-2.45 (3H, multiplet); 3.01, 3.14 (3H, singlet); 3.19, 3.22 (3H, singlet); 3.53-3.77 (1H, multiplet); 3.69 (3H, singlet); 3.88-4.12 (4H, multiplet); 4.48 (0.5H, doublet of doublets, J=11.35 & 7.69 Hz); 4.65 (0.5H, doublet of doublets, J=10.44 & 8.61 Hz).

EXAMPLE 27

(1R, 5S, 6S)-2-[(2R, 4S)-1,1-Dimethyl-2-(N,N-dimethylarbamoyl)pyrrolidinium-4-ylthio)-6-(1R)-1-hydroxyethyl]-1-methyl-1-carbapen-2-em-3-carboxylate Following a method similar to that described in Example 4, but using (2R, 4S)-1,1-dimethyl-2-(N,N-dimethylcarbamoyl)-4-(4-methoxybenzylthio)pyrrolidinium fluorosulfonate (prepared as described in preparation the title compound was obtained.

Ultraviolet Absorption Spectrum (H₂O) λ$_{max}$ nm: 297.

Nuclear Magnetic Resonance Spectrum (D₂O, 270 MHz) 1.02 (3H, doublet, J=7.33 Hz); 1.10 (3H, doublet, J=6.22 Hz); 2.28-2.41 (1H, multiplet); 2.68-2.80 (1H, multiplet); 2.82 (3H, singlet); 3.01 (3H, singlet); 3.03 (3H, singlet); 3.05-3.16 (1H, multiplet); 3.18 (3H, singlet); 3.29 (1H, doublet of doublets, J=6.23 & 2.94 Hz); 3.50-3.58 (1H, multiplet) 4.01-4.18 (4H, multiplet); 4.91 (1H, doublet of doublets, J=7.69 & 6.23 Hz).

EXAMPLE 28

(1R, 5S, 6S)-2-[(2R, 4S)-2-Carbamoyl-1,1-dimethylpyrrolidinium-4-ylthio]-6-(1R)-1-hydroxyethyl]-1-methyl-1-carbapen-2-em-3-carboxylate Following a method similar to that described in Example 1, but using (2R, 4S)-2-carbamoyl-4-(4-methoxybenzylthio)-1,1-dimethylpyrrolidinium fluorosulfonate (prepared as described in preparation 22), the title compound was obtained.

Ultraviolet Absorption Spectrum (H₂O) λ$_{max}$ nm: 297.

Nuclear Magnetic Resonance Spectrum (D₂O, 270 MHz) δ ppm: 1.03 (3H, doublet, J=6.96 Hz); 1.10 (3H, doublet, J=6.22Hz); 2.28-2.41 (1H, multiplet); 2.74-2.88 (1H, multiplet); 3.02 (3H, singlet); 3.07-3.18 (1H, multiplet); 3.22 (3H, singlet); 3.29 (1H, doublet of doublets, J=6.23 & 2.57 Hz); 3.52-3.63 (1H, multiplet) 3.98-4.17 (4H, multiplet); 4.39 (1H, triplet, J=8.06 Hz).

EXAMPLE 29

1R, 5S, 6S)-2-[(2S, 4S)-2-Cyclopropylcarbamoyl-1,1-dimethylpyrrolidinium-4-ylthio1-6-(1R)-1-hydroxyethyl]-1-methyl-1-carbapen-2-em-3-carboxylate Following a method similar to that described in Example 3, but using (2S, 4S)-2-cyclopropylcarbamoyl-1,1-dimethyl-4-(4-methoxybenzylthio)pyrrolidinium fluorosulfonate (prepared as described in preparation the title compound was obtained.

Ultraviolet Absorption Spectrum (H₂O) λ$_{max}$ nm: 297.

Nuclear Magnetic Resonance Spectrum (D₂O, 270 MHz) δ ppm: 0.37-0.42 (2H, multiplet); 0.59-0.64 (2H, multiplet); 1.01 (3H, doublet, J=7.32 Hz); 1.09 (3H, doublet, J=6.23 Hz); 2.17-2.29 (1H, multiplet); 2.47-2.55 (1H, multiplet); 2.80-3.13 (2H, multiplet); 3.05 (3H, singlet); 3.09 (3H, singlet); 3.28 (1H, doublet of doublets, J=6.05 & 2.75 Hz); 3.69 (1H, doublet of doublets, J=12.09 & 6.05 Hz); 3.84-4.10 (5H, multiplet).

EXAMPLE 30

(1R, 5S, 6S)-2-(1,1-Dimethylazetidinium-3-ylthio]-6-(1R)-1-hydroxyethyl]-1-methyl-1-carbapen-2-em-3-carboxylate Following a method similar to that described in Example 5, but using 1,1-dimethyl-4-(4-methoxybenzylthio)azetidinium fluorosulfonate, the title compound was obtained.

Ultraviolet Absorption Spectrum (H₂O) λ$_{max}$ nm: 297.

EXAMPLE 31

(1R, 5S, 6S)-2-(4,4-Dimethylmorpholinium-2-ylmethylthio)-6-(1R)-1-hydroxyethyl]-1-methyl-1-carbapen-2-em-3-carboxylate Following a method similar to that described in Example 5, but using 4,4-dimethyl-2-(4-methoxybenzylthio)methylmorpholinium fluorosulfonate, the title compound was obtained.

Ultraviolet Absorption Spectrum (H₂O) λ$_{max}$ nm: 298.

EXAMPLE 32

(1R, 5S, 6S)-2-[(6S, 8S)-5-Oxo-1-methyl-4-aza-1-azoniabicyclo[4.3.0]non-8-ylthio]-6-[(1R)-1-hydroxyethyl]-1-methyl-1-carbapen-2-em-3-carboxylate Following a method similar to that described in Example 25, but using (6S, 8S)-5-oxo-8-(4-methoxybenzylthio)-1-methyl-4-aza-1-azoniabicyclo[4.3.0]nonane fluorosulfonate (prepared as described in Preparation 25), the title compound was obtained.

Ultraviolet Absorption Spectrum (H₂O), λ$_{max}$ nm: 296.

Nuclear Magnetic Resonance Spectrum (D₂O, 270 MHz) δ ppm: 1.02 (3H, doublet, J=7.33 Hz); 1.09 (3H, doublet, J=6.23Hz); 2.23-2.37 (1H, multiplet); 2.94-3.27 (2H, multiplet); 3.19 (3H, singlet); 3.30 (1H, doublet of doublets, J=6.23 & 2.94 Hz); 3.45-3.93 (5H, multiplet); 3.96–4.13 (4H, multiplet); 4.32 (1H, triplet, J=8.24 Hz).

EXAMPLE 33

Sodium (1R, 5S, 6S)-2-(2-oxo-3-pyrrolidinylthio)-6-(1R)-1-hydroxyethyl]-1-methyl-1-carbapen-2-em-3-carboxylate 126 μl of diisopropylethylamine and 150 μl of diphenylphosphoryl chloride were added, whilst stirring and ice-cooling, to a solution of 250 mg of 4-nitrobenzyl (1R, 5R, 6S)-[(1R)-1-hydroxyethyl]-1-methyl-2-oxo-1-carbapenam-3-carboxylate in 3 ml of dry acetonitrile, and then the mixture was stirred at 0–5° C. for 1 hour. At the end of this time, 288 μl of diisopropylethylamine and a solution of 222 mg of a 1:1 by weight mixture of 3-mercapto-2-pyrrolidinone (prepared by a similar process to that described in Preparation 19) and trifluoromethanesulfonic acid in 2 ml of acetonitrile were added, with ice-cooling, to the previous reaction mixture. The whole mixture was then allowed to stand for 3 days in a refrigerator. At the end of this time, the mixture was diluted with ethyl acetate, washed, in turn, with an aqueous solution of sodium bicarbonate and an aqueous solution of sodium chloride, and then dried over anhydrous magnesium sulfate. The solvent was then distilled off under reduced pressure to leave a crude product, which was dissolved in a mixture of 20 ml of tetrahydrofuran and 20 ml of a 0.1M phosphate buffer solution (pH 7.1), and then hydrogenated at room temperature for 2 hours in the presence of 331 mg of 10% w/w palladium-on-charcoal. At the end of this period, insoluble matter was removed by filtration using a Celite filter aid and the filtrate was washed with diethyl ether. The aqueous phase was concentrated by evaporation under reduced pressure, and the residue was subjected to column chromatography through Diaion HP-20AG, eluted with water. The eluate was concentrated by evaporation under reduced pressure and then lyophilized to give a crude product. This was further purified by Lobar column chromatography (Merck, LiChroprep RP-8, size B), eluted with a 3% by volume aqueous methanol solution. The eluate was concentrated by evaporation under reduced pressure and lyophilized to give 35 mg of the title compound in the form of a colorless powder.

Ultraviolet Absorption Spectrum (H$_2$O) $\lambda_{max}$ nm: 302.

Nuclear Magnetic Resonance Spectrum (D$_2$O, 270 MHz) δ ppm: 1.00 (3H, doublet, J=7.33 Hz); 1.11 (3H, doublet, J=6.60Hz); 1.86–1.98 (1H, multiplet); 2.40–2.55 (1H, multiplet); 3.18–3.39 (4H, multiplet); 3.71 (1H, doublet of doublets, J=9.16 & 6.60 Hz); 4.02–4.12 (2H, multiplet).

EXAMPLE 34

Sodium (1R, 5S, 6S)-2-(2-oxo-4-pyrrolidinylthio)-6-[(1R)-1-hydroxyethyl]-1-methylcarbapen-2-em-3-carboxylate 126 μl of diisopropylethylamine and 150 μl of diphenylphosphoryl chloride were added, whilst stirring and ice-cooling, to a solution of 250 mg of 4-nitrobenzyl (1R, 5R, 6S)-[(1R)-1-hydroxyethyl]-1-methyl-2-oxo-1-carbapenam-3-carboxylate in 5 ml of dry acetonitrile, and then the mixture was stirred at 0°–5° C. for 1 hour. At the end of this time, 144 μl of diisopropylethylamine and 97 mg of 4-mercapto-2-pyrrolidinone (prepared as described in Preparation 20) were added, with ice-cooling, to the previous reaction mixture. The whole mixture was then stirred at 0°–5° C. for 7 hours and then allowed to stand overnight in a refrigerator. At the end of this time, the mixture was diluted with ethyl acetate, washed twice with an aqueous solution of sodium chloride, and then dried over anhydrous magnesium sulfate. The solvent was then distilled off under reduced pressure to leave a crude product, which was dissolved in a mixture of 20 ml of tetrahydrofuran and 20 ml of a 0.1M phosphate buffer solution (pH 7.1), and then hydrogenated at room temperature for 2.5 hours in the presence of 331 mg of 10% w/w palladium-on-charcoal. At the end of this time, insoluble matter was removed by filtration using a Celite filter aid and the filtrate was washed with diethyl ether. The aqueous phase was concentrated by evaporation under reduced pressure, and the residue was subjected to column chromatography through Diaion HP-20AG, eluted with water. The eluate was concentrated by evaporation under reduced pressure and then lyophilized to give a crude product. This was further purified by Lobar column chromatography (Merck, LiChroprep RP-8, size B), eluted with a 3% by volume aqueous methanol solution. The eluate was concentrated by evaporation under reduced pressure and lyophilized to give 91 mg of the title compound in the form of a colorless powder. This is a mixture of the two isomers in respect of the carbon atom at the 4-position of the pyrrolidine ring, in proportions of about 1:1."

Ultraviolet Absorption Spectrum (H$_2$O) $\lambda_{max}$ nm: 300.

Nuclear Magnetic Resonance Spectrum (D$_2$O, 270 MHz) δ ppm: 1.02 & 1.03 (3H, doublet x 2, J=7.33 & 6.96 Hz); 1.10 (3H, doublet, J=6.60 Hz); 2.12 & 2.22 (1H, doublet of doublets x 2, J=17.59 & 4.40 Hz and 17.59 & 4.03 Hz); 2.74 & 2.77 (1H, doublet of doublets x 2, J=17.59 & 9.16 Hz and 17.59 & 9.16 Hz); 3 07–3.29 (3H, multiplet); 3.64–3.73 (1H, multiplet); 3.84–3.96 (1H, multiplet); 4.00–4.12 (2H, multiplet).

EXAMPLE 35

5-Methyl-2-oxo-1,3-dioxolen-4-ylmethyl (1R, 5S, 6S)-2-(2-oxo-3-pyrrolidinylthio)-6-(1R)-1-hydroxyethyl]-1-methyl-1-carbapen-2-em-3-carboxylate A solution of 66 mg of 5-methyl-2-oxo-1,3-dioxolen-4-ylmethyl iodide (prepared by heating 5-methyl-2-oxo-1,3-dioxolen-4-ylmethyl bromide and sodium iodide under reflux in acetone) in chloroform was added to a mixture of 47.6 mg of sodium (1R, 5S, 6S)-2-(2-oxo-3-pyrrolidinylthio)-6-[(1R)-1-hydroxyethyl]-1-methyl-1-carbapen-2-em-3-carboxylate and 0.4 ml of dry dimethylformamide. The mixture was stirred at room temperature for 80 minutes and then at 30°–45° C. for 4.5 hours. At the end of this time, the reaction mixture was diluted with ethyl acetate and washed four times with an aqueous solution of sodium chloride. The extract was dried and the solvent was distilled off under reduced pressure. The residue was purified by Lobar column chromatography (Merck, LiChroprep Si60, size A), eluted with a 10:1 by volume mixture of ethyl acetate and methanol, to give 27.4 mg of the title compound in the form of a colorless powder.

Ultraviolet Absorption Spectrum (CH$_3$OH) $\lambda_{max}$ nm: 322.

Nuclear Magnetic Resonance Spectrum (hexadeuterated dimethyl sulfoxide, 270 MHz) δ ppm: 1.13 (3H, doublet, J=7.32 Hz); 1.15 (3H, doublet, J =6.35

Hz); 1.84–1.98 (1H, multiplet); 2.17 (3H, singlet); 2.50–2.65 (1H, multiplet); 3.12–3.45 (4H, multiplet); 3.77–4.06 (2H, multiplet); 4.14 (1H, doublet of doublets, J=9.27 & 2.44 Hz); 5.08 (2H, singlet).

EXAMPLE 36

Sodium (1R, 5S, 6S)-2-(2-oxo-4-pyrrolidinylthio)-6-[(1R)-1-hydroxyethyl]-1-methyl-1-carbapen-2-em-3-carboxylate 1.45 ml of diisopropylethylamine and 1.70 ml of diphenylphosphoryl chloride were added, whilst ice-cooling, to a solution of 2.93 g of 4-nitrobenzyl bapenam-3-carboxylate in 50 ml of dry acetonitrile, and then the mixture was stirred at 0°–5° C. for 30 minutes. 1.45 ml of diisopropylethylamine and a solution of 1.35 g of 4-mercapto-2-pyrrolidinone (prepared as described in preparation 20) in 5 ml of acetonitrile were added to the mixture, cooled at −20° C., and then the whole mixture was stirred at 0° C. for 3 hours, after which it was allowed to stand at the same temperature overnight. The reaction mixture was then diluted with ethyl acetate, washed twice with an aqueous solution of sodium chloride and filtered. The organic phase was dried over anhydrous sodium sulfate and the solvent was distilled off under reduced pressure to give the 4-nitrobenzyl ester of the title compound as a foam. This was dissolved in 150 ml of tetrahydrofuran and the solution was filtered to remove insoluble matter. 150 ml of a 0.1M phosphate buffer solution (pH 7.1) were added to the filtrate and catalytic reduction was effected at room temperature for 2.5 hours in the presence of 1.5 g of 10% w/w palladium-on-charcoal. The reaction mixture was then worked up in a similar manner to that described in Example 34, to give 1.05 g of the title compound as a colorless powder. This is a mixture of the two isomers in respect of the carbon atom at the 4-position of the pyrrolidine ring, in proportions of about 9:1.

Ultraviolet Absorption Spectrum (H$_2$O) $\lambda_{max}$ nm: 299. Infrared Absorption Spectrum (KBr) $\nu_{max}$ cm$^{-1}$ 1748, 1689, 1597, 1393, 1296.

Nuclear Magnetic Resonance Spectrum (D$_2$O, 270 MHz) δ ppm: 1.03 (3H, doublet, J=7.3 Hz); 1.10 (3H, doublet, J=6.2 Hz); 2.12 (0.9H, doublet of doublets, J=17.9 & 4.4 Hz); 2.22 (0.1H, doublet of doublets, J=17.9 & 4.4 Hz); 2.74, 2.77 (1H, 2 x doublet of doublets, J=17.9 & 8.4 Hz); 3.08–3.24 (2H, multiplet); 3.26 (1H, doublet of doublets, J=5.9 & 2.6 Hz); 3.69 (1H, doublet of doublets, J=11.4 & 6.6 Hz); 3.84–3.93 (1H, multiplet); 4.02–4.11 (2H, multiplet).

EXAMPLE 37

Sodium (1R, 5S, 6S)-2-(2-oxo-4-pyrrolidinylthio)-6-(1R)-1-hydroxyethyl-1-methyl-1-carbapen-2-em-3-carboxylate A crude p-nitrobenzyl ester of the title compound was prepared, following substantially the same procedure as described in Example 36 above but using 330 mg of 4-nitrobenzyl (1R, 5R, 6S)-6-[(1S)-1-hydroxyethyl]-1-methyl-2-oxo-1-carbapenam-3-carboxylate. The ester was subjected to column chromatography through 50 g of silica gel, eluted with a 4:1 by volume mixture of ethyl acetate and methanol. The eluent was concentrated by evaporation under reduced pressure to give 260 mg of a colorless powder, which was mixed with 10 ml of ethyl acetate. This mixture was ice-cooled and filtered to remove insoluble matter. The filtrate was concentrated by evaporation under reduced pressure, and diisopropyl ether was added to the residue to give a precipitate. This was collected by filtration and dried to give 150 mg of the p-nitrobenzyl ester of the title compound as a powder which is either the R- or the S-isomer in respect of the carbon atom at the 4-position of the pyrrolidine ring.

Nuclear Magnetic Resonance Spectrum (hexadeuterated dimethyl sulfoxide, 270 MHz) δ ppm: 1.16 (3H, doublet, J=6.0 Hz); 1.18 (3H, doublet, J=7.3 Hz); 2.02 (1H, doublet of doublets, J=17.1 & 4.9 Hz); 2.72 (1H, doublet of doublets, J=17.1 & 8.3 Hz); 3.12–3.48 (3H, multiplet); 3.74 (1H, doublet of doublets, J=10.7 & 6.3 Hz); 3.94–4.05 (2H, multiplet); 4.24 (1H, doublet of doublets, J=9.8 & 2.9 Hz); 5.06 (1H, doublet, J=4.9 Hz); 5.30, 5.46 (2H, AB, J=14.2 Hz); 7.71 (2H, doublet, J=8.8 Hz); 8.23 (2H, doublet, J=8.8 Hz).

100 mg of the p-nitrobenzyl ester obtained in the previous step were subjected to catalytic hydrogenation in a similar manner to that described in Example 34, to give 55 mg of the title compound having either the R- or the S-configuration, in respect of the carbon atom at the 4-position of the pyrrolidine ring, in a pure state as a powder.

Ultraviolet Absorption Spectrum $\lambda_{max}$ nm: 299 (H$_2$O).

Nuclear Magnetic Resonance Spectrum (D$_2$O, 270 MHz) δ ppm: 1.03 (3H, doublet, J=7.3 Hz); 1.10 (3H, doublet, J=6.2 Hz); 2.12 (1H, doublet of doublets, J=17.9 & 4.4 Hz); 2.74 (1H, doublet of doublets, J=17.9 & 8.4 Hz); 3.08–3.24 (2H, multiplet); 3.26 (1H, doublet of doublets, J=5.9 & 2.6 Hz); 3.69 (1H, doublet of doublets, J=11.4 & 6.6 Hz); 3.84–3.93 (1H, multiplet); 4.02–4.11 (2H, multiplet).

EXAMPLE 38

Sodium (1R, 5S, 6S)-2-(2-oxo-4-pyrrolidinylthio)-6-(1R)-1-hydroxyethyl]-1-methyl-1-carbapen-2-em-3-carboxylate A crude p-nitrobenzyl ester of the title oompound was prepared, following substantially the same procedure as that described in Example 34, but using 300 mg of 4-nitrobenzyl (1R, 5R, 6S)-6-[(1R)-1-hydroxyethyl]-1-methyl-2-oxo-1-carbapenam-3-carboxylate. The ester was subjected to column chromatography through 50 g of silica gel, eluted with a 4:1 by volume mixture of ethyl acetate and methanol. The eluent was concentrated by evaporation under reduced pressure to give 270 mg of a colorless powder. The product is about a 1:1 mixture of the two isomers in respect of the carbon atom at the 4-position of the pyrrolidine ring. 100 mg of this product were mixed with 10 ml of ethyl acetate. The mixture was filtered to collect the insoluble matter, which was recrystallized from a mixture of methanol and isopropanol to give 30 mg of the p-nitrobenzyl ester of the title compound as colorless needles. This is either the R- or the S-isomer in respect of the carbon atom at the 4-position of the pyrrolidine ring and is the other isomer having the opposite configuration of the compound obtained in the first step of Example 37.

Nuclear Magnetic Resonance Spectrum (hexadeuterated dimethyl sulfoxide, 270 MHz) δ ppm: 1.16 (3H, doublet, J=6.3 Hz); 1.17 (3H, doublet, J=7.3 Hz); 2.13 (1H, doublet of doublets, J=17.1 & 4.4 Hz); 2.79 (1H, doublet of doublets, J=17.1 & 7.8 Hz); 3.10 (1H, doublet of doublets, J=10.8, 3.4 Hz); 3.16–3.35 (1H, multiplet); 3.40–3.51 (1H, multiplet); 3.70 (1H, doublet of doublets, J =10.7 & 7.3 Hz); 3.95–4.12 (2H, multiplet); 4.25 (1H, doublet of doublets, J=9.3 & 2.5 Hz);

5.07 (1H, doublet, J=5.4 Hz); 5.30, 5.46 (2H, AB, J=14.2 Hz); 7.71 (2H, doublet, J=8.8 Hz); 8.23 (2H, doublet, J=8.8 Hz).

20 mg of the p-nitrobenzyl ester obtained in the previous step were subjected to catalytic hydrogenation in a similar manner to that described in Example 34, to give 11 mg of the title compound having either the R- or the S-configuration, in respect of the carbon atom at the 4-position of the pyrrolidine ring and having the opposite configuration to that obtained in Example 37, in a pure state as a powder.

Nuclear Magnetic Resonance Spectrum ($D_2O$, 270 MHz) δ ppm: 1.02 (3H, doublet, J=7.3 Hz); 1.10 (3H, doublet, J=6.6 Hz); 2.22 (1H, doublet of doublets, J=17.6 & 4.4 Hz); 2.77 (1H, doublet of doublets, J=17.6 & 8.4 Hz); 3.08-3.25 (2H, multiplet); 3.25 (1H, doublet of doublets, J=5.9 & 2.6 Hz); 3.68 (1H, doublet of doublets, J=11.4 & 6.4 Hz); 3.84-3.96 (1H, multiplet); 4.00-4.12 (2H, multiplet).

EXAMPLE 39

Pivaloyloxymethyl (1R, 5S, 6S)-2-(2-oxo-4-pyrrolidinylthio)-6-[(1R)-1-hydroxyethyl]-1-methyl-1-carbapen-2-em-3-carboxylate 100 mg of sodium 2-(2-oxo-4-pyrrolidinylthio)-6-[(1R)-1-hydroxyethyl]-1-methyl-1-carbapen-2-em-3-carboxylate obtained by a similar procedure to that described in Example 36 were suspended in 3 ml of dry N,N-dimethylacetamide. 80 μl of pivaloyloxymethyl iodide were added, whilst ice-cooling, to the suspension, and then the mixture was stirred for 15 minutes, during which time the mixture became a solution. The reaction mixture was then diluted with 50 ml of ethyl acetate and washed twice with an aqueous solution of sodium chloride. The organic phase was dried over anhydrous sodium sulfate and the solvent was distilled off under reduced pressure. The residue was purified by Lobar column chromatography (Merck, LiChroprep RP-8, size B), eluted with 60% by volume aqueous methanol. The eluent was evaporated under reduced pressure to remove the methanol, leaving the aqueous phase, which was mixed with sodium chloride and then extracted with ethyl acetate. The extract was dried over anhydrous sodium sulfate and concentrated by evaporation under reduced pressure to give 110 mg of the title compound as a colorless powder.

Ultraviolet Absorption Spectrum (CH CN) $\lambda_{max}$ nm: 323 (ε=10760).

Infrared Absorption Spectrum (KBr) $\nu_{max}$ cm$^{-1}$: 1778, 1756, 1699.

Nuclear Magnetic Resonance Spectrum (CDCl$_3$, 270 MHz) δ ppm: 1.23 (9H, singlet); 1.29 (3H, doublet, J=7.3 Hz); 1.35 (3H, doublet, J=6.2 Hz); 1.95 (1H, broad singlet); 2.33 (1H, doublet of doublets, J=17.6 & 6.2 Hz); 2.79 (1H, doublet of doublets, J=17.6 & 8.8 Hz); 3.22-3.34 (2H, multiplet); 3.38 (1H, doublet of doublets, J=9.9 & 4.8 Hz); 3.80 (1H, doublet of doublets, J=10.3 & 7.0 Hz); 3.95-4.05 (1H, multiplet); 4.20-4.27 (2H, multiplet); 5.79 (1H, broad singlet); 5.83, 5.97 (2H, AB, J=5.5 Hz).

EXAMPLE 40

(1-Methylcyclohexan-1-yl)carbonyloxymethyl (1R, 5S, 6S)-2-(2-oxo-4-pyrrolidinylthio)-6-[(1R)-1-hydroxyethyl]-1-methyl-1-carbapen-2-em-3-carboxylate Following a similar procedure to that described in Example 39, but using (1-methylcyclohexan-1-yl)carbonyloxymethyl iodide in place of pivaloyloxymethyl iodide, the title compound was obtained.

Ultraviolet Absorption Spectrum (CH$_3$CN) $\lambda_{max}$ nm: 323 (ε=9655).

Infrared Absorption Spectrum (KBr) $\nu_{max}$ cm$^{-1}$: 777, 1753, 1700.

Nuclear Magnetic Resonance Spectrum (CDCl$_3$, 270 MHz) δ ppm: 1.18 (3H, singlet); 1.29 (3H, doublet, J=7.3 Hz); 1.35 (3H, doublet, J=6.2 Hz); 1.25-1.75 (9H, multiplet); 2.00-2.08 (2H, multiplet); 2.33 (1H, doublet of doublets, J=17.6 & 6.2 Hz); 2.79 (1H, doublet of doublets, J=17.6 & 8.8 Hz); 3.21-3.33 (2H, multiplet); 3.38 (1H, doublet of doublets, J=9.9 & 4.8 Hz); 3.79 (1H, doublet of doublets, J=9.9 & 7.0 Hz); 3.95-4.05 (1H, multiplet); 4.21-4.30 (2H, multiplet); 5.78 (1H, broad singlet); 5.87, 5.96 (2H, AB, J=5.5 Hz).

EXAMPLE 41

1-(Cyclohexyloxycarbonyloxy)ethyl (1R, 5S, 6S)-2-(2-oxo-4-pyrrolidinylthio)-6-[(1R)-1-hydroxyethyl]-1-methyl-1-carbapen-2-em-3-carboxylate Following a procedure similar to that described in Example 39, but using 54 mg of sodium 2-(2-oxo-4-pyrrolidinylthio)-6-[(1R)-1-hydroxyethyl]-1-methyl-1-carbapen-2-em-3-carboxylate obtained by a similar procedure to that described in Example 36 and 50 μl of 1-(cyclohexyloxycarbonyloxy)ethyl iodide, 62 mg of the title compound were obtained as a colorless powder.

Ultraviolet Absorption Spectrum (CH$_3$CN) $\lambda_{max}$ nm: 323 (ε=10766).

Infrared Absorption Spectrum (KBr) $\nu_{max}$ cm$^{-1}$: 1759, 1701.

Nuclear Magnetic Resonance Spectrum (CDCl$_3$, 270 MHz) δ ppm: 1.28 (3H, doublet, J=7.0 Hz); 1.33, 1.36 (3H, two doublets, J=6.2 Hz); 1.59, 1.61 (3H, two doublets, J=5.5 Hz); 1.2-1.6 (6H, multiplet); 1.7-2.0 (5H, multiplet); 2.33 (1H, doublet of doublets, J=17.6 & 6.2 Hz); 2.79 (1H, doublet of doublets, J=17.6 & 8.8 Hz); 3.24-3.33 (2H, multiplet); 3.35-3.42 (1H, multiplet); 3.76-3.85 (1H, multiplet); 3.94-4.05 (1H, multiplet); 4.19-4.27 (2H, multiplet); 4.59-4.70 (1H, multiplet); 5.69 (1H, broad singlet); 6.88 (1H, quartet, J=5.5 Hz).

EXAMPLE 42

1-(Cyclopentyloxycarbonyloxy)ethyl (1R, 5S, 6S)-2-(2-oxo-4-pyrrolidinylthio)-6-[(1R)-1-hydroxyethyl]-1-methyl-1-carbapen-2-em-3-carboxylate Following a procedure similar to that described in Example 39, but using 1-(cyclopentyloxycarbonyloxy)ethyl iodide, the title compound was obtained.

Ultraviolet Absorption Spectrum (CH$_3$CN) $\lambda_{max}$ nm: 322 (ε=10651).

Infrared Absorption Spectrum (KBr) $\nu_{max}$ cm$^{-1}$: 1760, 1701.

Nuclear Magnetic Resonance Spectrum (CDCl$_3$, 270 MHz) 1.28, 1.29 (3H, two doublets, J=7.3 Hz); 1.33, 1.35 (3H, two doublets, J=6.2 Hz); 1.58, 1.60 (3H, two doublets, J=5.5 Hz); 1.65-1.95 (8H, multiplet); 2.33 (1H, doublet of doublets, J=17.6 & 6.2 Hz); 2.79 (1H, doublet of doublets, J=17.6 & 8.8 Hz); 3.23-3.32 (2H, multiplet); 3.38, 3.39 (1H, two doublet of doublets, J=9.9 & 4.8 Hz); 3.68-3.87 (1H, multiplet); 3.96-4.07 (1H, multiplet); 4.19-4.27 (2H, multiplet); 5.08-5.16 (1H, multiplet); 5.66 (1H, broad singlet); 6.87 (1H, quartet, J=5.5 Hz).

EXAMPLE 43

1-(Cyclohexylmethyloxycarbonyloxy)ethyl (1R, 5S, 6S)-2-(2-oxo-4-pyrrolidinylthio)-6-(1R)-1-hydroxyethyl]-1-methyl-1-carbapen-2-em-3-carboxylate Following a procedure similar to that described in Example 39, but using 1-(cyclohexylmethyloxycarbonyloxy)ethyl iodide, the title compound was obtained.

Ultraviolet Absorption Spectrum (CH$_3$CN) $\lambda_{max}$ nm: 323 ($\epsilon$ = 10975).

Infrared Absorption Spectrum (KBr) $\nu_{max}$ cm$^{-1}$: 766, 1700, 1269.

Nuclear Magnetic Resonance Spectrum (CDCl$_3$, 270 MHz) δ ppm: 0.95-1.26 (5H, multiplet); 1.28, 1.29 (3H, two doublets, J=7.3 Hz); 1.33, 1.35 (3H, two doublets, J=6.2 Hz); 1.59, 1.61 (3H, two doublets, J=5.9 & 5.5 Hz); 1.64-1.76 (6H, multiplet); 1.87 (1H, broad singlet); 2.33 (1H, doublet of doublets, J=17.6 & 6.2 Hz); 2.79 (1H, doublet of doublets, J=17.6 & 8.8 Hz); 3.24-3.35 (2H, multiplet); 3.37-3.42 (1H, multiplet); 3.75-3.87 (1H, multiplet); 3.95-4.06 (3H, multiplet); 4.20-4.28 (2H, multiplet); 5.73 (1H, broad singlet); 6.86, 6.87 (1H, two quartets, J=5.9 & 5.5 Hz).

EXAMPLE 44

1-(Isopropoxycarbonyloxy)ethyl (1R, 5S, 6S)-2-(2-oxo-4-pyrrolidinylthio)-6-[(1R)-1-hydroxyethyl]-1-methyl-1-carbapen-2-em-3-carboxylate Following a procedure similar to that described in Example 39, but using 1-(isopropoxycarbonyloxy)ethyl iodide, the title compound was obtained.

Ultraviolet Absorption Spectrum (CH$_3$CN) $\lambda_{max}$ nm: 323 ($\epsilon$ = 10961).

Infrared Absorption Spectrum (KBr) $\nu_{max}$ cm$^{-1}$: 762, 1701, 1272.

Nuclear Magnetic Resonance Spectrum (CDCl$_3$, 270 MHz) 1.26-1.36 (12H, multiplet); 1.59, 1.61 (3H, two doublets, J=5.5 Hz); 1.80 (1H, broad triplet, J=3.7 Hz); 2.33 (1H, doublet of doublets, J=17.6 & 6.2 Hz); 2.79 (1H, doublet of doublets, J=17.6 & 8.8 Hz); 3.24-3.34 (2H, multiplet); 3.35-3.42 (1H, multiplet); 3.76-3.87 (1H, multiplet); 3.95-4.07 (1H, multiplet); 4.19-4.28 (2H, multiplet); 4.82-4.99 (1H, multiplet); 5.63 (1H, broad singlet); 6.88 (1H, quartet, J=5.5 Hz).

EXAMPLE 45

(1R, 2S, 5R)-(l)-Menthyloxycarbonyloxymethyl (1R, 5S, 6S)-2-(2-oxo-4-pyrrolidinylthio)-6-(1R)-1-hydroxyethyl]-1-methyl-1-carbapen-2-em-3-carboxylate Following a procedure similar to that described in Example 39, but using (1R, 2S, 5R)-(l)-menthyloxycarbonyloxymethyl iodide, the title compound was obtained.

Ultraviolet Absorption Spectrum (CH$_3$CN) $\lambda_{max}$ nm: 324 ($\epsilon$ = 10801).

Infrared Absorption Spectrum (KBr) $\nu_{max}$ cm$^{-1}$: 763, 1695, 1266.

Nuclear Magnetic Resonance Spectrum (CDCl$_3$, 270 MHz) δ ppm: 0.78 (3H, doublet, J=7.0 Hz); 0.89 (3H, doublet, J=7.0 Hz); 0.92 (3H, doublet, J=7.3 Hz); 1.29 (3H, doublet, J=7.3 Hz); 1.35 (3H, doublet, J=6.2 Hz); 0.95-1.55 (5H, multiplet); 1.63-1.73 (2H, multiplet); 1.88-2.03 (1H, multiplet); 2.08-2.17 (1H, multiplet); 2.34 (1H, doublet of doublets, J=17.2 & 6.2 Hz); 2.79 (1H, doublet of doublets, J=17.2 & 8.8 Hz); 3.22-3.34 (2H, multiplet); 3.39 (1H, doublet of doublets, J=9.5 & 4.8 Hz); 3.74-3.86 (1H, multiplet); 3.96-4.06 (1H, multiplet); 4.18-4.28 (2H, multiplet); 4.56 (1H, doublet of triplets, J=10.6 & 4.4 Hz); 5.70 (1H, broad singlet); 5.89, 5.91 (2H, AB, J=5.9 Hz).

EXAMPLE 46

5-Methyl-2-oxo-1,3-dioxolen-4-ylmethyl (1R, 5S, 6S)-2-(2-oxo-4-pyrrolidinylthio)-6-(1R)-1-hydroxyethyl]-1-methyl-1-carbapen-2-em-3-carboxylate Following a procedure similar to that described in Example 39, but using 50 mg of sodium 2-(2-oxo-4-pyrrolidinylthio)-6-[(1R)-1-hydroxyethyl]-1-methyl-1-carbapen-2-em-3-carboxylate and 55 mg of 5-methyl-2-oxo-1,3-dioxolen-4-ylmethyl bromide, 50.mg of the title compound were obtained as a colorless powder.

Ultraviolet Absorption Spectrum (CH$_3$CN) $\lambda_{max}$ nm: 321.1 ($\epsilon$ = 8982).

Infrared Absorption Spectrum (CHCl$_3$) $\nu_{max}$ cm$^{-1}$: 1820, 1772, 1701, 1627.

Nuclear Magnetic Resonance Spectrum (CDCl$_3$, 270 MHz) δ ppm: 1.30 (3H, doublet, J=7.33 Hz); 1.36 (3H, doublet, J=6.22 Hz); 1.80 (1H, broad singlet); 2.21 (3H, singlet); 2.35 (1H, doublet of doublets, J=17.58 & 6.04 Hz); 2.81 (1H, doublet of doublets, J=17.58 & 8.80 Hz); 3.25-3.43 (3H, multiplet); 3.73-4.05 (2H, multiplet); 4.17-4.32 (2H, multiplet); 4.96, 5.05 (2H, AB, J=13.93 Hz); 5.59 (1H, broad singlet).

EXAMPLES 47 TO 56

EXAMPLE 47

1-(Isobutyryloxy)ethyl (1R, 5S, 6S)-2-(2-oxo-4-pyrrolidinylthio)-6-[(1R)-1-hydroxyethyl]-1-methyl-1-carbapen-2-em-3-carboxylate Ultraviolet Absorption Spectrum (CH CN) $\lambda_{max}$ nm:

EXAMPLE 48

1-(Cyclohexanecarbonyioxy)ethyl (1R, 5S, 6S)-2-(2-oxo-4-pyrrolidinylthio)-6-[(1R)-1-hydroxyethyl]-1-methyl-1-carbapen-2-em-3-carboxylate Ultraviolet Absorption Spectrum (CH$_3$CN) $\lambda_{max}$ nm:

EXAMPLE 49

1-(Pivaloyloxy)ethyl (1R, 5S, 6S)-2-(2-oxo-4-pyrrolidinylthio)-6-(1R)-1-hydroxyethyl]-1-methyl-1-carbapen-2-em 3-carboxylate Ultraviolet Absorption Spectrum (CH$_3$CN) $\lambda_{max}$ nm: 323.

EXAMPLE 50

1-Acetoxyethyl (1R, 5S, 6S)-2-(2-oxo-4-pyrrolidinyl-thio)-6-[(1R)-1-hydroxyethyl]-1-methyl-1-carbapen-2-em-carboxylate Ultraviolet Absorption Spectrum (CH$_3$CN) $\lambda_{max}$ nm: 323.

EXAMPLE 51

Cyclohexanecarbonyloxymethyl (1R, 5S, 6S)-2-(2-oxo-4-pyrrolidinylthio)-6-(1R)-1-hydroxyethyl]-1-methyl-1-carbapen-2-em-3-carboxylate Ultraviolet Absorption Spectrum (CH$_3$CN) $\lambda_{max}$ nm: 323.

EXAMPLE 51

Cyclohexyloxycarbonyloxymethyl (1R, 5S, 6S)-2-(2-oxo-4-pyrrolidinylthio)-6-[(1R)-1-hydroxyethyl]-1-methyl-1-carbapen-2-em-3-carboxylate Ultraviolet Absorption Spectrum (CH$_3$CN) $\lambda_{max}$ nm: 323.

EXAMPLE 53

Cyclopentyloxycarbonyloxymethyl (1R, 5S, 6S)-2-(2-oxo-4-pyrrolidinylthio)-6-[(1R)-1-hydroxyethyl]-1-methyl-1-carbapen-2-em-3-carboxylate Ultraviolet Absorption Spectrum (CH CN) $\lambda_{max}$ nm: 323.

EXAMPLE 54

Sodium (1R, 5S, 6S)-2-(1-methyl-2-oxo-4-pyrrolidinyl-thio)-6-(1R)-1-hydroxyethyl]-1-methyl-1-carbapen-2-em--carboxylate Ultraviolet Absorption Spectrum (CH$_3$CN) $\lambda_{max}$ nm: 300.

EXAMPLE 55

Pivaloyloxymethyl (1R, 5S, 6S)-2-(1-methyl-2-oxo-4-pyrrolidinylthio)-6-[(1R)-1-hydroxyethyl)-1-methyl-1-carbapen-2-em-3-carboxylate Ultraviolet Absorption Spectrum (CH$_3$CN) $\lambda_{max}$ nm: 23.

EXAMPLE 56

1-(Isopropoxycarbonyloxy)ethyl (1R, 5S, 6S)-2-(1-methyl-2-oxo-4-pyrrolidinylthio)-6-[(1R)-1-hydroxyethyl]-1-methyl-1-carbapen-2-em-3-carboxylate Ultraviolet Absorption Spectrum (CH$_3$CN) $\lambda_{max}$ nm: 323.

PREPARATION 1

(2S, 4S)-2-Carbamoyl-4-(4-methoxybenzylthio)-1,1-dimethylpyrrolidinium fluorosulfonate

1-(1) (2S, 4R)-1-t-Butoxycarbonyl-4-hydroxy-2-pyrrolidinecarboxylic acid 27.3 g of sodium hydroxide were dissolved in 380 ml of water, and 85 g of (2S, 4R)-4-hydroxy-2-pyrrolidinecarboxylic acid were then added to the solution at 3 to 5° C. followed by 570 ml of tetrahydrofuran at the same temperature. A solution of 141.5 g of di-t-butoxy carbonate in 190 ml of tetrahydrofuran was then added to the reaction mixture at 3° to 5° C., and then the mixture was stirred at 50° to 55° C. for 2 hours. At the end of this time, the mixture was cooled, and then its pH was adjusted to a value of 3 to 4 by the addition of concentrated hydrochloric acid followed by ammonium chloride. The mixture was then extracted with tetrahydrofuran and the extract was dried. The solvent was then distilled from the extract under reduced pressure, giving 128 g of the title compound as a colorless powder.

Nuclear Magnetic Resonance Spectrum (CDCl$_3$, 60 MHz) δ ppm: 1.44 (9H, singlet); 1.96–2.45 (2H, multiplet); 2.36–2.72 (2H, multiplet); 4.24–4.66 (2H, multiplet); 5.04–5.60 (2H, broad singlet).

1-(2) (2S, 4R)-1-t-Butoxycarbonyl-2-carbamoyl-4-hydroxypyrrolidine 58 g of (2S, 4R)-1-(t-butoxycarbonyl)-4-hydroxy-2-pyrrolidinecarboxylic acid [prepared as described in step (1) above] were dissolved in 850 ml of dry tetrahydrofuran, and then 38.2 ml of triethylamine were added to the mixture at −15° to −20° C. A solution of 26.3 ml of ethyl chloroformate in 240 ml of dry tetrahydrofuran was then added dropwise to the mixture at −15° to −20° C., and the mixture was stirred at the same temperature for 35 minutes. At the end of this time, 258 ml of 28% w/v aqueous ammonium hydroxide were added to the mixture at −15° to −20° C., and the mixture was allowed to stand overnight at room temperature. Ammonium chloride was then added to the reaction mixture, which was then extracted with tetrahydrofuran. The extract was dried and freed from the solvent by distillation under reduced pressure. The resulting residue was triturated with diethyl ether to cause crystallization. The crystals were collected by filtration and washed with diethyl ether to afford 49.7 g of the title compound as colorless crystals, melting at 146°–148° C.

Nuclear Magnetic Resonance Spectrum (hexadeuterated dimethyl sulfoxide, 60 MHz) δ ppm: 1.38 (9H, singlet); 1.65–2.24 (2H, multiplet); 3.00–3.66 (2H, multiplet); 3.76–4.49 (3H, multiplet); 6.78 (1H, broad singlet); 7.23 (1H, broad singlet).

1-(3) (2S, 4R)-1-(t-Butoxycarbonyl)-2-carbamoyl-4-methanesulfonyloxypyrrolidine 1.85 ml of methanesulfonyl chloride was added, whilst ice-cooling, to a solution of 5.0 g of (2S, 4R)-1-(t-butoxycarbonyl)-2-carbamoyl-4-hydroxypyrrolidine [prepared as described in step (2) above] in 250 ml of dry tetrahydrofuran, followed by 3.31 ml of triethylamine. The mixture was then stirred at 0° to 5° C. for 1 hour, after which it was poured into an aqueous solution of sodium chloride and extracted with ethyl acetate. The extract was washed with an aqueous solution of sodium chloride and dried over anhydrous magnesium sulfate, and the solvent was removed by distillation under reduced pressure. The residue was purified by chromatography through silica gel (eluted with a 9:1 by volume mixture of ethyl acetate and methanol) to afford 5.5 g of the title compound as colorless crystals.

Nuclear Magnetic Resonance Spectrum (CDCl$_3$, 60 MHz) δ ppm: 1.43 (9H, singlet); 2.10–2.68 (2H, multiplet); 3.12 (3H, singlet); 3.10–3.40 (1H, broad singlet); 3.73 (2H, doublet, J=4.0 Hz); 4.32 (1H, triplet, J=7.0 Hz); 5.26 (1H, triplet, J=4.0 Hz); 6.68 (1H, broad singlet); 7.30 (1H, broad singlet).

1-(4) (2S, 4R)-1-(t-Butoxycarbonyl)-2-carbamoyl-4-(4-methoxybenzylthio)pyrrolidine 330 mg of sodium hydride (as a 55% w/w dispersion in mineral oil) were added, whilst ice-cooling, to a solution of 1.18 g of p-methoxybenzyl mercaptan in 25 ml of dry dimethylformamide, and the mixture was stirred at room temperature for 30 minutes. At the end of this time, 2.14 g of (2S, 4R)-1-(t-butoxycarbonyl)-2-carbamoyl-4-methanesulfonyloxypyrrolidine [prepared as described in step (3) above] were added to the mixture, which was then stirred at room temperature for 3 hours.

The reaction mixture was then poured into an aqueous solution of sodium chloride and extracted with ethyl acetate. The extract was washed with an aqueous solution of sodium chloride and dried over anhydrous magnesium sulfate, and the solvent was removed by distillation under reduced pressure. The residue was purified by chromatography through silica gel (eluted with a 2:3 by volume mixture of cyclohexane and ethyl acetate) to afford 1.94 g of the title compound as an oil.

Nuclear Magnetic Resonance Spectrum (CDCl$_3$, 60 MHz) δ ppm: 1.43 (9H, singlet); 1.80–3.42 (5H, multiplet); 3.70 (2H, singlet); 3.78 (3H, singlet); 4.18 (1H, triplet, J=7.0 Hz); 5.96 (1H, broad singlet); 6.35 (1H, broad singlet); 6.79, 7.21 (4H, A J=9.0 Hz).

1-(5) (2S, 4S)-2-Carbamoyl-4-(4-methoxybenzylthio)-pyrrolidine 1.92 g of (2S, 4S)-1-(t-butoxycarbonyl)-2-carbamoyl-4-(4-methoxybenzylthio)pyrrolidine [prepared as described in step (4) above] was dissolved in 25 ml of ethyl acetate, and 26.2 ml of a 4N dioxane solution of hydrogen chloride were added to the solution, whilst ice-cooling. The mixture was then stirred at 0° to 5° C. for 2 hours and at room temperature for 30 minutes. At the end of this time, it was poured into a saturated aqueous solution of sodium bicarbonate, to make it weakly basic, and was extracted with ethyl acetate. The extract was washed with an aqueous solution of sodium chloride and dried over anhydrous magnesium sulfate. The solvent was then removed by distillation under reduced pressure, to give 1.36 g of the title compound as a powder, melting at 120°–121° C.

Nuclear Magnetic Resonance Spectrum (hexadeuterated dimethyl sulfoxide, 60 MHz) δ ppm: 1.58–3.40 (7H, multiplet); 1.67 (2H, singlet); 1.78 (3H, singlet); 6.43 (1H, broad singlet); 6.78, 7.22 (4H, A$_2$B$_2$, J=9.0 Hz); 7.31 (1H, broad singlet).

1-(5a) (2S, 4S)-2-Carbamoyl-4-(4-methoxybenzylthio)-pyrrolidine hydrochloride 620 ml of a 4N solution of hydrogen chloride in ethyl acetate were added, whilst ice-cooling, to a solution of 91 g of (2S, 4S)-1-t-butoxycarbonyl-2-carbamoyl-4-(4-methoxybenzylthio)pyrrolidine [prepared as described in step (4) above] in 2 l of ethyl acetate, and then the mixture was stirred at room temperature for 4.5 hours. The crystals which precipitated were collected by filtration, washed with diethyl ether and dried in vacuo, to give 63 g of the title compound melting at 192°–195° C.

Infrared Absorption Spectrum (KBr) $\nu_{max}$ cm$^{-1}$: 1706, 1584, 1512.

Nuclear Magnetic Resonance Spectrum (D$_2$O, 270 MHz) δ ppm: 1.75–1.90 (1H, multiplet); 2.54–2.62 (1H, multiplet); 3.04–3.11 (1H, multiplet); 3.28–3.41 (2H, multiplet); 3.64 (2H, singlet); 3.65 (3H, singlet); 4.22 (1H, triplet, J=8.06 Hz); 6.80, 7.15 (4H, A$_2$B$_2$, J =8.79 Hz).

1-(6a) (2S, 4S)-2-Carbamoyl-4-(4-methoxybenzylthio)-1-methyl-pyrrolidine

A solution of 0.29 g of sodium bicarbonate in 3 ml of water and 0.34 ml of 35% formalin were added dropwise in that order, whilst ice-cooling, to a suspension of 1 g of the compound obtained as described in step 1-(5a) in 20 ml of acetonitrile, and then the mixture was stirred at 10° C. for 20 minutes. 0.25 g of sodium cyanoborohydride was then added to the mixture, whilst ice-cooling, and then the mixture was stirred at room temperature for 20 minutes. 0.5 ml of acetic acid was added, whilst ice-cooling, to the mixture, which was then stirred at room temperature for 20 minutes. At the end of this time, the mixture was diluted with 100 ml of ethyl acetate and washed, in turn, with a 1:1 by volume mixture of a 1N aqueous solution of sodium hydroxide and a saturated aqueous solution of sodium chloride and then with a saturated aqueous solution of sodium chloride. The organic phase was then dried over anhydrous magnesium sulfate and the solvent was distilled off under reduced pressure. The residue was purified by column chromatography through silica gel (Wakogel C-100, Wako Junyaku), eluted with a 95:5 by volume mixture of chloroform and methanol, to give 0.92 g of the title compound. The melting point, infrared absorption spectrum and the nuclear magnetic resonance spectrum of this compound coincided with those of the compound obtained as described in preparation 1-(6), below.

1-(6) (2S, 4S)-2-Carbamoyl-4-(4-methoxybenzylthio)-1-methyl-pyrrolidine 0.07 ml of methyl iodide was added, whilst ice-cooling, to a solution of 0.6 g of (2S, 4S)-2-carbamoyl-4-(4-methoxybenzylthio)pyrrolidine [prepared as described in step (5) above] dissolved in 4.5 ml of dry dimethylformamide. The mixture was then stirred at 0° to 5° C. for 5 minutes and at room temperature for 20 minutes. At the end of this time, the reaction mixture was poured into a saturated aqueous solution of sodium bicarbonate and then extracted with ethyl acetate. The extract was washed with an aqueous solution of sodium chloride and dried over anhydrous magnesium sulfate. The solvent was removed by distillation under reduced pressure, and then the residue was subjected to column chromatography using a Lobar column (Merck, Li-Chroprep Si 60, size B), and 252 mg of the title compound, melting at 113°–114° C., were obtained as crystals from the fractions eluted with a 9:1 by volume mixture of ethyl acetate and methanol.

Infrared Absorption Spectrum (KBr) $\nu_{max}$ cm$^{-1}$: 1636, 1609, 1512.

Nuclear Magnetic Resonance Spectrum (CDCl$_3$, 60 MHz) δ ppm: 1.58–3.36 (6H, multiplet); 2.35 (3H, singlet); 3.68 (2H, singlet); 3.78 (3H, singlet); 5.95 (1H, broad singlet); 6.84, 7.23 (4H, A$_2$B$_2$, J=9.0 Hz); 7.20 (1H, broad singlet).

1-(7) (2S, 4S)-2-Carbamoyl-4-(4-methoxybenzylthio)-1,1-dimethylpyrrolidinium fluorosulfonate 0.123 ml of methyl fluorosulfonate was added, whilst ice-cooling, to a solution of 320 mg of (2S, 4S)-2-carbamoyl-4-(4-methoxybenzylthio)-1-methylpyrrolidine [prepared as described in step (6) or (6a) above] dissolved in 7 ml of dry methylene chloride. The mixture was then stirred at the same temperature for 20 minutes and at room temperature for 2 hours. At the end of this time, the solvent was removed by distillation under reduced pressure, and the residue was repeatedly washed by decantation with diethyl ether and then dried under reduced pressure to afford 525 mg of the title compound as an oil.

Nuclear Magnetic Resonance Spectrum (D$_2$O, 270 MHz) δ ppm: 2.01–3.68 (5H, multiplet); 3.02 (3H, singlet); 3.03 (3H, singlet); 3.65 (3H, singlet); 3.68 (2H, singlet); 4.07 (1H, doublet of doublets, J=8.43 & 7.70 Hz); 6.81, 7.16 (4H, A$_2$B$_2$, J=8.79 Hz).

PREPARATION 2

(2S, 4S)-2-Carbamoyl-4-(4-methoxybenzylthio)-1-(2-fluoroethyl)-1-methylpyrrolidinium fluorosulfonate 2-(1) (2S, 4S)-2-Carbamoyl-4-(4-methoxybenzylthio)-1-(2-fluoroethyl)pyrrolidine 0.4 ml of 1-bromo-2-fluoroethane, 3.83 g of sodium iodide and 0.38 g of sodium bicarbonate were added to a solution of 1.2 g of (2S, 4S)-2-carbamoyl-4-(4-methoxybenzylthio)pyrrolidine dissolved in 12 ml of dry dimethylformamide, whilst ice-cooling, and the mixture was stirred at room temperature for 20 minutes and then at 40° C. for 20 hours. At the end of this time, the reaction mixture was poured into a saturated aqueous solution of sodium bicarbonate and extracted with ethyl acetate. The extract was washed with a saturated aqueous solution of sodium chloride and dried over anhydrous magnesium sulfate. The solvent was then removed by distillation under reduced pressure, and the residue was subjected to column chromatography through silica gel (Katayama Chemicals Industries Co., silica gel 60K070). 838 mg of the title compound, melting at 122°–123° C., were obtained as a powder from those fractions eluted with ethyl acetate.

Infrared Absorption Spectrum (KBr) $\nu_{max}$ cm$^{-1}$: 1636, 1610, 1510

Nuclear Magnetic Resonance Spectrum (CDCl$_3$, 60 MHz) δ ppm: 1.55–3.40 (8H, multiplet); 3.69 (2H, singlet); 3.79 (3H, singlet); 4.47 (2H, doublet of triplets, J=47.0 & 6.0 Hz); 4.78 (1H, broad singlet); 7.02 (4H, A2B2, J=9.0 Hz); 6.95–7.50 (1H, broad singlet).

2-(2) (2S, 4S)-2-Carbamoyl-4-(4-methoxybenzylthio)-1-(2-fluoroethyl)-1-methylpyrrolidinium fluorosulfonate 0.17 ml of methyl fluorosulfonate was added, whilst ice-cooling, to a solution of 630 mg of (2S, 4S)-2-carbamoyl-4-(4-methoxybenzylthio)-1-(2-fluoroethyl)-pyrrolidine [prepared as described in step (1) above] dissolved in 12 ml of dry methylene chloride. The mixture was stirred at the same temperature for 30 minutes and then at room temperature for 5 hours. At the end of this time, the solvent was removed by distillation under reduced pressure, and the residue was washed repeatedly by decantation with diethyl ether and dried under reduced pressure to afford 850 mg of the title compound as an oil.

Nuclear Magnetic Resonance Spectrum (D$_2$O, 270 MHz) δ ppm: 1.84–4.73 (10H, multiplet); 3.18 (3H, singlet); 3.65 (3H, singlet); 3.68 (2H, singlet); 6.79–7.19 (4H, multiplet).

PREPARATION 3

(2S, 4S)-1,1-Dimethyl-2-methylcarbamoyl-4-(4-methoxybenzylthio)pyrrolidinium fluorosulfonate 3-(1) (2S, 4R)-1-(t-Butoxycarbonyl)-2-methylcarbamoyl-4-hydroxypyrrolidine 9.91 ml of triethylamine were added at −40° C. to a solution of 15.03 g of (2S, 4R)-1-(t-butoxycarbonyl)-4-hydroxy-2-pyrrolidinecarboxylic acid dissolved in 250 ml of dry tetrahydrofuran, and then a solution of 6.81 ml of ethyl chloroformate in 30 ml of dry tetrahydrofuran was added at −30° to −40° C. to the resulting mixture, which was then stirred at the same temperature for 1 hour. 16.82 ml of a 40% by volume aqueous methylamine solution were then added at −30° C., and the temperature of the reaction mixture was allowed to rise to room temperature; the reaction was then allowed to continue for 1 hour. At the end of this time, the reaction mixture was mixed with a small amount of an aqueous solution of sodium chloride and extracted thrice with ethyl acetate. The combined extracts were washed with an aqueous solution of sodium chloride and dried over anhydrous magnesium sulfate. The solvent was then removed by distillation under reduced pressure, giving 12.76 g of the title compound as a colorless oil.

Nuclear Magnetic Resonance Spectrum (CDCl$_3$, 60 MHz) δ ppm: 1.44 (9H, singlet); 1.89–2.45 (2H, multiplet); 2.81 (3H, doublet, J=5.0 Hz); 3.23–3.71 (3H, multiplet); 4.12–4.68 (2H, multiplet); 6.70 (1H, broad singlet).

3-(2) (2S, 4R)-1-(t-Butoxycarbonyl)-4-methanesulfonyloxy-2-methylcarbamoylpyrrolidine 7.11 ml of triethylamine were added, whilst ice-cooling, to a solution of 11.29 g of (2S, 4R)-1-(t-butoxycarbonyl)-2-methylcarbamoyl-4-hydroxypyrrolidine [prepared as described in step (1) above] dissolved in 120 ml of dry tetrahydrofuran, and then 3.93 ml of methanesulfonyl chloride were added to the resulting mixture, and the mixture was stirred at 0° to 5° C. for 30 minutes and then at 15° C. for 30 minutes. It was then poured into an aqueous solution of sodium chloride and extracted with ethyl acetate. The extract was washed with an aqueous solution of sodium chloride and dried over anhydrous magnesium sulfate. The solvent was then removed by distillation under reduced pressure, giving 11.58 g of the title compound as colorless crystals.

Nuclear Magnetic Resonance Spectrum (CDCl$_3$, 60 MHz) δ ppm: 1.46 (9H, singlet); 2.00–2.85 (2H, multiplet); 2.81 (3H, doublet, J=5.0 Hz); 3.03 (3H, singlet); 3.41–5.42 (4H, multiplet); 6.75 (1H, broad singlet).

3-(3) (2S, 4S)-1-(t-Butoxycarbonyl)-4-(4-methoxybenzylthio)-2-methylcarbamoylpyrrolidine 1.80 g of sodium hydride (as a 55% w/w dispersion in mineral oil) was added, whilst ice-cooling, to a solution of 5.70 ml of 4-methoxybenzyl mercaptan dissolved in 100 ml of dry tetrahydrofuran, and the mixture was then stirred at 0° to 5° C. for 30 minutes. At the end of this time, a solution of 11.00 g of (2S, 4R)-1-(t-butoxycarbonyl)-4-methanesulfonyloxy-2-methyl-carbamoylpyrrolidine [prepared as described in step (2) above] in 80 ml of dry dimethylformamide was added to the mixture, and the mixture was stirred at 34° C. for 4.5 hours. The reaction mixture was then poured into an aqueous solution of sodium chloride and extracted with ethyl acetate. The extract was washed with an aqueous solution of sodium chloride and dried over anhydrous magnesium sulfate. The solvent was then removed by distillation under reduced pressure. The residue was purified by column chromatography through silica gel (eluted with a 5:1 by volume mixture of ethyl acetate and hexane) to afford 4.35 g of the title compound as an oil.

Nuclear Magnetic Resonance Spectrum (CDCl$_3$, 60 MHz) δ ppm: 1.42 (9H, singlet); 1.80-4.40 (6H, multiplet); 2.81 (3H, doublet, J=5.0 Hz); 3.70 (2H, singlet); 3.79 (3H, singlet); 6.39 (1H, broad singlet); 6.87, 7.26 (4H, A2B2, J=9.0 Hz).

3-(4) (2S, 4S)-4-[4-Methoxybenzylthio)-2-methyl-carbamoylpyrrolidine 52.5 ml of a 4N dioxane solution of hydrogen chloride were added, whilst ice-cooling, to a solution of 4.00 g of (2S, 4S)-1-(t-butoxycarbonyl)-4-(4-methoxybenzylthio)-2-methylcarbamoylpyrrolidine [prepared as described in step (3) above] dissolved in 50 ml of ethyl acetate. The mixture was stirred at 0° to 5° C. for 30 minutes and then at room temperature for 2 hours. At the end of this time, the reaction mixture was poured into a saturated aqueous solution of sodium bicarbonate to make it weakly basic, and it was then extracted with ethyl acetate. The aqueous layer was saturated with ammonium chloride and then extracted with tetrahydrofuran. The extract was washed with an aqueous solution of sodium chloride and dried over anhydrous magnesium sulfate, and the solvent was removed by distillation under reduced pressure. The residue was purified by column chromatography through silica gel (eluted with a 5:1 mixture by volume of ethyl acetate and methanol), to afford 2.34 g of the title compound as colorless crystals, melting at 53°-54° C.

Nuclear Magnetic Resonance Spectrum (CDCl$_3$, 60 MHz) δ ppm: 1.42-3.89 (6H, multiplet); 2.74 (3H, doublet, J=5.0 Hz); 3.66 (2H, singlet); 3.76 (3H, singlet); 6.79, 7.17 (4H, A2B2, J=9.0 Hz); 7.03-7.75 (2H, multiplet).

3-(5) (2S, 4S)-4-(4-Methoxybenzylthio)-1-methyl-2-methylcarbamoylpyrrolidine 244 μl of methyl iodide and 300 mg of sodium bicarbonate were added, whilst ice-cooling, to a solution of 1.00 g of (2S, 4S)-4-(4-methoxybenzylthio)-2-methylcarbamoylpyrrolidine [prepared as described in step (4) above] dissolved in 6 ml of dry dimethylformamide. The mixture was then stirred at 0° to 5° C. for 1 hour and allowed to stand overnight at room temperature. At the end of this time, the reaction mixture was poured into an aqueous solution of sodium chloride and extracted with ethyl acetate. The extract was washed with an aqueous solution of sodium chloride and dried over anhydrous magnesium sulfate. The solvent was then removed by distillation under reduced pressure, and the residue was purified by column chromatography through silica gel (eluted with a 10:1 by volume mixture of ethyl acetate and methanol), to afford 222 mg of the title compound as colorless crystals, melting at 82°-84° C.

Infrared Absorption Spectrum (KBr) ν$_{max}$ cm$^{-1}$: 1655, 1512, 1251

Nuclear Magnetic Resonance Spectrum (CDCl$_3$, 60 MHz) δ ppm: 1.45-3.91 (6H, multiplet); 2.31 (3H, singlet); 2.80 (3H, doublet, J=5.0 Hz); 3.66 (2H, singlet); 3.77 (3H, singlet); 6.81, 7.20 (4H, A2B2, J=9.0 Hz), 6.85-7.60 (1H, multiplet).

3-(6) (2S, 4S)-1,1-Dimethyl-2-methylcarbamoyl-4-(4-methoxybenzylthio)pyrrolidinium fluorosulfate 280 μl of methyl fluorosulfonate were added, whilst ice-cooling, to a solution of 210 mg of (2S, 4S)-4-(4-methoxybenzylthio)-1-methyl-2-methyl-carbamoylpyrrolidine [prepared as described in step (5) above] dissolved in 30 ml of dry methylene chloride. The mixture was stirred at the same temperature for 30 minutes and then at room temperature for 5 hours. At the end of this time, the solvent was removed by distillation under reduced pressure, and the residue was washed repeatedly by decantation with diethyl ether and dried under reduced pressure, to afford 281 mg of the title compound as a colorless powder.

Infrared Absorption Spectrum (KBr) ν$_{max}$ cm$^{-1}$: 1681, 1512, 1248

Nuclear Magnetic Resonance Spectrum (D$_2$O, 270 MHz) δ ppm: 1.95-2.43 (2H, multiplet); 2.62 (3H, singlet); 2.61-3.88 (3H, multiplet); 3.03 (3H, singlet); 3.10 (3H, singlet); 3.65 (3H, singlet); 3.68 (2H, singlet); 4.12 (1H, triplet, J=8.06 Hz); 6.83, 7.12 (4H, A2B2, J=8.61Hz).

PREPARATION 4
(2S, 4S)-1,1-Dimethyl-2-(N,N-dimethylcarbamoyl)-4-(4-methoxybenzylthio)pyrrolidinium fluorosulfonate

4-(1) (2S, 4R)-1-(t-Butoxycarbonyl)-2-(N,N-dimethyl-carbamoyl)-4-hydroxypyrrolidine 3.84 ml of triethylamine was added, at −15° to −20° C., to a solution of 5.8 g of (2S, 4R)-1-(t-butoxycarbonyl)-4-hydroxy-2-pyrrolidinecarboxylic acid dissolved in 85 ml of dry tetrahydrofuran, and then a solution of 2.63 ml of ethyl chloroformate in 25 ml of dry tetrahydrofuran was added to the resulting mixture at the same temperature. The reaction mixture was then stirred for 2 hours, after which 19.75 ml of 50% by volume aqueous dimethylamine was added to it at −20° to −25° C. The mixture was then stirred for 3 hours under ice cooling, after which it was allowed to stand overnight at room temperature. At the end of this time, the mixture was poured into a mixture of 30 ml of concentrated hydrochloric acid and ice and extracted with ethyl acetate. The extract was washed with an aqueous solution of sodium chloride and dried. The solvent was then removed by distillation under reduced pressure, and the residue was purified by column chromatography through silica gel (eluted with a 9:1 by volume mixture of ethyl acetate and methanol) to afford 429 mg of the title compound.

Nuclear Magnetic Resonance Spectrum (CDCl$_3$, 60 MHz) δ ppm: 1.42 (9H, singlet); 1.86-2.34 (2H, multiplet); 2.58-2.95 (1H, multiplet); 2.97 (3H, singlet); 3.10 (3H, singlet); 3.43-3.74 (2H, multiplet); 4.36-5.00 (2H, multiplet).

4-(2) (2S, 4R)-1-(t-Butoxycarbonyl)-2-(N,N-dimethyl-carbamoyl)-4-methanesulfonyloxypyrrolidine 297 μl of methanesulfonyl chloride, followed by 537 μl of triethylamine, were added, whilst ice-cooling, to a solution of 993 mg of (2S, 4R)-1-(t-butoxyoarbonyl)-2-(N,N-dimethylcarbamoyl)-4-hydroxypyrrolidine [prepared as described in step (1) above] dissolved in 20 ml of dry tetrahydrofuran. The mixture was stirred at 0° to 5° C. for 1 hour and then at room temperature for 1 hour. At the end of this time, it was treated and purified according to the procedure described in preparation 1-(3), to afford 1.05 g of the title compound as a colorless oil.

Nuclear Magnetic Resonance Spectrum (CDCl$_3$, 60 MHz) δ ppm: 1.43 (9H, singlet); 2.15-2.60 (2H, multiplet); 2.97 (3H, singlet); 3.07 (3H, singlet); 3.10, 3.13 (together 3H, each singlet); 3.83 (2H, doublet, J=4.0 Hz); 4.63-5.03 (1H, multiplet); 5.15-5.46 (1H, multiplet).

4-(3) (2S, 4S)-1-(t-Butoxycarbamoyl)-2-(N,N-dimethyl-carbamoyl)-4-(4-methoxybenzylthio)pyrrolidine 151 mg of sodium hydride (as a 55% w/w dispersion in mineral oil) were added, whilst ice-cooling, to a solution of 532 mg of 4-methoxybenzyl mercaptan dissolved in 10 ml of dry dimethylformamide. The mixture was then stirred at room temperature for 30 minutes, after which 1.05 g of (2S, 4R)-1-(t-butoxycarbonyl)-2-(N,N-dimethylcarbamoyl)-4-methanesulfonyl-oxypyrrolidine [prepared as described in step (2) above] was added. The reaction mixture was then stirred at room temperature for 30 minutes and then at 40° C. for 6 hours. At the end of this time, it was treated and purified according to the procedure described in preparation 1-(4), to afford 385 mg of the title compound as an oil.

Infrared Absorption Spectrum (liquid film) ν$_{max}$ cm$^{-1}$: 1690, 1660, 1605, 1585, 1515.

Nuclear Magnetic Resonance Spectrum (CDCl$_3$, 60 MHz) δ ppm: 1.35 and 1.38 (9H, singlet); 1.55-3.37 (5H, multiplet); 2.93 (3H, singlet); 3.00 (3H, singlet); 3.68 (2H, singlet); 3.77 (3H, singlet); 4.30-4.75 (1H, multiplet); 6.85, 7.25 (4H, A B , J=9.0 Hz).

4-(4) (2S, 4S)-2-(N,N-Dimethylcarbamoyl)-4-(4-methoxybenzylthio)pyrrolidine 1 ml of a 4N dioxane solution of hydrogen chloride was added, whilst ice-cooling, to a solution of 385 mg of (2S, 4S)-1-(t-butoxycarbonyl)-2-(N,N-dimethylcarbamoyl)-4-(4-methoxybenzylthio)pyrrolidine [prepared as described in step (3) above] dissolved in 1 ml of ethyl acetate, and the mixture was stirred at room temperature for 1.5 hours. At the end of this time, the reaction mixture was poured into a saturated aqueous solution of sodium bicarbonate to make it weakly basic, and it was extracted with ethyl acetate. The extract was washed with an aqueous solution of sodium chloride and dried over anhydrous magnesium sulfate. The solvent was then removed by distillation under reduced pressure, and the residue was purified by column chromatography through silica gel (eluted with a 1:2 by volume mixture of ethyl acetate and methanol), to afford 163 mg of the title compound as an oil.

Infrared Absorption Spectrum (liquid film) δ$_{max}$ cm$^{-1}$: 3300, 1604, 1605, 1590, 1510.

Nuclear Magnetic Resonance Spectrum (CDCl$_3$, 60 MHz) δ ppm: 1.21-1.78 (2H, multiplet); 2.09-3.98 (5H, multiplet); 2.94 (6H, singlet); 3.64 (2H, singlet); 3.74 (3H, singlet); 6.81, 7.21 (4H, A$_2$B$_2$, J=9.0 Hz).

4-(5) (2S, 4S)-2-(N,N-Dimethylcarbamoyl)-4-(4-methoxybenzylthio)-1-methylpyrrolidine 84 mg of sodium bicarbonate and 41 μl of methyl iodide were added, whilst ice-cooling, to a solution of 163 mg of (2S, 4S)-2-(N,N-dimethylcarbamoyl)-4-(4-methoxybenzylthio)pyrrolidine [prepared as described in step (4) above] dissolved in 1.5 ml of dry dimethylformamide, and the mixture was stirred at room temperature for 4 hours. At the end of this time, the reaction mixture was poured into a saturated aqueous solution of sodium bicarbonate and extracted with ethyl acetate. The extract was washed with an aqueous solution of sodium chloride and dried over anhydrous magnesium sulfate. The solvent was then removed by distillation under reduced pressure, and the residue was purified by chromatography using a Lobar column (Merck, LiChroprep Si60, size A). 45 mg of the title compound were obtained, as an oil, from the fractions eluted with a 3:1 by volume mixture of ethyl acetate and methanol.

Infrared Absorption Spectrum (liquid film) δ$_{max}$ cm$^{-1}$: 1640, 1607, 1580, 1510.

Nuclear Magnetic Resonance Spectrum (CDCl$_3$, 60 MHz) δ ppm: 1.56-2.18 (2H, multiplet); 2.20-3.60 (4H, multiplet); 2.34 (3H, singlet); 2.96 (3H, singlet); 3.10 (3H, singlet); 3.70 (2H. singlet); 3.78 (3H, singlet); 6.82, 7.22 (4H, A$_2$B$_2$, J=9.0Hz).

4-(6) Methyl 1-(t-butoxycarbonyloxy)-4-hydroxyprolinate 2.2 g of sodium hydride (as a 55% w/w dispersion in mineral oil) were added, at 0° to 5° C., to a solution of 1.15 g of 1-(t-butoxycarbonyl)-4-hydroxyproline dissolved in 100 ml of dry dimethylformamide. The mixture was then stirred at room temperature for 1.5 hours, after which it was cooled to 0° to 5° C., and 3.42 ml of methyl iodide were added to it. The reaction mixture was then allowed to stand overnight at room temperature. At the end of this time, it was poured into a saturated aqueous solution of sodium chloride and extracted with ethyl acetate. The extract was washed with an aqueous solution of sodium chloride and dried, after which the solvent was removed by distillation under reduced pressure, and the residue was purified by column chromatography through silica gel (eluted with a 1:1 by volume mixture of benzene and ethyl acetate) to afford 6.1 g of the title compound as an oil.

Infrared Absorption Spectrum (liquid film) δ$_{max}$ cm$^{-1}$: 3430, 1750, 1700, 1670.

Nuclear Magnetic Resonance Spectrum (CDCl$_3$, 60 MHz) δ ppm: 1.41 (9H, singlet); 1.78-2.84 (3H, multiplet); 3.58 (2H, doublet, J=4.0 Hz); 3.71 (3H, singlet); 4.18-4.62 (2H, multiplet).

4-(7) (2S, 4R)-1-(t-Butoxycarbonyl)-4-methanesulfonyl-oxy-2-methoxycarbonylpyrrolidine 2.02 ml of methanesulfonyl chloride, followed by 3.65 ml of triethylamine were added, whilst ice-cooling, to a solution of 6.1 g of methyl 1-(t-butoxycarbonyl)-4-hydroxyprolinate [prepared as described in step (6) above] dissolved in 120 ml of dry tetrahydrofuran. The mixture was stirred first at 0° to 5° C. for 1 hour and then at room temperature for 1 hour, after which it was poured into an aqueous solution of sodium chloride and extracted with ethyl acetate. The extract was washed with an aqueous solution of sodium chloride and dried over anhydrous magnesium sulfate. The solvent was then removed by distillation under reduced pressure, to afford 8.13 g of the title compound as an oil.

Nuclear Magnetic Resonance Spectrum (CDCl$_3$, 60 MHz) δ ppm: 1.47 (9H, singlet); 1.74–2.85 (2H, multiplet); 3.08 (3H, singlet); 3.79 (3H, singlet); 3.81 (2H, doublet. J=4.0 Hz); 4.15–4.65 (1H. multiplet); 5.12–5.41 (1H, multiplet).

4-(8) (2S, 4S)-1-(t-Butoxycarbonyl-4-(4-methoxybenzyl-thio)-2-methoxycarbonylpyrrolidine 1.11 g of sodium hydride (as a 55% w/w dispersion in mineral oil) was added, whilst ice-cooling, to a solution of 3.51 ml of 4-methoxybenzyl mercaptan dissolved in 60 ml of dry dimethylformamide, and the mixture was stirred at room temperature for 30 minutes. At the end of this time, a solution of 8.13 g of (2S, 4R)-1-(t-butoxycarbonyl)-4-methanesulfonyloxy-2-methoxycarbonylpyrrolidine [prepared as described in step (7) above] in 20 ml of dry dimethylformamide was added dropwise to the mixture, which was then stirred at room temperature for 15 minutes and then at 40° C. for 4 hours. The reaction mixture was then poured into an aqueous solution of sodium chloride and extracted with ethyl acetate. The extract was washed with water, dried and freed from the solvent by distillation under reduced pressure. The residue was purified by column chromatography through silica gel (eluted with a 15:1 by volume mixture of benzene and ethyl acetate), to afford 6.89 g of the title compound as an oil.

Infrared Absorption Spectrum (liquid film) ν$_{max}$ cm$^{-1}$: 1745, 1690, 1605, 1580, 1510

Nuclear Magnetic Resonance Spectrum (CDCl$_3$, 50 MHz) δ ppm: 1.40 (9H, singlet); 1.71–3.48 (5H, multiplet); 3.71 (3H, singlet); 3.78 (2H, singlet); 4.01–4.45 (1H, multiplet); 6.85, 7.25 (4H, A$_2$B$_2$, J=9.0 Hz).

4-(9( (2S, 4S)-4-(4-Methoxybenzylthio)-2-methoxycarbonylpyrrolidine 27.3 ml of a 4N ethyl acetate solution of hydrogen chloride were added, whilst ice-cooling, to a solution of 5.22 g of (2S, 4S)-1-(t-butoxycarbonyl)-4-(4-methoxybenzylthio)-2-methoxycarbonylpyrrolidine [prepared as described in step (8) above] dissolved in 14 ml of ethyl acetate, and the mixture was stirred at room temperature for 1 hour. The reaction mixture was then poured into a saturated aqueous solution of sodium bicarbonate and extracted with ethyl acetate. The extract was washed with an aqueous solution of sodium chloride and dried over anhydrous magnesium sulfate. The solvent was then removed by distillation under reduced pressure, to give 3.3 g of the title compound as an oil.

Infrared Absorption Spectrum (liquid film) ν$_{max}$ cm$^{-1}$: 3250, 1735, 1610, 1580, 1510.

Nuclear Magnetic Resonance Spectrum (CDCl$_3$, 60 MHz) δ ppm: 1.56–3.32 (6H, multiplet); 3.67 (2H, singlet); 3.72 (3H, singlet); 3.78 (3H, singlet); 3.70–3.99 (1H, multiplet).

4-(10) (2S, 4S)-4-(4-Methoxybenzylthio)-2-methoxycarbonyl-1-methylpyrrolidine 1.18 g of sodium bicarbonate and 0.876 ml of methyl iodide were added, whilst ice-cooling, to a solution of 3.3 g of (2S, 4S)-4-(4-methoxybenzylthio)-2-methoxycarbonypyrrolidine [prepared as described in step (9) above] dissolved in 30 ml of dry dimethylformamide, and the mixture was stirred at room temperature for 5 hours. At the end of this time, the reaction mixture was poured into a saturated aqueous solution of sodium bicarbonate and extracted with ethyl acetate. The extract was washed with an aqueous solution of sodium chloride and dried over anhydrous magnesium sulfate. The solvent was removed by distillation under reduced pressure. The residue was purified by column chromatography over silica gel (eluted with a 1:1 by volume mixture of ethyl acetate and benzene), to afford 968 mg of the title compound as an oil.

Infrared Absorption Spectrum (liquid film) ν$_{max}$ cm$^{-1}$: 1740, 1730, 1605, 1580, 1510.

Nuclear Magnetic Resonance Spectrum (CDCl$_3$, 60 MHz) δ ppm: 1.64–3.34 (6H, multiplet); 2.37 (3H, singlet); 3.70 (2H, singlet); 3.81 (3H, singlet); 3.88 (3H, singlet); 6.83, 7.23 (4H, A B$_2$. J=9.0 Hz).

4-(11) (2S, 4S)-2-(N,N-Dimethylcarbamoyl)-4-(4-methoxybenzyl-thio)-1-methylpyrrolidine 1.92 ml of a 1N aqueous solution of sodium hydroxide was added to a solution of 378 mg of (2S, 4S)-4-(4-methoxybenzylthio)-2-methoxycarbonyl-1-methylpyrrolidine [prepared as described in step (10) above] dissolved in 3.84 ml of methanol, and the mixture was stirred at room temperature for 3 hours. At the end of this time, the mixture was neutralized by the addition of 1.92 ml of 1N aqueous hydrochloric acid. The solvent was then removed by distillation under reduced pressure, and the residue was dried, to give crude (2S, 4S)-2-carboxy-4-(4-methoxybenzylthio)-1-methylpyrrolidine.

The whole of this crude compound was suspended in 7.3 ml of acetonitrile and 318 mg of N,N'-carbonyldiimidazole were added to the suspension, and the resulting mixture was then stirred at 40° C. for 1 hour. At the end of this time, the mixture was allowed to cool to room temperature, and then a solution of 559 mg of dimethylamine in 3.7 ml of tetrahydrofuran was added to the mixture. The mixture was then allowed to stand at room temperature overnight. The solvent and an excess of dimethylamine were removed by distillation under reduced pressure. The residue was mixed with an aqueous solution of sodium chloride and extracted with ethyl acetate. The extract was dried over anhydrous magnesium sulfate and the solvent was distilled off under reduced pressure. The residue was purified according to the procedure described in Reference Example 4-(5), to give 382 mg of the title compound as an oil.

4-(12) (2S, 4S)-2-(N,N-Dimethylcarbamoyl)-4-(4-methoxy-benzyl-thio)-1,1-dimethylpyrrolidinium fluorosulfonate 139 μl of methyl fluorosulfonate were added, whilst ice-cooling, to a solution of 190 mg of (2S, 4S)-methylpyrrolidine [prepared as described in step (5) or (11) above] dissolved in 3.8 ml of methylene chloride, and the mixture was stirred at room temperature for 2 hours. At the end of this time, the solvent was distilled off under reduced pressure. The residue was repeatedly washed by decantation with hexane and dried under reduced pressure, to give 356 mg of the title compound as an oil.

Nuclear Magnetic Resonance Spectrum (D$_2$O, 60 MHz) δ ppm: 1.58–4.58 (12H, multiplet); 3.07 (6H, singlet); 3.84 (3H, singlet); 3.90 (2H, singlet); 6.90, 7.25 (4H, A J=9.0 Hz).

PREPARATION 5

(3S)-1,1-Dimethyl-3-(4-methoxybenzylthio)pyrrolidiniumfluorosulfonate

5-(1)

(3R)-1-t-Butoxycarbonyl-3-methanesulfonyloxypyrrolidine 16.91 ml of triethylamine and 9.36 ml of methanesulfonyl chloride were added, in that order, whilst ice-cooling, to a solution of 25 g of (3R)-1-t-butoxycarbonyl-3-hydroxypyrrolidine dissolved in 250 ml of dry tetrahydrofuran, and the mixture was stirred at 0° to 5° C. for 30 minutes and then at 15° C. for 30 minutes. At the end of this time, the mixture was poured into an aqueous solution of sodium chloride and extracted with ethyl acetate. The extract was washed with an aqueous solution of sodium chloride and dried over anhydrous magnesium sulfate. The solvent was then removed by distillation under reduced pressure, to give 3.10 g of the title compound as a colorless oil.

Nuclear Magnetic Resonance Spectrum (CDCl$_3$, 60 MHz) δ ppm: 1.48 (9H. singlet); 1.91–2.45 (2H, multiplet); 3.04 (3H, singlet); 3.26–3.82 (4H, multiplet); 6:1–6.44 (1H, multiplet).

5-(2)

(3S)-1-t-Butoxycarbonyl-3-(4-methoxybenzylthio)pyrrolidine 5.32 g of sodium hydride (as a 55% w/w dispersion in mineral oil) were added, whilst ice-cooling, to a solution of 16.86 ml of 4-methoxybenzyl mercaptan dissolved in 200 ml of dry dimethylformamide, and the mixture was then stirred at room temperature for 30 minutes. At the end of this time, a solution of 31.00 g of (3R)-1-t-butoxycarbonyl-3-methanesulfonyloxypyrrolidine [prepared as described in step (1) above] in 50 ml of dry dimethylformamide was added to the reaction mixture. The mixture was then stirred for 30 minutes whilst ice-cooling, after which it was allowed to stand overnight at room temperature. It was then poured into an aqueous solution of sodium chloride and extracted with ethyl acetate. The extract was washed with an aqueous solution of sodium chloride and dried over anhydrous magnesium sulfate. The solvent was distilled off under reduced pressure. The residue was purified by column chromatography through silica gel (eluted with a 5:1 by volume mixture of hexane and ethyl acetate), to afford 28.00 g of the title compound a pale-brown oil.

Nuclear Magnetic Resonance Spectrum (CDCl$_3$, 60 MHz) δ ppm: 1.46 (9H, singlet); 1.50–2.35 (2H, multiplet); 2.81–3.88 (5H, multiplet); 3.70 (2H, singlet); 3.79 (3H, singlet); 6.83, 7.27 (4H, A$_2$B$_2$, J=9.0Hz).

5-(3)

(3S)-3-(4-Methoxybenzylthio)pyrrolidinehydrochloride 106 ml of a 4N ethyl acetate solution of hydrogen chloride were added, whilst ice-cooling, to a solution of 27.50 g of (3R)-1-t-butoxycarbonyl-3-(4-methoxybenzylthio)pyrrolidine [prepared as described in step (2) above] dissolved in 100 ml of ethyl acetate, and the mixture was stirred at 0° to 5° C. for 30 minutes and then at 25° C. for 2 hours. At the end of this time, the mixture was diluted with 200 ml of diisopropyl ether, and the crystals which precipitated were collected by filtration, to give 20.84 g of the title compound as colorless crystals, melting at 125°–126° C.

Infrared Absorption Spectrum (KBr) δ$_{max}$ cm$^{-1}$: 1510, 1246, 1174.

Nuclear Magnetic Resonance Spectrum (D$_2$O, 60 MHz) δ ppm: 1.52-2.53 (2H, multiplet); 2.91–3.70 (5H, multiplet); 3.63 (2H, singlet); 3.67 (3H, singlet); 6.80, 7.16 (4H, A J=9.0 Hz).

5-(4)

(3S)-3-(4-Methoxybenzylthio)-1-methylpyrrolidine 750 mg of (3S)-3-(4-methoxybenzylthio)pyrrolidine [which had been prepared by neutralization of 900 mg of (3S)-3-(4-methoxybenzylthio)pyrrolidine hydrochloride, prepared as described in step (3) above, with sodium bicarbonate] were dissolved in 15 ml of dry acetonitrile, and 1.44 ml of a 35% by volume solution of formaldehyde in water was added to the solution. The reaction mixture was then stirred for 15 minutes, after which it was neutralized by the addition of acetic acid; it was then again stirred for a further 2.5 hours. At the end of this time, the reaction mixture was poured into 200 ml of ethyl acetate, and the mixture was washed with a 2N aqueous solution of potassium hydroxide and an aqueous solution of sodium chloride. The organic layer was dried over potassium carbonate and the solvent was distilled off under reduced pressure. The residue was purified by column chromatography through silica gel (eluted with a 3:1 by volume mixture of ethyl acetate and methanol), to afford 349 mg of the title compound as a colorless oil.

Nuclear Magnetic Resonance Spectrum (CDCl$_3$, 60 MHz) δ ppm: 1.40–3.49 (7H, multiplet); 2.33 (3H, singlet); 3.69 (2H, singlet); 3.78 (3H, singlet); 6.86, 7.25 (4H, A$_2$B$_2$, J=9.0 Hz).

5-(5)

(3S)-1,1-Dimethyl-3-(4-methoxybenzylthio)pyrrolidinium fluorosulfonate

118 μl of methyl fluorosulfonate were added, whilst ice-cooling, to a solution of 340 mg of (3S)-3-(4-methoxybenzylthio)-1-methylpyrrolidine [prepared as described in step (4) above] dissolved in 20 ml of dry methylene chloride. The mixture was then stirred at the same temperature for 30 minutes and then at room temperature for 3.5 hours. At the end of this time, the solvent was removed by distillation under reduced pressure, and the residue was repeatedly washed by decantation with diethyl ether and dried under reduced pressure to afford 500 mg of the title compound as a colorless powder.

Nuclear Magnetic Resonance Spectrum (D$_2$O, 270 MHz); δ ppm: 1.86–2.05 (1H, multiplet); 2.34–2.56 (1H, multiplet); 2.90 (3H, singlet); 3.01 (3H, singlet); 2.98–3.73 (5H, multiplet); 3.65 (3H, singlet); 3.67 (2H, singlet); 6.82, 7.17 (4H, A$_2$B$_2$, J=8.62Hz).

PREPARATION 6

1,1-Dimethyl-4-(4-methoxybenzylthio)piperidinium fluorosulfonate

6-(1) 4-Methanesulfonyloxy-1-methylpiperidine 13.3 ml of triethylamine and subsequently 7.4 ml of methanesulfonyl chloride were added, whilst ice-cooling, to a solution of 10 g of 4-hydroxy-1-methylpiperidine dissolved in 100 ml of dry tetrahydrofuran. The mixture was then stirred at 0° to 5° C. for 2 hours and then at room temperature for 1.5 hours, after which it was poured into an aqueous solution of sodium chloride and extracted with ethyl acetate. The extract was washed with an aqueous solution of sodium chloride and dried over anhydrous magnesium sulfate. The solvent was then distilled off under reduced pressure, to afford 12.74 g of the title compound as an oil.

Nuclear Magnetic Resonance Spectrum (CDCl$_3$, 60 MHz) δ ppm: 1.74-2.90 (8H, multiplet); 2.28 (3H, singlet); 3.00 (3H, singlet); 4.73 (1H, multiplet).

6-(2) 4-(4-Methoxybenzylthio)-1-methylpiperidine 10.9 ml of 4-methoxybenzyl mercaptan were dissolved in 55 ml of dry dimethylformamide, and 3.4 g of sodium hydride (as a 55% w/w suspension in mineral oil) were added to the solution, whilst ice-cooling. The mixture was then stirred at room temperature for 30 minutes. At the end of this time, a solution of 12.6 g of 4-methanesulfonyloxy-1-methylpiperidine in 63 ml of dry dimethylformamide was added to the mixture, which was then allowed to stand overnight at room temperature. The reaction mixture was then poured into an aqueous solution of sodium chloride and extracted with ethyl acetate. The extract was washed with an aqueous solution of sodium chloride and dried over anhydrous magnesium sulfate. The solvent was then removed by distillation under reduced pressure, and the residue was purified by column chromatography through silica gel (eluted with a 1:4 by volume mixture of ethyl acetate and methanol) to afford 9.01 g of the title compound as an oil.

Nuclear Magnetic Resonance Spectrum (CDCl$_3$, 60 MHz) δ ppm: 1.40-3.05 (9H, multiplet); 2.23 (3H, singlet); 3.69 (2H, singlet); 3.78 (3H, singlet); 6.82, 7.23 (4H, A$_2$B$_2$, J=9.0 Hz).

6-(3) 1,1-Dimethyl-4-(4-methoxybenzylthio)piperidinium fluorosulfonate 2.9 ml of methyl fluorosulfonate were added, whilst ice-cooling, to a solution of 8.95 g of 4-(4-methoxybenzylthio)-1-methylpiperidine dissolved in 300 ml of dry methylene chloride, and the mixture was stirred at the same temperature for 20 minutes and then at room temperature for 2.5 hours. At the end of this time, the solvent was removed by distillation under reduced pressure, and the residue was washed repeatedly by decantation with diethyl ether and dried under reduce pressure, to afford 12.76 g of the title compound as a colorless powder.

Nuclear Magnetic Resonance Spectrum (CDCl$_3$, 270 MHz) δ ppm: 1.75-1.93 (2H, multiplet); 2.02-2.15 (2H, multiplet); 2.70-2.84 (2H, multiplet); 3.05 (3H, singlet); 3.06 (3H, singlet); 3.24-3.97 (4H, multiplet); 3.74 (3H, singlet); 3.78 (2H, singlet); 6.88, 7.26 (4H, A$_2$B$_2$, J=8.79Hz).

PREPARATION 7

(2S, 4S)-2-(N,N-Dimethylcarbamoyl)-1-ethyl-1-methyl-4-(4-methoxybenzylthio)pyrrolidinium fluorosulfonate 7-(1) (2S, 4S)-1-Ethyl-4-(4-methoxybenzylthio)-2-methoxycarbonylpyrrolidinium fluorosulfonate 1.2 g of (2S, 4S)-1-ethyl-4-(4-methoxybenzylthio)-2-methoxycarbonylpyrrolidine [prepared as described 1n preparation 4-(9)] was dissolved in 12 ml of dry dimethylformamide, and 358 mg of sodium bicarbonate and 0.41 ml of ethyl iodide were added to the resulting solution, whilst ice-cooling. The mixture was then stirred at room temperature for 6 hours and then at 45° to 50° C. for 3 hours. It was then poured into a saturated aqueous solution of sodium bicarbonate and then extracted with ethyl acetate. The extract was washed with an aqueous solution of sodium chloride and dried over anhydrous magnesium sulfate. The solvent was then removed by distillation under reduced pressure, and the residue was purified by column chromatography through silica gel (eluted with a 1:4 by volume mixture of ethyl acetate and benzene) to afford 904 mg of the title compound as an oil.

Infrared Absorption Spectrum (liquid film) δ$_{max}$ cm$^{-1}$: 1740, 1615, 1590, 1515.

Nuclear Magnetic Resonance Spectrum (CDCl$_3$, 60 MHz) δ ppm: 1.03 (3H, triplet, J=7.0 Hz); 2.72-3.43 (8H, multiplet); 3.70 (5H, singlet); 3.78 (3H, singlet); 6.84, 7.25 (4H, A$_2$B$_2$, J=9.0Hz).

7-(2) (2S, 4S)-2-(N,N-Dimethylcarbamoyl)-1-ethyl-4-(4-methoxybenzylthio)pyrrolidine 883 mg of (2S, 4S)-1-ethyl-4-(4-methoxybenzylthio)-2-methoxycarbonylpyrrolidine were dissolved in 8.6 ml of methanol, and 4.3 ml of a 1N aqueous solution of sodium hydroxide were added to the resulting solution. The mixture was then stirred at room temperature for 2 hours, after which it was neutralized by adding 4.3 ml of 1N aqueous hydrochloric acid. The reaction mixture was then evaporated to dryness under reduced pressure, to give a crude product.

The resulting crude product was suspended in 18 ml of dry acetonitrile, and 694 mg of N,N'-carbodiimidazole were added to the suspension. The mixture was then stirred at 40° C. for 1 hour, after which a solution of 1.89 ml of dimethylamine in 10 ml of tetrahydrofuran was added to the mixture. The reaction mixture was then allowed to stand at room temperature overnight, after which it was concentrated by evaporation under reduced pressure. The residue was mixed with an aqueous solution of sodium chloride and extracted with ethyl acetate and the extract was washed with an aqueous solution of sodium chloride and then dried over anhydrous magnesium sulfate. The solvent was then removed by distillation under reduced pressure, and the residue was subjected to column chromatography using a Lobar column (Merck, LiChroprep Si60, size B). 795 mg of the title compound were obtained as an oil from the fractions eluted with a 10:1 by volume mixture of ethyl acetate and methanol.

Infrared Absorption Spectrum (liquid film) ν$_{max}$ cm$^{-1}$: 1640, 1610, 1585, 1515.

Nuclear Magnetic Resonance Spectrum (CDCl$_3$, 60 MHz) δ ppm: 1.01 (3H, triplet, J=7.0 Hz); 1.57-3.73 (8H, multiplet); 2.91 (3H, singlet); 3.16 (3H, singlet); 3.70 (2H, singlet); 3.78 (3H, singlet); 6.83, 7.27 (4H, A$_2$B$_2$, J=9.0Hz).

7-(3) (2S, 4S)-2-(N,N-Dimethylcarbamoyl)-1-ethyl-1-methyl-4-(4-methoxybenzylthio)pyrrolidinium fluorosulfonate 128 μl of methyl fluorosulfonate were added to a solution of 438 mg of (2S, 4S)-2-(N,N-dimethylcarbamoyl)-1-ethyl-4-(4-methoxybenzylthio)pyrrolidine dissolved in 10 ml of methylene chloride, and the mixture was stirred at room temperature for 2 hours. At the end of this time, the solvent was removed by distillation under reduced pressure, and the residue was washed repeatedly by decantation with diethyl ether and dried under reduced pressure to afford the title compound as an oil.

Nuclear Magnetic Resonance Spectrum (D$_2$O, 270 MHz) δ ppm: 1.12 (3H, triplet, J=7.15 Hz); 1.96–2.08 (1H, multiplet); 2.62–3.51 (6H, multiplet); 2.79 (3H, singlet); 2.93 (3H, singlet); 2.95 (3H, singlet); 3.65 (3H, singlet); 3.68 (2H, singlet); 4.55–4.60 (1H, multiplet).

PREPARATION 8

(2S, 4S)-1,1-Dimethyl-4-(4-methoxybenzylthio)-2-(4-morpholinocarbonyl)pyrrolidinium fluorosulfonate

8-(1) (2S, 4S)-4-(4-Methoxybenzylthio)-2-methoxycarbonyl-1-methylpyrrolidine 3.43 ml of 35% formalin were added to a solution of 2.25 g of (2S, 4S)-4-(4-methoxybenzylthio)-2-methoxycarbonylpyrrolidine dissolved in 42 ml of acetonitrile. Subsequently, 804 mg of sodium cyanoborohydride were divided into three portions and added to the mixture over a period of 5 minutes. The mixture was then stirred at room temperature for 30 minutes. At the end of this time, the mixture was cooled, 1.3 ml of acetic acid was added, and the reaction mixture was stirred at room temperature for 40 minutes. 40 ml of a 1N aqueous solution of sodium hydroxide and an aqueous solution of sodium chloride were then added to the mixture, after which it was extracted with ethyl acetate. The extract was washed with an aqueous solution of sodium chloride and dried over anhydrous magnesium sulfate. The solvent was then removed by distillation under reduced pressure, and the residue was purified by a similar procedure to that described in preparation 4-(10), to afford 1.31 g of the title compound as an oil. The infra-red spectrum, nuclear magnetic resonance spectrum and thin layer chromatograph of this compound were identical to those of the compound prepared as described in preparation 4-(10).

8-(2) (2S, 4S)-4-(4-Methoxybenzylthio)-1-methyl-2-(4-morpholinocarbonyl)pyrrolidine 5.32 ml of a 1N aqueous solution of sodium hydroxide were added to a solution of 1.31 g of (2S, 4S)-4-(4-methoxybenzylthio)-2-methoxycarbonyl-1-methylpyrrolidine dissolved in 11 ml of methanol, and the mixture was stirred at room temperature for 2 hours. At the end of this time, it was neutralized with 5.32 ml of 1N aqueous hydrochloric acid, and the reaction mixture was freed from the solvent by evaporation under reduced pressure, and the residue was dried and concentrated by evaporation under reduced pressure, to afford 1.5 g of crude (2S, 4S)-2-carboxy-4-(4-methoxybenzylthio)-1-methylpyrrolidine.

500 mg of this crude (2S, 4S)-2-carboxy-4-(4-methoxybenzylthio)-1-methylpyrrolidine were suspended in 10 ml of acetonitrile, and 278 mg of N,N'-carbonyldiimidazole were added to the suspension, and the mixture was stirred at 40° C. for 1 hour. The mixture was then allowed to cool to room temperature, after which 187 μl of morpholine were added, and the reaction mixture was stirred at room temperature for 2 hours and then allowed to stand overnight. The solvent and excess morpholine were then removed by distillation under reduced pressure, and the residue was mixed with an aqueous solution of sodium chloride and extracted with ethyl acetate. The extract was dried over anhydrous magnesium sulfate and the solvent was distilled off under reduced pressure. The residue was subjected to column chromatography using a Lobar column (Merck, LiChroprep Si60, size B) and 418 mg of the title compound were obtained as an oil from the fractions eluted with a 3:1:1 by volume mixture of cyclohexane, ethyl acetate and methanol.

Infrared Absorption Spectrum (liquid film) $\nu_{max}$ cm$^{-1}$: 1639, 1610, 1511.

Nuclear Magnetic Resonance Spectrum (CDCl$_3$, 60 MHz) δ ppm: 1.50–3.33 (6H, multiplet); 2.31 (3H, singlet); 3.64 (8H, broad singlet); 3.70 (2H, singlet); 3.78 (3H, singlet); 6.82, 7.21 (4H, A J=9.0 Hz).

8-(3) (2S, 4S)-1,1-Dimethyl-4-(4-methoxybenzylthio)-2-(4-morpholinocarbonyl)pyrrolidine fluorosulfonate 106 μl of methyl fluorosulfonate were added to a solution of 392 mg. of (2S, 4S)-4-(4-methoxybenzylthio)-1-methyl-2-(4-morpholinocarbonyl)pyrrolidine dissolved in 8 ml of methylene chloride, and the mixture was stirred at room temperature for 2 hours. At the end of this time, the solvent was removed by distillation under reduced pressure, and the residue was washed repeatedly by decantation with diethyl ether and dried under reduced pressure to afford 446 mg of the title compound as an oil.

Nuclear Magnetic Resonance Spectrum (D$_2$O, 270 MHz) δ ppm: 1.80–2.03 (1H, multiplet); 2.67–3.90 (12H, multiplet); 2.98 (3H, singlet); 3.07 (3H, singlet); 3.65 (3H, singlet); 3.68 (2H, singlet); 4.61 (1H, doublet of doublets, J=8.06, 6.23Hz), 6.82, 7.17 (4H, A$_2$B$_2$, J=8.61 Hz).

PREPARATION 9

(2S, 4S)-1,1-Dimethyl-4-(4-methoxybenzylthio)-2-(1-pyrrolidinocarbonyl)pyrrolidinium fluorosulfonate

9-(1) (2S, 4S)-4-(4-Methoxybenzylthio)-1-methyl-2-(1-pyrrolidinocarbonyl)pyrrolidine The procedure described in preparation 8-(2) was repeated, but using 500 mg of crude (2S, 4S)-2-carboxy-4-(4-methoxybenzylthio)-1-methylpyrrolidine [prepared as described in preparation 8-(2)]. 278 mg of N,N'-carbonyldiimidazole and 178 μl of pyrrolidine instead of morpholine, to afford 440 mg of the title compound.

Infrared Absorption Spectrum (KBr) $\delta_{max}$ cm$^{-1}$: 1640, 1611, 1511, 1444.

Nuclear Magnetic Resonance Spectrum (CDCl$_3$, 60 MHz) δ ppm: 1.58–2.78 (6H, multiplet); 2.30 (3H, singlet); 2.90–3.80 (8H, multiplet); 3.70 (2H, singlet); 3.78 (3H, singlet); 6.84, 7.24 (4H, A$_2$B$_2$, J=9.0 Hz).

9-(2) (2S, 4S)-1,1,-Dimethyl-4-(4-methoxybenzylthio)-2-(1-pyrrolidinocarbonyl)pyrrolidinium fluorosulfonate The procedure described in preparation 8-(3) was repeated, but using 418 mg of (2S, 4S)-4-(4-methoxybenzylthio)-1-methyl-2-(1-pyrrolidinocarbonyl)pyrrolidine, 118 μl of methyl fluorosulfonate, to afford 472 mg of the title compound as an oil.

Nuclear Magnetic Resonance Spectrum (D$_2$O, 270 MHz) δ ppm: 1.68–1.85 (4H, multiplet); 1.94–2.10 (1H, multiplet); 2.69–3.85 (7H, multiplet); 2.99 (3H, singlet); 3.03 (3H, singlet); 3.65 (3H, singlet); 3.67 (2H, singlet); 4.41 (1H, doublet of doublets, J = 8.06, 6.60 Hz); 6.81, 7.17 (4H, A$_2$B$_2$, J = 8.62 Hz).

PREPARATION 10

(2S, 4S)-2-Carbamoyl-4-(4-methoxybenzylthio)-1-ethyl-1-methylpyrrolidinium fluorosulfonate

10-(1) (2S, 4S)-2-Carbamoyl-1-ethyl-4-(4-methoxybenzylthio)pyrrolidine 0.362 ml of ethyl iodide and 315 mg of sodium bicarbonate to a solution of 1000 mg of (2S, 4S)-2-carbamoyl-4-(4-methoxybenzylthio)pyrrolidine dissolved in 10 ml of dry dimethylformamide were added, whilst ice-cooling, and the mixture was stirred at room temperature for 5.5 hours. At the end of this time, the reaction mixture was poured into a saturated aqueous solution of sodium bicarbonate and extracted with ethyl acetate. The extract was washed with an aqueous solution of sodium chloride and dried over anhydrous magnesium sulfate, and then the solvent was removed by distillation under reduced pressure. The residue was subjected to column chromatography through silica gel (Katayama Chemicals Co., Silica Gel 60K070) and 560 mg of the title compound were obtained as crystals, melting at 124°–125° C., from the fractions eluted with ethyl acetate.

Infrared Absorption Spectrum (KBr) $\delta_{max}$ cm$^{-1}$: 1632, 1509.

Nuclear Magnetic Resonance Spectrum (CDCl$_3$+D$_2$O, 270 MHz) δ ppm: 1.08 (3H, triplet, J = 7.33 Hz); 1.86–1.96 (1H, multiplet); 2.38–2.76 (4H, multiplet); 2.99–3.18 (3H, multiplet); 3.70 (2H, singlet); 3.80 (3H, singlet); 6.84, 7.21 (4H, A$_2$B$_2$, J = 8.79 Hz).

10-(2) (2S, 4S)-2-Carbamoyl-4-(4-methoxybenzylthio)-1-ethyl-1-methylpyrrolidinium fluorosulfonate 0.43 ml of methyl fluorosulfonate was added, whilst ice-cooling, to a solution of 1.44 g of (2S, 4S)-2-carbamoyl-4-(4-methoxybenzylthio)-1-ethylpyrrolidine dissolved in 30 ml of dry methylene chloride and the mixture was stirred at room temperature for 2 hours. At the end of this time, the solvent was removed by distillation under reduced pressure, and the residue was washed repeatedly by decantation with diethyl ether and dried under reduced pressure to afford 2.0 g of the title compound as an oil.

Infrared Absorption Spectrum (liquid film) $\delta_{max}$ cm$^{-1}$: 1698, 1610, 1512.

Nuclear Magnetic Resonance Spectrum (D$_2$O, 270 MHz) δ ppm: 1.12 (3H, triplet, J = 7.33 Hz); 2.06–2.18 (1H, multiplet); 2.63–3.83 (6H, multiplet); 2.92 (3H, singlet); 3.64 (3H, singlet); 3.65 (2H, singlet); 4.02–4.09 (1H, multiplet); 6.82, 7.16 (4H, A$_2$B$_2$, J = 8.42 Hz).

PREPARATION 11

(2S, 4S)-2-Ethylcarbamoyl-1-ethyl-1-methyl-4-(4-methoxybenzylthio)pyrrolidinium fluorosulfonate

(1) (2S, 4S)-1-t-Butoxycarbonyl-2-ethylcarbamoyl-4-hydroxypyrrolidine 15.25 ml of triethylamine and subsequently a solution of 10.48 ml of ethyl chloroformate in 50 ml of dry tetrahydrofuran were added at −25° C. to a solution of 23.13 g of (2S, 4S)-1-t-butoxycarbonyl-4-hydroxy-2-pyrrolidinecarboxylic acid dissolved in 350 ml of dry tetrahydrofuran, and the mixture was stirred at the same temperature for 30 minutes. At the end of this time, a 70% by volume aqueous ethylamine solution was added at −22° C., the reaction temperature was allowed to rise gradually and the reaction finished when the temperature reached 10° C. The reaction mixture was then mixed with a small amount of an aqueous solution of sodium chloride, after which it was extracted thrice with ethyl acetate. The combined extracts were washed with an aqueous solution of sodium chloride and dried over anhydrous magnesium sulfate. The solvent was then removed by distillation under reduced pressure, to afford 23.60 g of the title compound as a colorless oil.

Nuclear Magnetic Resonance Spectrum (CDCl$_3$, 60 MHz) δ ppm: 1.10 (3H, triplet, J = 7.5 Hz); 1.44 (9H, singlet); 1.80–4.65 (10H, multiplet); 6.64 (1H, broad singlet).

11-(2) (2S, 4S)-1-t-Butoxycarbonyl-2-ethylcarbamoyl-4-methanesulfonyloxypyrrolidine 13.81 ml of triethylamine and subsequently 7.65 ml of methanesulfonyl chloride were added, whilst ice-cooling, to a solution of 23.20 g of (2S, 4S)-1-t-butoxycarbonyl-2-ethylcarbamoyl-4-hydroxypyrrolidine dissolved in 250 ml of dry tetrahydrofuran, and then the mixture was stirred at 0° to 5° C. for 30 minutes. The reaction mixture was then poured into an aqueous solution of sodium chloride and extracted with ethyl acetate. The extract was washed with an aqueous solution of sodium chloride and dried over anhydrous magnesium sulfate. The solvent was then removed by distillation under reduced pressure, to afford 26.54 g of the title compound as colorless crystals, melting at 138°–140° C.

Infrared Absorption Spectrum (KBr) $\delta_{max}$ cm$^{-1}$: 1675, 1548, 1348.

Nuclear Magnetic Resonance Spectrum (CDCl$_3$, 60 MHz) δ ppm: 1.12 (3H, triplet, J = 7.5 Hz); 1.48 (9H, singlet); 2.05–4.59 (7H, multiplet); 3.03 (3H, singlet); 5.07–5.43 (1H, multiplet); 6.58 (1H, broad singlet).

11-(3) (2S, 4S)-1-t-Butoxycarbonyl-2-ethylcarbamoyl-4-(4-methoxybenzylthio)pyrrolidine 3.57 g of sodium hydride (as a 55% w/w suspension in mineral oil) was added, whilst ice-cooling, to a solution of 11.31 ml of 4-methoxybenzyl mercaptan dissolved in 150 ml of dry dimethylformamide and the mixture was stirred at 0° to 5° C. for 30 minutes. A solution of 26.00 g of (2S, 4S)-1-t-butoxycarbonyl-2-ethylcarbamoyl-4-methanesulfonyloxypyrrolidine in 100 ml of dry dimethylformamide was then added to the resulting mixture, and the whole was stirred at room temperature for 2 hours. At the end of this time, the reaction mixture was poured into an aqueous solution of sodium chloride and extracted with ethyl acetate. The extract was washed with an aqueous solution of sodium chloride and dried over anhydrous magnesium sulfate. At the end of this time, the solvent was removed by distillation under reduced pressure, and the residue was purified by column chromatography through silica gel using a 1:1 by volume mixture of hexane and ethyl acetate as an eluent, to afford 17.00 g of the title compound as colorless crystals, melting at 92°–94° C.

Infrared Absorption Spectrum (KBr) $\delta_{max}$ cm$^{-1}$: 1700, 1655, 1406.

Nuclear Magnetic Resonance Spectrum (CDCl$_3$, 60 MHz) $\delta$ ppm: 1.10 (3H, triplet, J=7.5 Hz); 1.43 (9H, singlet); 1.85–3.96 (7H, multiplet); 3.69 (2H, singlet); 3.78 (3H, singlet); 4.18 (1H, triplet, J=7.5 Hz); 6.35 (1H, broad singlet); 6.86, 7.24 (4H, A$_2$B$_2$, J=9.0 Hz).

11-(4) (2S, 4S)-2-Ethylcarbamoyl-4-(4-methoxybenzylthio)pyrrolidine 41.19 ml of a 4N ethyl acetate solution of hydrogen chloride were added to a solution of 13.00 g of (2S, 4S)-1-t-butoxycarbonyl-2-ethylcarbamoyl-4-(4-methoxybenzylthio)pyrrolidine dissolved in 100 ml of ethyl acetate, and the mixture was stirred at room temperature for 3 hours. At the end of this time, the reaction mixture was poured into a saturated aqueous solution of sodium bicarbonate and extracted with ethyl acetate. The aqueous layer was saturated with ammonium chloride and extracted with tetrahydrofuran. The combined extracts were washed with an aqueous solution of sodium chloride and dried over anhydrous magnesium sulfate, and then the solvent was removed by distillation under reduced pressure. The residue was subjected to column chromatography through silica gel (eluted with a 87:13 by volume mixture of ethyl acetate and methanol) to afford 8.00 g of the title compound as pale brown crystals, melting at 67–68° C.

Infrared Absorption Spectrum (KBr) $\delta_{max}$ cm$^{-1}$: 1649, 1512, 1240.

Nuclear Magnetic Resonance Spectrum (CDCl$_3$, 60 MHz) $\delta$ ppm: 1.10 (3H, triplet, J=7.5 Hz); 1.50–2.20 (1H, multiplet); 2.16 (1H, singlet); 2.23–3.96 (7H, multiplet); 3.69 (2H, singlet); 3.78 (3H, singlet); 6.86, 7.25 (4H, A$_2$B$_2$, J=9.0 Hz); 7.53 (1H, broad singlet).

11-(5) (2S, 4S)-2-Ethylcarbamoyl-1-ethyl-4-(4-methoxybenzylthio)pyrrolidine

301 μl of ethyl iodide and 314 mg of sodium bicarbonate were added, whilst ice-cooling, to a solution of 1.00 g of (2S, 4S)-2-ethylcarbamoyl-4-(4-methoxybenzylthio)pyrrolidine dissolved in 8 ml of dry dimethylformamide, and the mixture was stirred at room temperature for 5 hours. At the end of this time, the reaction mixture was poured into an aqueous solution of sodium chloride and extracted with ethyl acetate. The extract was washed with an aqueous solution of sodium chloride and dried over anhydrous magnesium sulfate, after which the solvent was removed by distillation under reduced pressure. The residue was subjected to column chromatography through silica gel (eluted with ethyl acetate) to afford 982 mg of the title compound as colorless crystals, melting at 60°–61° C.

Infrared Absorption Spectrum (KBr) $\delta_{max}$ cm$^{-1}$: 1651, 1512, 1252.

Nuclear Magnetic Resonance Spectrum (CDCl$_3$, 60 MHz) $\delta$ ppm: 1.06 (3H, triplet, J=7.5 Hz); 1.14 (3H, triplet, J=7.5 Hz); 1.56–3.90 (10H, multiplet); 3.69 (2H, singlet); 3.80 (3H, singlet); 6.82, 7.20 (4H, A$_2$B$_2$, J=9.0 Hz); 7.30 (1H, broad singlet).

11-(6) (2S, 4S)-2-Ethylcarbamoyl-1-ethyl-1-methyl-4-(4-methoxybenzylthio)pyrrolidinium fluorosulfonate 233 μl of methyl fluorosulfonate were added, whilst ice-cooling, to a solution of 910 mg of (2S, 4S)-2-ethyl-carbamoyl-1-ethyl-4-(4-methoxybenzylthio)pyrrolidine dissolved in 35 ml of dry methylene chloride, and the mixture was stirred at room temperature for 3.5 hours. At the end of this time, the solvent was removed by distillation under reduced pressure, and the residue was washed by decantation with diethyl ether and dried under reduced pressure, to afford 1.20 g of the title compound as a pale brown oil.

Infrared Absorption Spectrum (liquid film) $\delta_{max}$ cm$^{-1}$: 1680, 1513, 1250.

Nuclear Magnetic Resonance Spectrum (D$_2$O, 270 MHz) $\delta$ ppm: 0.93 (3H, triplet, J=7.33 Hz); 1.12 (3H, triplet, J=7.33 Hz); 1.95–2.26 (1H, multiplet); 2.56–4.50 (9H, multiplet); 2.88 (3H, singlet); 3.65 (3H, singlet); 3.69 (2H, singlet); 6.83, 7.18 (4H, A$_2$B$_2$, J=8.80 Hz).

PREPARATION 12

(2S, 4S)-1-Ethyl-1-methyl-2-methylcarbamoyl-4-(4-methoxybenzylthio)pyrrolidinium fluorosulfonate 12-(1) (2S, 4S)-1-Ethyl-4-(4-methoxybenzylthio)-2-methylcarbamoylpyrrolidine 0.71 ml of ethyl iodide and 742 mg of sodium bicarbonate were added to a solution of 2.25 g of (2S, 4S)-4-(4-methoxybenzylthio)-2-methylcarbamoylpyrrolidine dissolved in 20 ml of dry dimethylformamide, and the mixture was stirred at 0° to 5° C. for 1 hour and then at room temperature for 5 hours. At the end of this time, the reaction mixture was poured into an aqueous solution of sodium chloride and extracted with ethyl acetate. The extract was washed with an aqueous solution of sodium chloride and dried over anhydrous magnesium sulfate, after which the solvent was removed by distillation under reduced pressure. The residue was purified by column chromatography (eluted with ethyl acetate), to afford 1.87 g of the title compound as colorless crystals, melting at 68°–70° C.

Infrared Absorption Spectrum (KBr) $\delta_{max}$ cm$^{-1}$: 1657, 1511, 1252.

Nuclear Magnetic Resonance Spectrum (CDCl$_3$, 60 MHz) $\delta$ ppm: 1.02 (3H, triplet, J=7.0 Hz); 1.58–3.91 (8H, multiplet); 2.80 (3H, doublet, J=5.0 Hz); 3.67 (2H, singlet); 3.78 (3H, singlet); 6.85, 7.21 (4H, A$_2$B$_2$, J=9.0 Hz); 7.10–7.60 (1H, broad singlet).

12-(2) (2S, 4S)-1-Ethyl-1-methyl-2-methylcarbamoyl-4-(4-methoxybenzylthio)pyrrolidinium fluorosulfonate 187 μl of methyl fluorosulfonate were added, whilst ice-cooling, to a solution of 700 mg of (2S, 4S)-1-ethyl-4-(4-methoxybenzylthio)-2-methylcarbamoyl-pyrrolidine dissolved in 30 ml of dry methylene chloride, and the mixture was stirred at room temperature for 4 hours. At the end of this time, the solvent was removed by distillation under reduced pressure, and the residue was washed repeatedly by decantation with diethyl ether and dried under reduced pressure to afford 950 mg of the title compound as a colorless oil.

Infrared Absorption Spectrum (liquid film) $\delta_{max}$ cm$^{-1}$: 1683, 1565, 1280.

Nuclear Magnetic Resonance Spectrum (D$_2$O, 270 MHz) $\delta$ ppm: 1.12 (3H, triplet, J=7.33 Hz); 2.02–2.20 (1H, multiplet); 2.58–4.50 (7H, multiplet); 2.60 (3H, singlet); 2.87 (3H, singlet); 3.65 (3H, singlet); 3.68 (2H, singlet); 6.82, 7.17 (4H, A$_2$B$_2$, J=8.80 Hz).

PREPARATION 13

(2S,4S)-1,1-Dimethyl-2-ethylcarbamoyl-4-(4-methoxy-benzylthio)pyrrolidinium fluorosulfonate

13-(1) (2S,4S)-2-Ethylcarbamoyl-4-(4-methoxybenzyl-thio)-1-methylpyrrolidine 3.43 ml of 35% formalin and 804 mg of sodium cyanoborohydride were added to a solution of 2.36 g of (2S,4S)-2-ethylcarbamoyl-4-(4-methoxybenzylthio)-pyrrolidine dissolved in 42 ml of acetonitrile, and the mixture was stirred at room temperature for 40 minutes. At the end of this time, a 1N aqueous solution of sodium hydroxide was added, and the reaction mixture was poured into an aqueous solution of sodium chloride and extracted with ethyl acetate. The extract was washed with an aqueous solution of sodium chloride and dried over anhydrous magnesium sulfate, and the solvent was removed by distillation under reduced pressure. The residue was purified by column chromatography through silica gel (eluted with ethyl acetate) to afford 1.93 g of the title compound as colorless crystals. Infrared Absorption Spectrum (KBr) $\delta_{max}$ cm$^{-1}$: 1655, 1513, 1252.

Nuclear Magnetic Resonance Spectrum (CDCl$_3$, 60 MHz) $\delta$ ppm: 1.12 (3H, triplet, J=7.5 Hz); 1.50–2.20 (1H, multiplet); 2.31 (3H, singlet); 2.36–3.88 (7H, multiplet); 3.67 (2H, singlet); 3.78 (3H, singlet); 6.83, 7.21 (4H, A$_2$B$_2$, J=9.0 Hz); 7.20 (1H, broad singlet).

13-(2) (2S,4S)-1,1,-Dimethyl-2-ethylcarbamoyl-4-(4-methoxybenzylthio)pyrrolidinium fluorosulfonate 264 μl of methyl fluorosulfonate were added, whilst ice-cooling, to a solution of 987 mg of (2S, 4S)-2-ethylcarbamoyl-4-(4-methoxybenzylthio)-1-methyl-pyrrolidine dissolved in 40 ml of dry methylene chloride, and the mixture was stirred at room temperature for 2 hours. At the end of this time, the solvent was removed by distillation under reduced pressure, and the residue was washed repeatedly by decantation with diethyl ether and dried under reduced pressure to afford 1.332 g of the title compound as a colorless oil.

Infrared Absorption Spectrum (CHCl$_3$) $\delta_{max}$ cm$^{-1}$: 1680, 1510, 1240.

Nuclear Magnetic Resonance Spectrum (D$_2$O, 270 MHz) $\delta$ ppm: 0.94 (3H, triplet, J=7.33 Hz); 1.95–2.20 (1H, multiplet); 2.60–2.98 (1H, multiplet); 2.96 (3H, singlet); 3.00 (3H, singlet); 3.02–3.70 (5H, multiplet); 3.64 (3H, singlet); 3.67 (2H, singlet); 3.97 (1H, triplet, J=7.88 Hz); 6.81, 7.01 (4H, A$_2$B$_2$, J=8.80 Hz).

PREPARATION 14

(2S)-1,1-Dimethyl-4-(4-methoxybenzylthiomethyl)pyrrolidinium fluorosulfonate

14-(1) (2S)-1-t-Butoxycarbonyl-2-(4-methoxybenzylthiomethyl)pyrrolidine

The procedure described in preparation 5-(2) was repeated, but using 12.16 g of (2S)-1-t-butoxycarbonyl-2-methanesulfonyloxymethylpyrroldine [prepared by the methanesulfonylation of (2S)-1-t-butoxycarbonyl-2-hydroxymethylpyrrolidine], 7.3 ml of 4-methoxybenzyl mercaptan and 2.3 g of sodium hydride (as a 55% w/w suspension in mineral oil) in 100 ml of dry dimethylformamide, to afford 13.93 g of the title compound as an oil.

Infrared Absorption Spectrum (liquid film) $\delta_{max}$ cm$^{-1}$: 1690, 1615, 1590, 1518.

Nuclear Magnetic Resonance Spectrum (CDCl$_3$, 60 MHz) $\delta$ ppm: 1.20–4.15 (9H, multiplet); 1.45 (9H, singlet); 3.70 (2H, singlet); 3.78 (3H, singlet); 6.82, 7.25 (4H, A$_2$B$_2$, J=9.0 Hz).

14-(2) (2S)-2-(4-Methoxybenzylthiomethyl)pyrrolidine

The procedure described in preparation 5-(3) was repeated, but using 5 g of (2S)-1-t-butoxycarbonyl 2 (4-methoxybenzylthiomethyl)pyrrolidine, to afford 2.51 g of the title compound as colorless crystals, melting at 124°–126.5° C.

Infrared Absorption Spectrum (Nujol - trade mark) $\delta_{max}$ cm$^{-1}$: 1615, 1585, 1520.

Nuclear Magnetic Resonance Spectrum (CDCl$_3$, 60 MHz) 1.45–2.20 (4H, multiplet); 2.25–3.96 (6H, multiplet); 3.76 (5H, singlet); 6.85 & 7.32 (4H, A$_2$B$_2$, J=9.0 Hz).

14-(3) (2S)-2-(4-Methoxybenzylthiomethyl)-1-methylpyrrolidine

The procedure described in preparation 5-(4) was repeated, but using 2 g of (2S)-2-(4-methoxybenzylthiomethyl)pyrrolidine, 35% formalin and 848 mg of sodium cyanoborohydride in the presence of 44 ml of acetonitrile, to afford 883 mg of the title compound as an oil.

Infrared Absorption Spectrum (liquid film) $\nu_{max}$ cm$^{-1}$: 1610, 1585, 1510.

Nuclear Magnetic Resonance Spectrum (CDCl$_3$, 60 MHz) 1.40–3.22 (9H, multiplet); 2.26 (3H, singlet); 3.68 (2H, singlet); 3.78 (3H, singlet); 6.83, 7.25 (4H, A$_2$, B$_2$, J=9.0 Hz).

14-(4) (2S)-1,1-Dimethyl-2-(4-methoxybenzylthiomethyl)pyrrolidinium fluorosulfonate The procedure described in preparation 5-(5) was repeated, but using 740 mg of (2S)-2-(4-methoxybenzylthiomethyl)-1-methylpyrrolidine and 243 μl of methyl fluorosulfonate in the presence of 22 ml of methylene chloride, to afford 1.0 g of the title compound as crystals, melting at 150°–153° C.

Absorption Spectrum (Nujol) $\delta_{max}$ cm$^{-1}$: 1610, 1585, 1518.

Nuclear Magnetic Resonance Spectrum (D$_2$O, 270 MHz) $\delta$ ppm: 1.60–2.02 (3H, multiplet); 2.26–3.51 (6H, multiplet); 2.64 (3H, singlet); 2.85 (3H, singlet); 3.64 (5H, singlet); 6.82, 7.19 (4H, A$_2$B$_2$, J=8.79 Hz).

PREPARATION 15

(2R)-1,1-Dimethyl-4-(4-methoxybenzylthiomethyl)pyrrolidinium fluorosulfonate (1) The procedure described in preparation 14-(1), (2), (3) and (4) was repeated, but using (2S)-1-t-butoxycarbonyl-2-hydroxymethylpyrrolidine as the starting material, to afford the title compound as an oil.

Infrared Absorption Spectrum (liquid film) $\nu_{max}$ cm$^{-1}$: 1610, 1585, 1512, Nuclear Magnetic Resonance Spectrum (D$_2$O, 270 MHz) $\delta$ ppm: 1.64–2.00 (3H, multiplet); 2.25–3.48 (6H, multiplet); 2.64 (3H, singlet); 2.85 (3H, singlet); 3.64 (5H, singlet); 6.82, 7.18 (4H, A$_2$B$_2$, J=8.79 Hz).

PREPARATION 16

4S)-2-Carbamoyl-1-(2-hydroxyethyl)-4-(4-methoxybenzylthio)-1-methylpyrrolidinium fluorosulfonate

16-(1) (2S, 4S)-2-Carbamoyl-1-(2-hydroxyethyl)-4-(4-methoxybenzylthio)pyrrolidine 0.175 ml of 2-iodoethanol and 0.16 g of sodium bicarbonate were added, whilst ice-cooling, to a solution of 0.5 g of (2S, 4S)-2-carbamoyl-4-(4-methoxybenzylthio)-pyrrolidine [prepared as described in preparation 1-(5)] dissolved in 5 ml of dry dimethylformamide, and the mixture was stirred at the same temperature for 1 hour, at room temperature for 2.5 hours, and at 40° C. for 19 hours. The reaction mixture was then poured into a saturated aqueous solution of sodium bicarbonate and extracted with ethyl acetate. The extract was washed with an aqueous solution of sodium chloride and dried over anhydrous magnesium sulfate. The solvent was then removed by distillation under reduced pressure, and the residue was subjected to column chromatography through silica gel (Wako Pure Chemicals, Ltd.; Wako gel C-100). 0.465 g of the title compound was obtained as crystals from the fractions eluted with a 95:5 by volume mixture of ethyl acetate and methanol.

Infrared Absorption Spectrum (KBr) $\delta_{max}$ cm$^{-1}$: 1625, 1510, 1243.

Nuclear Magnetic Resonance Spectrum (CDCl$_3$, 270 MHz) $\delta$ ppm: 1.69 (1H, broad singlet); 1.92–1.99 (1H, multiplet); 2.55–2.72 (3H, multiplet); 2.82–2.92 (1H, multiplet); 3.12–3.18 (3H, multiplet); 3.67 (2H, triplet, J=4.03 Hz); 3.71 (2H, singlet); 3.80 (3H, singlet); 5.42 (1H, broad singlet); 6.85, 7.21 (4H, A$_2$B$_2$, J=8.8 Hz); 7.35 (1H, broad singlet).

16-(2) (2S, 4S)-2-Carbamoyl-1-(2-hydroxyethyl)-4-(4-methoxybenzylthio)-1-methylpyrrolidinium fluorosulfonate 0.108 ml of methyl fluorosulfonate was added dropwise at room temperature to a solution of 0.38 g of (2S, 4S)-2-carbamoyl-1-(2-hydroxyethyl)-4-(4-methoxybenzylthio)pyrrolidine dissolved in 7.5 ml of dry methylene chloride, and the mixture was stirred at the same temperature for 2 hours. At the end of this time, the solvent was removed by distillation under reduced pressure, and the residue was washed by decantation with diethyl ether and dried under reduced pressure, to afford 0.396 g of the title compound as an oil.

PREPARATION 17

3-(4-Methoxybenzylthio)-1-methylquinuclidinium fluorosulfonate

17-(1) 3-(4-Methoxybenzylthio)quinuclidine

The procedure described in preparation 6-(2) was repeated, but using 3.7 g of 3-methanesulfonyloxyquinuclidine (prepared by the methanesulfonylation of 3-quinuclidinol), 3.0 ml of 4-methoxybenzyl mercaptan and 0.942 g of sodium hydride (as a 55% w/w suspension in mineral oil), to afford 1.74 g of the title compound as an oil.

Infrared Absorption Spectrum (liquid film) 84 $_{max}$ cm$^{-1}$: 1620, 1590, 1510, 1247.

Nuclear Magnetic Resonance Spectrum (CDCl$_3$, 60 MHz) $\delta$ ppm: 1.02–2.31 (5H, multiplet); 2.33–3.41 (7J, multiplet); 3.67 (2H, singlet); 3.82 (3H, singlet); 6.86, 7.26 (4H, A$_2$B$_2$, J=9.0 Hz).

17-(2) 3-(4-Methoxybenzylthio)-1-methylquinuclidinium fluorosulfonate

The procedure described in preparation 6-(3) was repeated, but using 756 mg of 3-(4-methoxybenzylthio)quinuclidine and 271 μl of methyl fluorosulfonate in the presence of 5 ml of methylene chloride, to afford 1.078 g of the title compound as an oil.

Infrared Absorption Spectrum (liquid film) $\delta_{max}$ cm$^{-1}$: 1609, 1590, 1512, 1490, 1467.

Nuclear Magnetic Resonance Spectrum (D$_2$O, 270 MHz) $\delta$ ppm: 1.63–2.16 (5H, multiplet); 2.70 (3H, singlet); 2.76–3.77 (7H, multiplet); 3.63 (5H, singlet); 6.80, 7.15 (4H, A$_2$B$_2$, J=8.61 Hz).

PREPARATION 18

(6S, 8S)-1,4-Dimethyl-8-(4-methoxybenzylthio)-5-oxo-4-aza-1-azoniabicyclo[4.3.0]nonane fluorosulfonate

18-(1) (2S, 4S)-1-(2-hydroxyethyl)-4-(4-methoxybenzylthio)-2-methylcarbamoylpyrrolidine 934 μl of 2-iodoethanol and 1.01 g of sodium bicarbonate were added, whilst ice-cooling, to a solution of 2.80 g of (2S, 4S)-4-(4-methoxybenzylthio)-2-methylcarbamoylpyrrolidine dissolved in 18 ml of dry dimethylformamide, and the mixture was stirred at 40° C. for 24 hours. At the end of this time, the reaction mixture was poured into an aqueous solution of sodium chloride and extracted with ethyl acetate. The extract was washed with an aqueous solution of sodium chloride and dried over anhydrous magnesium sulfate. The solvent was then removed by distillation under reduced pressure, and the residue was purified by column chromatography through silica gel (eluted with a 15:1 by volume mixture of ethyl acetate and methanol), to afford 2.22 g of the title compound as colorless crystals, melting at 88°–89.5° C.

Infrared Absorption Spectrum (KBr) $\delta_{max}$ cm$^{-1}$: 1637, 1510, 1240.

Nuclear Magnetic Resonance Spectrum (CDCl$_3$, 270 MHz) $\delta$ ppm: 1.66–2.05 (2H, multiplet); 2.50–2.91 (4H, multiplet); 2.82 (3H, doublet, J=4.77 Hz); 3.07–3.21 (3H, multiplet); 3.56–3.75 (2H, multiplet); 3.69 (2H, singlet); 3.80 (3H, singlet); 6.84, 7.20 (4H, A$_2$B$_2$, J=8.79 Hz); 7.42 (1H, broad singlet).

18-(2) (2S, 4S)-1-(2-Methanesulfonyloxyethyl)-4-(4-methoxybenzylthio)-2-methylcarbamoylpyrrolidine 1.06 ml of triethylamine and subsequently 584 μl of methanesulfonyl chloride were added, whilst ice-cooling, to a solution of 2.13 g of (2S, 4S)-1-(2-hydroxyethyl)-4-(4-methoxybenzylthio)-2-methylcarbamoyl-pyrrolidine dissolved in 45 ml of dry tetrahydrofuran, and the mixture was stirred at 0° to 5° C. for 30 minutes. At the end of this time, the crystals which precipitated were collected by filtration and washed with tetrahydrofuran. The filtrate and washings were combined and dried over anhydrous magnesium sulfate, and the solvent was removed by distillation under reduced pressure, to afford 2.50 g of the title compound as an oil.

Infrared Absorption Spectrum (liquid film) $\delta_{max}$ cm$^{-1}$: 1664, 1510, 1350, Nuclear Magnetic Resonance Spectrum (CDCl$_3$, 50 MHz) $\delta$ ppm: 1.55–4.10 (8H, multiplet); 2.81 (3H, doublet, J=5.0 Hz); 3.05 (3H, singlet); 3.70 (2H, singlet); 3.80 (3H, singlet); 4.18–4.49 (2H, multiplet); 6.87, 7.26 (4H, A₂B₂, J=9.0 Hz); 7.55 (1H, broad singlet).

18-(3) (6S, 8S)-8-(4-Methoxybenzylthio)-4-methyl-5-oxo-1,4-diazabicyclo[4.3.0]nonane 347 mg of sodium hydride (as a 55% w/w suspension in mineral oil) was added, whilst ice-cooling, to a solution of 2.64 g of (2S, 4S)-1-(2-methanesulfonyloxyethyl)-4-(4-methoxybenzylthio)-2-methylcarbamoylpyrrolidine dissolved in 30 ml of dry dimethylformamide, and the mixture was stirred at 0° to 5° C. for 30 minutes and then at 30° C. for 2 hours. The reaction mixture was then poured into an aqueous solution of sodium chloride and extracted with ethyl acetate. The extract was washed with an aqueous solution of sodium chloride, dried over anhydrous magnesium sulfate and freed from the solvent by distillation under reduced pressure. The residue was purified by column chromatography through silica gel (eluted with a 5:1 by volume mixture of acetonitrile and methanol), to afford 1.75 g of the title compound as an oil.

Infrared Absorption Spectrum (CHCl₃) δ$_{max}$ cm$^{-1}$: 1637, 1508, 1240.

Magnetic Resonance Spectrum (CDCl₃, 270 MHz) δ ppm: 1.88–2.01 (1H, multiplet); 2.59 (1H, doublet of triplets, J=13.18, 8.06 Hz); 2.75–2.98 (3H, multiplet); 2.94 (3H, singlet); 3.00–3.24 (3H, multiplet); 3.30 (1H, triplet, J=8.06 Hz); 3.48–3.62 (1H, multiplet); 3.70 (2H, singlet); 3.80 (3H, singlet); 6.84, 7.33 (4H, A₂B₂, J=8.80 Hz).

18-(4) (6S, 8S)-1,4-Dimethyl-8-(4-methoxybenzylthio)-oxo-4-aza-1-azoniabicyclo[4.3.0]nonane fluorosulfonate 461 μl of methyl fluorosulfonate was added, whilst (4-methoxybenzylthio)-4-methyl-5-oxo-1,4-diazabicyclo[4.3.0]nonane dissolved in 60 ml of methylene chloride, and the mixture was stirred at room temperature for 2 hours. At the end of this time, the mixture was diluted with diethyl ether, and the resulting crystals were collected by filtration and dried under reduced pressure, to afford 2.09 g of the title compound as colorless crystals, melting at 208°–210° C.

Infrared Absorption Spectrum (KBr) δ$_{max}$ cm$^{-1}$: 1651, 1512, 1295.

Nuclear Magnetic Resonance Spectrum (hexadeuterated dimethyl sulfoxide, 270 MHz) δ ppm: 2.16–2.33 (1H, multiplet); 2.79–2.95 (1H, multiplet); 2.89 (3H, singlet); 3.23 (3H, singlet); 3.38 (1H, broad singlet); 3.56–4.02 (6H, multiplet); 3.74 (3H, singlet); 3.80 (2H, singlet); 4.37 (1H, triplet, J=8.30 Hz); 6.90, 7.26 (4H, A₂B₂, J=8.79Hz).

PREPARATION 19

3-Mercapto-2-pyrrolidinone trifluoromethanesulfonate 20 ml of trifluoroacetic acid and 0.41 ml of trfluoromethanesulfonic acid were added, whilst ice-cooling, to a solution of 949 mg of 3-(4-methoxybenzylthio)pyrrolidin-2-one in 4 ml of anisole, and then the mixture was stirred at room temperature for 30 minutes. At the end of this time, the reaction mixture was concentrated by evaporation under reduced pressure to leave a residue, which was purified by column chromatography through silica gel, eluted with a 10:1 by volume mixture of ethyl acetate and methanol, to give 728 mg of the title compound as an oil.

Nuclear Magnetic Resonance Spectrum (60 MHz, CDCl₃) δ ppm: 1.75–3.05 (3H, multiplet); 3.30–4.04 (3H, multiplet); 8.12 (1H, broad singlet); 9.32 (1H, broad singlet).

PREPARATION 20

4-Mercapto-2-pyrrolidinone 20-(1) 15.6 g of triphenylphosphine were added to a suspension of 3 g of 4-hydroxy-2-pyrrolidinone in 200 ml of tetrahydrofuran, and then the mixture was stirred at room temperature for 5 minutes, after which it was cooled to −20° C. A solution of 9.3 ml of diethyl azodicarboxylate in 9 ml of tetrahydrofuran was added dropwise, whilst cooling at −12° C. to −20° C., to the previous solution. The mixture was then stirred at 0°–5° C. for 5 minutes, after which it was again cooled to −20° C. 4.2 ml of thioacetic acid were then added dropwise to the mixture, whilst cooling at −18° C. to −20° C. The mixture was then warmed to 0–5° C. and stirred at that temperature for 2 hours. At the end of this time, the reaction mixture was concentrated by evaporation under reduced pressure. The residue was purified first by column chromatography through silica gel, eluted with a 10:1 by volume mixture of ethyl acetate and methanol, and then by column chromatography through silica gel, eluted with a 2:1 by volume mixture of acetonitrile and benzene, to give 2.45 g of 4-acetylthio-2-pyrrolidinone as colorless crystals.

Nuclear Magnetic Resonance Spectrum (CDCl₃, 90 MHz) δ ppm: 2.00–4.44 (5H. multiplet); 2.31 (3H, singlet); 7.13 (1H, broad singlet).

20-(2) 1.82 of the product obtained in step (1) were dissolved in 30 ml of methanol. 2.3 ml of a 28% w/v methanolic solution of sodium methoxide were added dropwise, whilst ice-cooling, to the previous solution, and then the mixture was stirred for 30 minutes. 12 ml of 1N hydrochloric acid were then added, whilst ice-cooling, to the reaction mixture, which was then concentrated by evaporation under reduced pressure to leave a powdery residue. The residue was extracted with 50 ml of ethyl acetate and the extract was dried over anhydrous sodium sulfate. The extract was concentrated by evaporation under reduced pressure to give 1.35 g of the title compound as colorless crystals.

Infrared Absorption Spectrum (KBr) δ$_{max}$ cm$^{-1}$: 1687, 1681, 1250.

Nuclear Magnetic Resonance Spectrum (CDCl₃, 270 MHz) 1.95 (1H, doublet, J=7.0 Hz); 2.30 (1H, doublet of doublets, J=17.2 & 6.6 Hz); 2.80 (1H, doublet of doublets, J=17.2 & 7.1 Hz); 3.31 (1H, doublet of doublets, J=9.9, 5.2 & 0.8 Hz); 3.59–3.73 (1H, multiplet); 3.80 (1H, doublet of doublets of doublets, J=9.9, 7.3 & 0.7 Hz); 6.13 (1H, broad singlet).

PREPARATIONS 21 TO 25

Following procedures similar to those described above in preparations 1 to 4, the following compounds were also prepared:

PREPARATION 21

4S)-1,1-Dimethyl-4-(4-methoxybenzylthio)-2-methoxycarbonylpyrrolidinium fluorosulfonate Infrared Absorption Spectrum (liquid film) δ$_{max}$ cm$^{-}$: 1747, 1512.

Nuclear Magnetic Resonance Spectrum (D$_2$O, 270 MHz) 2.16-2.29 (1H, multiplet); 2.74-2.92 (1H, multiplet); 3.05 (3H, singlet); 3.12 (3H, singlet); 3.38-3.73 (3H, multiplet); 3.65 (3H, singlet); 3.66 (3H, singlet); 3.68 (2H, singlet); 4.32 (1H, doublet of doublets, J=10.99 & 7.69 Hz); 7.16, 7.82 (4H, A$_2$B$_2$, J=8.61 Hz).

PREPARATION 22

(2R, 4S)-2-Carbamoyl-4-(4-methoxybenzylthio)-1,1-dimethylpyrrolidinium fluorosulfonate Infrared Absorption Spectrum (KBr) $\delta_{max}$ cm$^{-1}$: 1698, 1512.

Nuclear Magnetic Resonance Spectrum (D$_2$O, 270 MHz) 2.19-2.30 (1H, multiplet); 2.57-2.70 (1H, multiplet); 2.93 (3H, singlet); 3.15 (3H, singlet); 3.30 (1H, doublet of doublets, J=12.09 & 7.51 Hz); 3.47-3.60 (1H, multiplet); 3.66 (3H, singlet); 3.69 (2H, singlet); 3.77 (1H, doublet of doublets, J=12.09 & 8.06 Hz); 4.26 (1H, triplet, J=8.43 Hz); 6.82, 7.18 (4H, A$_2$B$_2$, J=8.61 Hz).

PREPARATION 23

(2R, 4S)-1,1-Dimethyl-2-(N,N-dimethylcarbamoyl)-4-(4-methoxybenzylthio)pyrrolidinium fluorosulfonate Infrared Absorption Spectrum (liquid film) $\delta_{max}$ cm$^{-1}$: 1651, 1511.

Nuclear Magnetic Resonance Spectrum (D$_2$O, 270 MHz) $\delta$ ppm: 2.17-2.29 (1H, multiplet); 2.46-2.58 (1H, multiplet); 2.78 (3H, singlet); 2.94 (3H, singlet); 2.98 (3H, singlet); 3.10 (3H, singlet); 3.26 (1H, doublet of doublets, J=12.09 & 6.96 Hz); 3.51-3.63 (1H, multiplet); 3.65 (3H, singlet); 3.69 (2H, singlet); 3.84 (1H, doublet of doublets, J=12.09 & 8.62 Hz); 4.75 (1H, doublet of doublets, J=7.69 & 6.96 Hz); 6.82, 7.17 (4H, A$_2$B$_2$, J=8.78 Hz).

PREPARATION 24

(2S, 4S)-2-Cyclopropylcarbamoyl-1,1-dimethyl-4-(4-methoxybenzylthio)pyrrolidinium fluorosulfonate Infrared Absorption Spectrum (liquid film) $\delta_{max}$ cm$^{-1}$: 1685, 1532, 1512.

Nuclear Magnetic Resonance Spectrum (D$_2$O, 270 MHz) $\delta$ ppm: 0.26-2.66 (4H, multiplet); 2.00-3.65 (6H, multiplet); 2.96 (3H, singlet); 2.98 (3H, singlet); 3.65 (3H, singlet); 3.68 (2H, singlet); 3.92 (1H, triplet, J=7.86 Hz); 6.81, 3.17 (4H, A$_2$B$_2$, J=8.80 Hz).

PREPARATION 25

(6S, 8S)-5-Oxo-8-(4-methoxybenzylthio)-1-methyl-4-aza-1-azoniabicyclo[4.3.0]nonane fluorosulfonate Infrared Absorption Spectrum (KBr) $\delta_{max}$ cm$^{-1}$: 1680, 1609, 1512, 1246.

Nuclear Magnetic Resonance Spectrum (D$_2$O, 270 MHz) 2.10-2.24 (1H, multiplet); 2.73-2.90 (1H, multiplet); 3.65 (3H, singlet); 3.67 (2H, singlet); 3.36-3.85 (7H, multiplet); 4.18 (1H, triplet, J=8.43 Hz); 6.82, 7.17 (4H, A$_2$B$_2$, J=8.79 Hz).

We claim:

1. A compound of formula (I):

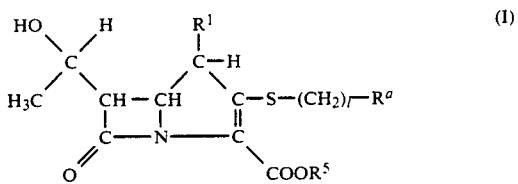

in which

R$^a$ is a group of formula (III):

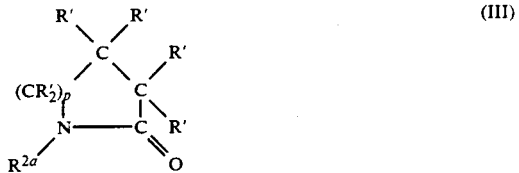

and in which:

one of the symbols R' represent a bond to the remainder of the compound of formula (I), in said formula (III) the others of the symbols R' all represent hydrogen atoms;

R$^1$ represents a methyl group;

R$^{2a}$ represents a hydrogen atom, a C$_1$-C$_6$ alkyl group or a C$_1$-C$_6$ alkanoyl group.

—COOR$^5$ represents a carboxy group, l is zero, or an integer from 1 to 3;

p is zero or the integer 1 or 2.

2. The compound of claim 1, wherein R$^5$ represents: a C$_1$-C$_{20}$ alkyl group; C$_3$-C$_7$ cycloalkyl group; an aralkyl group in which the alkyl part is C$_1$-C$_3$ and the aromatic group is C$_6$-C$_{14}$ and is unsubstituted or has at least one substituent (c) selected from the group consisting of: C$_1$-C$_4$ alkyl groups, C$_1$-C$_4$ alkoxy groups, C$_1$-C$_4$ haloalkyl groups, C$_1$-C$_3$ alkylenedioxy groups, halogen atoms, cyano groups and nitro groups; a C$_2$-C$_6$ alkenyl group which is unsubstituted or has at least one substituent (a) selected from the group consisting of hydroxy groups, cyano groups, carbamoyloxy groups, azido groups, carboxy groups, nitro groups, oxo groups, halogen atoms, C$_1$-C$_6$ alkoxy groups, C$_1$-C$_6$ alkanoyl groups, C$_1$-C$_6$ alkanoyloxy groups, C$_1$-C$_6$ alkanoylamino groups, C$_2$-C$_7$ alkoxycarbonyl groups, groups of formula —NR$^{10}$R$^{11}$ and —CONR$^{12}$R$^{13}$ in which R$^{10}$, R$^{11}$, R$^{12}$ and R$^{13}$ are independently selected from the group consisting of hydrogen atoms, C$_1$-C$_6$ alkyl groups and C$_1$-C$_6$ alkanoyl groups, groups of formula —SO$_2$NR$^{14}$R$^{15}$ and —S(O)$_k$R$^{16}$ wherein R$^{14}$, R$^{15}$ and R$^{16}$ are independently selected from the group consisting of C$_1$-C$_6$ alkyl groups and k is zero or an integer 1 or 2, and groups of formula —NHSO$_2$R$^{17}$ —N=CR$^{18}$NR$^{19}$R$^{20}$, —N=CR$^{21}$CR$^{22}$=NR$^{23}$ and —C(=NH)NR$^{24}$R$^{25}$ wherein R$^{17}$ to R$^{25}$ are independently selected from the group consisting of hydrogen atoms and C$_1$-C$_6$ alkyl groups; a halogenated C$_1$-C$_6$ alkyl group; a substituted silylalkyl group in which alkyl part is C$_1$-C$_6$ and the silyl group has up to 3 substituents selected from the group consisting of C$_1$-C$_6$ alkyl groups and phenyl groups which are unsubstituted or have at least one substituent selected from the group consisting of substituents (a) defined above; a phenyl group which is unsubstituted or has at least one $C_1$-$C_4$ alkyl or acylamino substituent; a phenacyl group which is unsubstituted or has at least one substituent selected from the group consisting of substituents (a) defined above; a cyclic or acyclic terpenyl group; an alkoxymethyl group, in which the alkoxy part is $C_1$-$C_6$ which is unsubstituted or is itself substituted by a single unsubstituted alkoxy group; an aliphatic acyloxymethyl group, in which the acyl group is an alkanoyl group; a higher aliphatic acyloxyalkyl group in which the acyl group is an alkanoyl group, and the alkyl part is $C_2$-$C_6$; a cycloalkyl-substituted aliphatic acyloxyalkyl group, in which the acyl group is an alkanoyl group, the cycloalkyl substituent is $C_3$-$C_7$, and the alkyl part is a $C_1$-$C_6$ alkyl group; an alkoxycarbonyl-oxyalkyl group, in which the alkoxy part is $C_1$-$C_{10}$, and the alkyl part is $C_1$-$C_6$; a cycloalkylcarbonyloxyalkyl or cycloalkyloxycarbonyl-oxyalkyl group, in which the cycloalkyl group is $C_3$-$C_{10}$, is mono- or polycyclic and is optionally substituted by at least one $C_1$-$C_4$ alkyl group, and the alkyl group is a $C_1$-$C_6$ alkyl group; a cyclalkylalkoxycarbonyloxyalkyl group in which the alkoxy group has a single cycloalkyl substituent, the cycloalkyl substituent being $C_3$-$C_{10}$ and mono- or polycyclic; a terpenylcarbonyloxyalkyl or terpenyloxycarbonyloxyalkyl group; a 5-alkyl- or 5-phenyl- substituted (2-oxo-1,3-dioxolen-4-yl)alkyl group in which each alkyl group is $C_1$-$C_6$ and in which the phenyl group is unsubstituted or has at least one substituent selected from the group consisting of substituents (c) defined above; a phthalidyl group; an indanyl group; or a 2-oxo-4,5,6,7-tetrahydro-1,3-benzodioxolen-4-yl group.

3. The composition of claim 1, wherein $R^5$ represents: a $C_1$-$C_6$ alkyl group; a $C_3$-$C_7$ cycloalkyl group; an aralkyl group in which the alkyl part is $C_1$-$C_3$ and the aromatic group is $C_6$-$C_{14}$ and is unsubstituted or has at least one substituent (c) selected from the group consisting of $C_1$-$C_4$ alkyl groups, $C_1$-$C_4$ alkoxy groups, $C_1$-$C_4$ haloalkyl groups, $C_1$-$C_3$ alkylenedioxy groups, halogen atoms, cyano groups and nitro groups; a $C_2$-$C_6$ alkenyl group which is unsubstituted or has at least one substituent (a) selected from the group consisting of hydroxy groups, cyano groups, carbamoyloxy groups, azido groups, carboxy groups, nitro groups, oxo groups, halogen atoms, $C_1$-$C_6$ alkoxy groups, $C_1$-$C_6$ alkanoyl groups, $C_1$-$C_6$ alkanoyloxy groups, $C_1$-$C_6$ alkanoylamino groups, $C_2$-$C_7$ alkoxycarbonyl groups, groups of formula —$NR^{10}R^{11}$ and —$CONR^{12}R^{13}$ in which $R^{10}$, $R^{11}$, $R^{12}$ and $R^{13}$ are independently selected from the group consisting of hydrogen atoms, $C_1$-$C_6$ alkyl groups and $C_1$-$C_6$ alkanoyl groups, groups of formula —$SO_2NR^{14}R^{15}$ and —$S(O)_kR^{16}$ wherein $R^{14}$, $R^{15}$ and $R^{16}$ are independently selected from the group consisting of $C_1$-$C_6$ alkyl groups and k is zero or an integer 1 or 2, and groups of formula —$NHSO_2R^{17}$ —$N=CR^{18}NR^{19}R^{20}$, —$N=CR^{21}CR^{22}=NR^{23}$ and —$C(=NH)NR^{24}R^{25}$ wherein $R^{17}$ to $R^{25}$ are independently selected from the group consisting of hydrogen atoms and $C_1$-$C_6$ alkyl groups; a halogenated $C_1$-$C_6$ alkyl group; a substituted silylalkyl group in which alkyl part is $C_1$-$C_6$ and the silyl group has up to 3 substituents selected from the group consisting of $C_1$-$C_6$ alkyl groups and phenyl groups which are unsubstituted or have at least one substituent selected from the group consisting of substituents (a) defined above; a phenyl group which is unsubstituted or has at least one $C_1$-$C_4$ alkyl or acylamino substituent; a phenacyl group which is unsubstituted or has at least one substituent selected from the group consisting of substituents (a) defined above; a cyclic or acyclic terpenyl group; an alkoxymethyl group, in which the alkoxy part is $C_1$-$C_6$ which is unsubstituted or is itself substituted by a single unsubstituted alkoxy group; an aliphatic acyloxymethyl group, in which the acyl group is a $C_2$-$C_6$ alkanoyl group; a higher aliphatic acyloxyalkyl group in which the acyl group is a $C_2$-$C_6$ alkanoyl group, and the alkyl part is $C_2$-$C_4$; a cycloalkyl-substituted aliphatic acyloxyalkyl group, in which the acyl group is a $C_2$-$C_6$ alkanoyl group, the cycloalkyl substituent is $C_3$-$C_7$, and the alkyl part is a $C_1$-$C_4$ alkyl group; a 1-(alkoxycarbonyloxy)ethyl group, in which the alkoxy part is $C_1$-$C_4$, and the alkyl part is $C_1$-$C_4$; a cycloalkylcarbonyloxyalkyl or cycloalkyloxycarbonyloxyalkyl group, in which the cycloalkyl group is $C_3$-$C_7$, is mono- or polycyclic and is optionally substituted by at least one $C_1$-$C_4$ alkyl group, and the alkyl group is a $C_1$-$C_4$ alkyl group; a cycloalkylalkoxycarbonyloxyalkyl group in which the alkoxy group has a single cycloalkyl substituent, the cycloalkyl substituent being $C_3$-$C_7$ and mono- and polycyclic; a terpenylcarbonyloxyalkyl or terpenyloxycarbonyloxyalkyl group; a 5-alkyl- or 5-phenyl- substituted (2-oxo-1,3-dioxolen-4-yl)alkyl group in which each alkyl group is $C_1$-$C_4$, and in which the phenyl group is unsubstituted or has at least one substituent selected from the group consisting of substituents (c) defined above; a phthalidyl group; an indanyl group; or a 2-oxo-4,5,6,7-tetrahydro-1,3-benzodioxolen-4-yl group.

4. The compound of claim 1, in which: $R^1$ represents a hydrogen atom or a methyl group; l is zero or an integer 1 or 2.

5. The compound of claim 1, in which:
p is 1; and
$R^{2a}$ is a hydrogen atom, a $C_1$-$C_4$ alkyl group, or a $C_1$-$C_4$ alkanoyl group.

6. The compound of claim 1, in which:
the group of formula (III) is a pyrrolidin-2-one-4-yl group, which has the group $R^{2a}$ at its nitrogen atom; and
$R^{2a}$ is a hydrogen atom, a methyl, ethyl, propyl, butyl, formyl, acetyl, propionyl or butyryl group.

7. The compound of claim 1, in which:
the group of formula (III) is a pyrrolidin-2-one-4-yl group, which has the group $R^{2a}$ at its nitrogen atom; and
$R^{2a}$ is a hydrogen atom.

8. The compound of claim 1, wherein the 1-hydroxyethyl group at the 6-penem position is in the 1(R)-hydroxyethyl configuration.

9. The compound of claim 1, wherein $R^1$ represents a hydrogen atom, and the penem system has the (5R, 6S) configuration.

10. The compound of claim 1, wherein $R^1$ represents a methyl group, and the penem system has the (1R, 5S, 6S) configuration.

11. The compound of claim 1, selected from the group consisting of pivaloyloxymethyl 2-(2-oxo-4-pyrrolidinylthio)-6-(1-hydroxyethyl)-1-methyl-1-carapen-2-em-3-carboxylate.

12. The compound of claim 1, selected from the group conssiting of pivaloyloxymethyl (1R, 5S, 6S)-2-(2-oxo-4-pyrrolidinylthio)-6-[(1R)-1-hydroxyethyl]-1-methyl-1-carbapen-2-em-3-carboxylate.

13. The compound of claim 1, selected from the group consisting of (1-methylcyclohexan-1-yl)carbonyloxymethyl 2-(2-oxo-4-pyrrolidinylthio)-6-[(1R)-1-hydroxyethyl]-1-methyl-1-carbapen-2-em-3-carboxylate.

14. The compound of claim 1, selected from the group consisting of (1-methylcyclohexan-1-yl)carbonyloxymethyl (1R, 5S, 6S)-2-(2-oxo-4-pyrrolidinylthio)-6-[(1R)-1-hydroxyethyl]-1-methyl-1-carbapen-2-em-3-carboxylate.

15. The compound of claim 1, selected from the group consisting of 1-(cyclopentyloxycarbonyloxy)ethyl 2-(2-oxo-4-pyrrolidinylthio)-6-[(1R)-1-hydroxyethyl]-1-methyl-1-carbapen-2-em-3-carboxylate.

16. The compound of claim 1, selected from the group consisting of 1-(cyclopentyloxycarbonyloxy)ethyl (1R, 5S, 6S)-2-(2-oxo-4-pyrrolidinylthio)-6-[(1R)-1-hydroxyethyl]-1-methyl-1-carbapen-2-em-3-carboxylate.

17. A pharmaceutical composition comprising an effective amount of an antibiotic in admixture with a pharmaceutically acceptable carrier or diluent, wherein the antibiotic is at least one compound selected from the group consisting of compounds of formula (I); as defined in claim 1.

18. The composition of claim 17, wherein $R^5$ represents: a $C_1$-$C_{20}$ alkyl group; a $C_3$-$C_7$ cycloalkyl group; an aralkyl group in which the alkyl part is $C_1$-$C_3$ and the aromatic group is $C_6$-$C_{14}$ and is unsubstituted or has at least one substituent (c) selected from the group consisting of $C_1$-$C_4$ alkyl groups, $C_1$-$C_4$ alkoxy groups, $C_1$-$C_4$ haloalkyl groups, $C_1$-$C_3$ alkeylenedioxy groups, halogen atoms, cyano groups and nitro groups; a $C_2$-$C_6$ alkenyl group which is unsubstituted or has at least one substituent (a) selected from the group consisting of hydroxy groups, cyano groups, carbamoyloxy groups, azido groups, carboxy groups, nitro groups, oxo groups, halogen atoms, $C_1$-$C_6$ alkoxy groups, $C_1$-$C_6$ alkanoyl groups, $C_1$-$C_6$ alkanoyloxy groups, $C_1$-$C_6$ alkanoylamino groups, $C_2$-$C_7$ alkoxycarbonyl groups, groups of formula $-NR^{10}R^{11}$ and $-CONR^{12}R^{13}$ in which $R^{10}$, $R^{11}$, $R^{12}$ and $R^{13}$ are independently selected from the group consisting of hydrogen atoms, $C_1$-$C_6$ alkyl groups and $C_1$-$C_6$ alkanoyl groups, group of formula $-SO_2NR^{14}R^{15}$ and $-S(O)_kR^{16}$ wherein $R^{14}$, $R^{15}$ and $R^{16}$ are independently selected from the group consisting of $C_1$-$C_6$ alkyl groups and k is zero or an integer 1 or 2, and groups of formula $-NHSO_2R^{17}$ $-N=CR^{18}NR^{19}R^{20}$, $-N=CR^{21}CR^{22}=NR^{23}$ and $-C(=NH)NR^{24}R^{25}$ wherein $R^{17}$ to $R^{25}$ are independently selected from the group consisting of hydrogen atoms and $C_1$-$C_6$ alkyl groups; a halogenated $C_1$-$C_6$ alkyl group; a substituted silylalkyl group in which alkyl part is $C_1$-$C_6$ and the silyl group has up to 3 substituents selected from the group consisting of $C_1$-$C_6$ alkyl groups and phenyl groups which are unsubstituted or have at least one substituent selected from the group consisting of substituents (a) defined above; a phenyl group which is unsubstituted or has at least one $C_1$-$C_4$ alkyl or acylamino substituent; a phenacyl group which is unsubstituted or has at least one substituent selected from the group consisting of substituents (a) defined above; a cyclic or acyclic terpenyl group; an alkoxymethyl group, in which the alkoxy part is $C_1$-$C_6$ which is unsubstituted or is itself substituted by a single unsubstituted alkoxy group; an aliphatic acyloxymethyl group, in which the acyl group is an alkanoyl group; a higher aliphatic acyloxyalkyl group in which the acyl group is an alkanoyl group, and the alkyl part is $C_2$-$C_6$; a cycloalkyl-substituted aliphatic acyloxyalkyl group, in which the acyl group is an alkanoyl group, the cycloalkyl substituent is $C_3$-$C_7$, and the alkyl part is a $C_1$-$C_6$ alkyl group; an alkoxycarbonyl-oxyalkyl group, in which the alkoxy part is $C_1$-$C_{10}$, and the alkyl part is $C_1$-$C_6$; a cycloalkylcarbonyloxyalkyl or cycloalkyloxycarbonyl-oxyalkyl group, in which the cycloalkyl group is $C_3$-$C_{10}$, is mono-or polycyclic and is optionally substituted by at least one $C_1$-$C_4$ alkyl group, and the alkyl group is a $C_1$-$C_6$ alkyl group; a cyclalkylalkoxycarbonyloxyalkyl group in which the alkoxy group has a single cycloalkyl substituent, the cycloalkyl substituent being $C_3$-$C_{10}$ and mono- or poly-cyclic; a terpenylcarbonyloxyalkyl or terpenyloxycarbonyloxyalkyl group; a 5-alkyl- or 5-phenyl- substituted (2-oxo-1,3-dioxolen-4-yl)alkyl group in which each alkyl group is $C_1$-$C_6$ and in which the phenyl group is unsubstituted or has at least one substituent selected from the group consisting of substituents (c) defined above; a phthalidyl group; an indanyl group; or a 2-oxo-4,5,6,7-tetrahydro-1,3-benzodioxolen-4-yl group.

19. The composition of claim 17, wherein:
$R^1$ represents a hydrogen atom or a methyl group;
l is zero or an integer 1 or 2, (m+n) is an integer 2, 3, 4, 5 or 6; Y represents a single bond, an oxygen atom, a sulfur atom or a group of formula $R^8N<$.

20. The composition of claim 17, in which:
p is 1; and
$R^{2a}$ is a hydrogen atom, a $C_1$-$C_4$ alkyl group, or a $C_1$-$C_4$ alkanoyl group.

21. The composition of claim 17, wherein the antibiotic is selected from the group consisting of:
pivaloyloxymethyl 2-(2-oxo-4-pyrrolidinylthio)-6-(1-hydroxymethyl)-1-methyl-1-carbapen-2-em-3-carboxylate;
(1-methylcyclohexan-1-yl)carbonyloxymethyl 2-(2-oxo-4-pyrrolidinylthio)-6-(1-hydroxymethyl)-1-methyl-1-carbapen-2-em-3-carboxylate;
1-(cyclopentyloxycarbonyloxy)ethyl 2-(2-oxo-4-pyrrolidinylthio)-6-(1-hydroxymethyl)-1-methyl-1-carbapen-2-em-3-carboxylate.

22. The composition of claim 17, wherein the antibiotic is selected from the group consisting of:
pivaloyloxymethyl (1R, 5S, 6S)- 2-(2-oxo-4-pyrrolidinylthio)-6-((1R) -1-hydroxymethyl)-1-methyl-1-carbapen-2-em-3-carboxylate;
(1-methylcyclohexan-1-yl)carbonyloxymethyl (1R, 5S, 6S)-2-(2-oxo-4-pyrrolidinylthio)-6-((1R)-1-hydroxymethyl)-1-methyl-1-carbapen-2-em-3-carboxylate;
1-(cyclopentyloxycarbonyloxy)ethyl (1R, 5S, 6S)-2-(2-oxo-4-pyrrolidinylthio)-6-((1R)-1-hydroxymethyl)-1-methyl-1-carbapen-2-em-3-carboxylate.

and pharmaceutically acceptable salts thereof.

23. A method for the treatment or prevention of microbial infection by the administration to a mammal of an effective amount of an antibiotic, wherein the antibiotic is at least one compound selected from the group consisting of compounds of formula (I), as defined in claim 1.

24. The method of claim 23, wherein $R^5$ represents a $C_1$-$C_{20}$ alkyl group; a $C_3$-$C_7$ cycloalkyl group; an aralkyl group in which the alkyl part is $C_1$-$C_3$ and the aromatic group is $C_6$-$C_{14}$ and is unsubstituted or has at least one substituent (c) selected from the group consisting of $C_1$-$C_4$ alkyl groups, $C_1$-$C_4$ alkoxy groups, $C_1$-$C_4$ haloalkyl groups, $C_1$-$C_3$ alkylenedioxy groups, halogen atoms, cyano groups and nitro groups; a $C_2$-$C_6$ alkenyl group which is unsubstituted or has at least one substituent (a) selected from the group consisting of hydroxy groups, cyano groups, carbamoyloxy groups, azido groups, carboxy groups, nitro groups, oxo groups, halogen atoms, $C_1$-$C_6$ alkoxy groups, $C_1$-$C_6$ alkanoyl groups, $C_1$-$C_6$ alkanoyloxy groups, $C_1$-$C_6$ alkanoylamino groups, $C_2$-$C_7$ alkoxycarbonyl groups, groups of formula $-NR^{10}R^{11}$ and $-CONR^{12}R^{13}$
   in which $R^{10}$, $R^{11}$, $R^{12}$ and $R^{13}$ are independently selected from the group consisting of hydrogen atoms, $C_1$-$C_6$ alkyl groups and $C_1$-$C_6$ alkanoyl groups,
groups of formula $-SO_2NR^{14}R^{15}$ and $-S(O)_kR^{16}$
   wherein $R^{14}$, $R^{15}$ and $R^{16}$ are independently selected from the group consisting of $C_1$-$C_6$ alkyl groups and k is zero or an integer 1 or 2, and
groups of formula $-NHSO_2R^{17}$ $-N=CR^{18}NR^{19}R^{20}$, $-N=CR^{21}CR^{22}=NR^{23}$ and $-C(=NH)NR^{24}R^{25}$
   wherein $R^{17}$ to $R^{25}$ are independently selected from the group consisting of hydrogen atoms and $C_1$-$C_6$ alkyl groups; a halogenated $C_1$-$C_6$ alkyl group; a substituted silylalkyl group in which alkyl part is $C_1$-$C_6$ and the silyl group has up to 3 substituents selected from the group consisting of $C_1$-$C_6$ alkyl groups and phenyl groups which are unsubstituted or have at least one substituent selected from the group consisting of substituents (a) defined above; a phenyl group which is unsubstituted or has at least one $C_1$-$C_4$ alkyl or acylamino substituent; a phenacyl group which is unsubstituted or has at least one substituent selected from the group consisting of substituents (a) defined above; a cyclic or acyclic terpenyl group; an alkoxymethyl group, in which the alkoxy part is $C_1$-$C_6$ which is unsubstituted or is itself substituted by a single unsubstituted alkoxy group; an aliphatic acyloxymethyl group, in which the acyl group is an alkanoyl group; a higher aliphatic acyloxyalkyl group in which the acyl group is an alkanoyl group, and the alkyl part is $C_2$-$C_6$; a cycloalkyl-substituted aliphatic acyloxyalkyl group, in which the acyl group is an alkanoyl group, the cycloalkyl substituent is $C_3$-$C_7$, and the alkyl part is a $C_1$-$C_6$ alkyl group; an alkoxycarbonyl-oxyalkyl group, in which the alkoxy part is $C_1$-$C_{10}$, and the alkyl part is $C_1$-$C_6$; a cycloalkylcarbonyloxyalkyl or cycloalkyloxycarbonyl-oxyalkyl group, in which the cycloalkyl group is $C_3$-$C_{10}$, is mono- or poly-cyclic and is optionally substituted by at least one $C_1$-$C_4$ alkyl group, and the alkyl group is a $C_1$-$C_6$ alkyl group; a cyclalkylalkoxycarbonyloxyalkyl group in which the alkoxy group has a single cycloalkyl substituent, the cycloalkyl substituent being $C_3$-$C_{10}$ and mono- or poly-cyclic; a terpenylcarbonyloxyalkyl or terpenyloxycarbonyloxyalkyl group; a 5-alkyl- or 5-phenyl- substituted (2-oxo-1,3-dioxolen-4-yl)alkyl group in which each alkyl group is $C_1$-$C_6$ and in which the phenyl group is unsubstituted or has at least one substituent selected from the group consisting of substituents (c) defined above; a phthalidyl group; an indanyl group; or a 2-oxo-4,5,6,7-tetrahydro-1,3-benzodioxolen-4-yl group.

25. The composition of claim 23, wherein:
$R^1$ represents a hydrogen atom or a methyl group;
l is zero or an integer 1 or 2.

26. The composition of claim 23, in which:
p is 1; and
$R^{2a}$ is a hydrogen atom, a $C_1$-$C_4$ alkyl group, or a $C_1$-$C_4$ alkanoyl group.

27. The method of claim 23, wherein the antibiotic is selected from the group consisting of:
pivaloyloxymethyl 2-(2-oxo-4-pyrrolidinylthio)-6-(1-hydroxymethyl)-1-methyl-1-carbapen-2-em-3-carboxylate;
(1-methylcyclohexan-1-yl)carbonyloxymethyl 2-(2-oxo-4-pyrrolidinylthio)-6-(1-hydroxymethyl)-1-methyl-1-carbapen-2-em-3-carboxylate;
1-(cyclopentyloxycarbonyloxy)ethyl 2-(2-oxo-4-pyrrolidinylthio)-6-(1-hydroxymethyl)-1-methyl-1-carbapen-2-em-3-carboxylate.

28. The composition of claim 23, wherein the antibiotic is selected from the group consisting of:
pivaloyloxymethyl (1R, 5S, 6S)- 2-(2-oxo-4-pyrrolidinylthio)-6-((1R) -1-hydroxymethyl)-1-methyl-1-carbapen-2-em-3-carboxylate;
(1-methylcyclohexan-1-yl)carbonyloxymethyl (1R, 5S, 6S)-2-(2-oxo-4-pyrrolidinylthio)-6-((1R)-1-hydroxymethyl)-1-methyl-1-carbapen-2-em-3-carboxylate;
1-(cyclopentyloxycarbonyloxy)ethyl (1R, 5S, 6S)-2-(2-oxo-4-pyrrolidinylthio)-6-((1R)-1-hydroxymethyl)-1-methyl-1-carbapen-2-em-3-carboxylate.

* * * * *

UNITED STATES PATENT AND TRADEMARK OFFICE
CERTIFICATE OF CORRECTION

PATENT NO. : 5,104,867
DATED : April 14, 1992
INVENTOR(S) : KAWAMOTO et al

It is certified that error appears in the above-identified patent and that said Letters Patent is hereby corrected as shown below:

Column 17, after line 60 and before TABLE 2, insert the following:

--
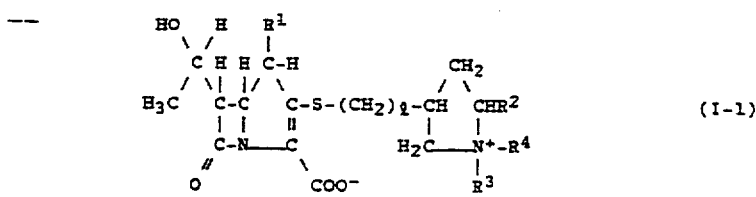

(I-1)

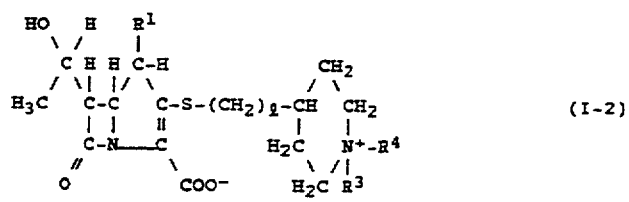

(I-2)

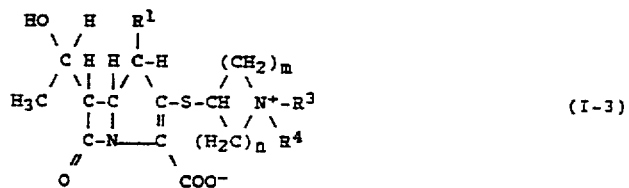

(I-3)

UNITED STATES PATENT AND TRADEMARK OFFICE
CERTIFICATE OF CORRECTION

PATENT NO. : 5,104,867

DATED : April 14, 1992

INVENTOR(S) : KAWAMOTO et al

Page 2 of 14

It is certified that error appears in the above-identified patent and that said Letters Patent is hereby corrected as shown below:

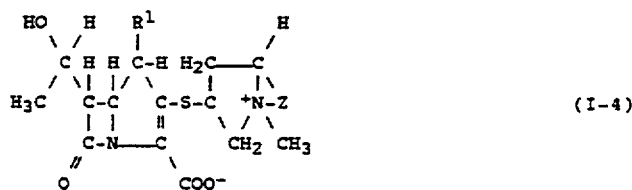

(I-4)

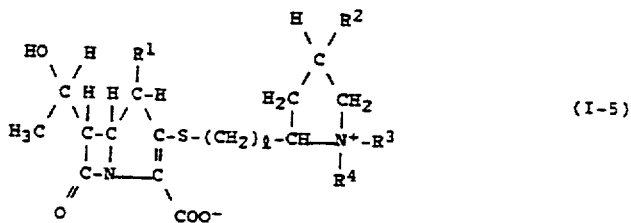

(I-5)

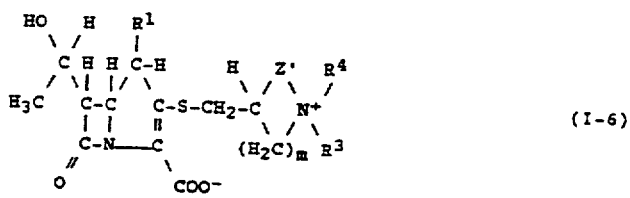

(I-6)

UNITED STATES PATENT AND TRADEMARK OFFICE
CERTIFICATE OF CORRECTION

PATENT NO. : 5,104,867
DATED : April 14, 1992
INVENTOR(S) : KAWAMOTO et al

Page 3 of 14

It is certified that error appears in the above-identified patent and that said Letters Patent is hereby corrected as shown below:

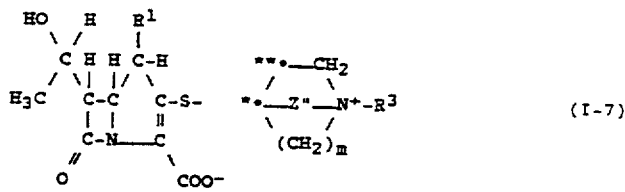

(I-7)

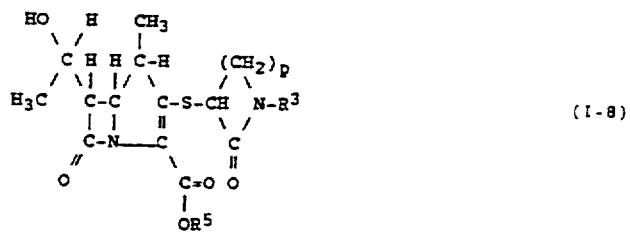

(I-8)

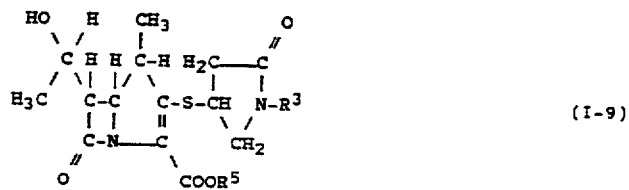

(I-9)

UNITED STATES PATENT AND TRADEMARK OFFICE
CERTIFICATE OF CORRECTION

PATENT NO. : 5,104,867
DATED : April 14, 1992
INVENTOR(S) : KAWAMOTO et al

It is certified that error appears in the above-identified patent and that said Letters Patent is hereby corrected as shown below:

Table 1

| Cpd. No. | $R^1$ | $R^2$ | $R^3$ | $R^4$ | $\ell$ |
|---|---|---|---|---|---|
| 1-1  | Me | Car    | Me        | Me | o |
| 1-2  | H  | Car    | Me        | Me | o |
| 1-3  | Me | Car    | 2-FEt     | Me | o |
| 1-4  | H  | Car    | 2-FEt     | Me | o |
| 1-5  | Me | MeCar  | Me        | Me | o |
| 1-6  | H  | MeCar  | Me        | Me | o |
| 1-7  | Me | Car    | All       | Me | o |
| 1-8  | H  | Car    | All       | Me | o |
| 1-9  | Me | Car    | Et        | Me | o |
| 1-10 | H  | Car    | Et        | Me | o |
| 1-11 | Me | Car    | $-CH_2Car$  | Me | o |
| 1-12 | H  | Car    | $-CH_2Car$  | Me | o |
| 1-13 | Me | Car    | $-CH_2CN$   | Me | o |
| 1-14 | H  | Car    | $-CH_2CN$   | Me | o |
| 1-15 | Me | Car    | $-CH_2COOH$ | Me | o |
| 1-16 | H  | Car    | $-CH_2COOH$ | Me | o |
| 1-17 | Me | Car    | $-CH_2OMe$  | Me | o |
| 1-18 | H  | Car    | $-CH_2OMe$  | Me | o |
| 1-19 | Me | MeCar  | 2-FEt     | Me | o |
| 1-20 | H  | MeCar  | 2-FEt     | Me | o |
| 1-21 | Me | MeCar  | Et        | Me | o |
| 1-22 | H  | MeCar  | Et        | Me | o |
| 1-23 | Me | diMeCar| Me        | Me | o |
| 1-24 | H  | diMeCar| Me        | Me | o |
| 1-25 | Me | diMeCar| Et        | Me | o |
| 1-26 | H  | diMeCar| Et        | Me | o |
| 1-27 | Me | diMeCar| 2-FEt     | Me | o |
| 1-28 | H  | diMeCar| 2-FEt     | Me | o |

UNITED STATES PATENT AND TRADEMARK OFFICE
CERTIFICATE OF CORRECTION

PATENT NO. : 5,104,867
DATED : April 14, 1992
INVENTOR(S) : KAWAMOTO et al

It is certified that error appears in the above-identified patent and that said Letters Patent is hereby corrected as shown below:

Table 1 (cont)

| Cpd. No. | $R^1$ | $R^2$ | $R^3$ | $R^4$ | $l$ |
|---|---|---|---|---|---|
| 1-29 | Me | diMeCar | All | Me | O |
| 1-30 | H | diMeCar | All | Me | O |
| 1-31 | Me | Car | $-CH_2SMe$ | Me | O |
| 1-32 | H | Car | $-CH_2SMe$ | Me | O |
| 1-33 | Me | Car | Prg | Me | O |
| 1-34 | H | Car | Prg | Me | O |
| 1-35 | Me | -CONH(2-FEt) | Me | Me | O |
| 1-36 | H | -CONH(2-FEt) | Me | Me | O |
| 1-37 | Me | -CONMe(2-FEt) | Me | Me | O |
| 1-38 | H | -CONMe(2-FEt) | Me | Me | O |
| 1-39 | Me | -CONMe(2-HOEt) | Me | Me | O |
| 1-40 | H | -CONMe(2-HOEt) | Me | Me | O |
| 1-41 | Me | -CONMe(3-FPr) | Me | Me | O |
| 1-42 | H | -CONMe(3-FPr) | Me | Me | O |
| 1-43 | Me | $-CONMe(-CHF_2)$ | Me | Me | O |
| 1-44 | H | $-CONMe(-CHF_2)$ | Me | Me | O |
| 1-45 | Me | Car | $-CH_2Ac$ | Me | O |
| 1-46 | H | Car | $-CH_2Ac$ | Me | O |
| 1-47 | Me | Car | $-CH_2COOMe$ | Me | O |
| 1-48 | H | Car | $-CH_2COOMe$ | Me | O |
| 1-49 | Me | Car | 2-HOEt | Me | O |
| 1-50 | H | Car | 2-HOEt | Me | O |
| 1-51 | Me | H | Me | Me | O |
| 1-52 | H | H | Me | Me | O |
| 1-53 | Me | H | $-CH_2Car$ | Me | O |
| 1-54 | H | H | $-CH_2Car$ | Me | O |
| 1-55 | Me | H | 2-FEt | Me | O |
| 1-56 | H | H | 2-FEt | Me | O |

UNITED STATES PATENT AND TRADEMARK OFFICE
CERTIFICATE OF CORRECTION

PATENT NO. : 5,104,867
DATED : April 14, 1992
INVENTOR(S) : KAWAMOTO et al

It is certified that error appears in the above-identified patent and that said Letters Patent is hereby corrected as shown below:

Table 1 (cont)

| Cpd. No. | $R^1$ | $R^2$ | $R^3$ | $R^4$ | $\ell$ |
|---|---|---|---|---|---|
| 1-57 | Me | H | $-CH_2CN$ | Me | 0 |
| 1-58 | H | H | $-CH_2CN$ | Me | 0 |
| 1-59 | Me | H | $-CH_2Ac$ | Me | 0 |
| 1-60 | H | H | $-CH_2Ac$ | Me | 0 |
| 1-61 | Me | H | $-CH_2COOMe$ | Me | 0 |
| 1-62 | H | H | $-CH_2COOMe$ | Me | 0 |
| 1-63 | Me | H | $-CH_2COOH$ | Me | 0 |
| 1-64 | H | H | $-CH_2COOH$ | Me | 0 |
| 1-65 | Me | H | 2-HOEt | Me | 0 |
| 1-66 | H | H | 2-HOEt | Me | 0 |
| 1-67 | Me | H | $-CH_2OMe$ | Me | 0 |
| 1-68 | H | H | $-CH_2OMe$ | Me | 0 |
| 1-69 | Me | H | $-CH_2SMe$ | Me | 0 |
| 1-70 | H | H | $-CH_2SMe$ | Me | 0 |
| 1-71 | Me | H | $-CH_2SOMe$ | Me | 0 |
| 1-72 | H | H | $-CH_2SOMe$ | Me | 0 |
| 1-73 | Me | H | $-CH_2SO_2Me$ | Me | 0 |
| 1-74 | H | H | $-CH_2SO_2Me$ | Me | 0 |
| 1-75 | Me | H | All | Me | 0 |
| 1-76 | H | H | All | Me | 0 |
| 1-77 | Me | H | Prg | Me | 0 |
| 1-78 | H | H | Prg | Me | 0 |
| 1-79 | Me | H | Bz | Me | 0 |
| 1-80 | H | H | Bz | Me | 0 |
| 1-81 | Me | H | $-CH_2-cPr$ | Me | 0 |
| 1-82 | H | H | $-CH_2-cPr$ | Me | 0 |
| 1-83 | Me | H | $-CH_2-cPn$ | Me | 0 |
| 1-84 | H | H | $-CH_2-cPn$ | Me | 0 |

UNITED STATES PATENT AND TRADEMARK OFFICE
CERTIFICATE OF CORRECTION

PATENT NO. : 5,104,867
DATED : April 14, 1992
INVENTOR(S) : KAWAMOTO et al

It is certified that error appears in the above-identified patent and that said Letters Patent is hereby corrected as shown below:

Table 1 (cont)

| Cpd. No. | $R^1$ | $R^2$ | $R^3$ | $R^4$ | $l$ |
|---|---|---|---|---|---|
| 1-85 | Me | H | Et | Me | 0 |
| 1-86 | H | H | Et | Me | 0 |
| 1-87 | Me | H | $-CH_2$-diMeCar | Me | 0 |
| 1-88 | H | H | $-CH_2$-diMeCar | Me | 0 |
| 1-89 | Me | H | $-CH_2$-MeCar | Me | 0 |
| 1-90 | H | H | $-CH_2$-MeCar | Me | 0 |
| 1-91 | Me | H | Me | Me | 1 |
| 1-92 | H | H | Me | Me | 1 |
| 1-93 | Me | H | $-CH_2$Car | Me | 1 |
| 1-94 | H | H | $-CH_2$Car | Me | 1 |
| 1-95 | Me | H | Et | Me | 1 |
| 1-96 | H | H | Et | Me | 1 |
| 1-97 | Me | H | $-CH_2$-MeCar | Me | 1 |
| 1-98 | H | H | $-CH_2$-MeCar | Me | 1 |
| 1-99 | Me | H | $-CH_2$-diMeCar | Me | 1 |
| 1-100 | H | H | $-CH_2$-diMeCar | Me | 1 |
| 1-101 | Me | H | All | Me | 1 |
| 1-102 | H | H | All | Me | 1 |
| 1-103 | Me | H | Prg | Me | 1 |
| 1-104 | H | H | Prg | Me | 1 |
| 1-105 | Me | H | Bz | Me | 1 |
| 1-106 | H | H | Bz | Me | 1 |
| 1-107 | Me | H | $-CH_2CN$ | Me | 1 |
| 1-108 | H | H | $-CH_2CN$ | Me | 1 |
| 1-109 | Me | H | $-CH_2COOMe$ | Me | 1 |
| 1-110 | H | H | $-CH_2COOMe$ | Me | 1 |
| 1-111 | Me | H | $-CH_2COOH$ | Me | 1 |
| 1-112 | H | H | $-CH_2COOH$ | Me | 1 |

UNITED STATES PATENT AND TRADEMARK OFFICE
CERTIFICATE OF CORRECTION

PATENT NO. : 5,104,867
DATED : April 14, 1992
INVENTOR(S) : KAWAMOTO et al

It is certified that error appears in the above-identified patent and that said Letters Patent is hereby corrected as shown below:

Table 1 (cont)

| Cpd. No. | $R^1$ | $R^2$ | $R^3$ | $R^4$ | $\ell$ |
|---|---|---|---|---|---|
| 1-113 | Me | H | $-CH_2cPr$ | Me | 1 |
| 1-114 | H | H | $-CH_2cPr$ | Me | 1 |
| 1-115 | Me | H | $-CH_2Ac$ | Me | 1 |
| 1-116 | H | H | $-CH_2Ac$ | Me | 1 |
| 1-117 | Me | H | 2-HOEt | Me | 1 |
| 1-118 | H | H | 2-HOEt | Me | 1 |
| 1-119 | Me | H | $-CH_2OMe$ | Me | 1 |
| 1-120 | H | H | $-CH_2OMe$ | Me | 1 |
| 1-121 | Me | H | $-CH_2SMe$ | Me | 1 |
| 1-122 | H | H | $-CH_2SMe$ | Me | 1 |
| 1-123 | Me | H | 2-(CarO)Et | Me | 1 |
| 1-124 | H | H | 2-(CarO)Et | Me | 1 |
| 1-125 | Me | H | $-CH_2SOMe$ | Me | 1 |
| 1-126 | H | H | $-CH_2SOMe$ | Me | 1 |
| 1-127 | Me | H | $-CH_2SO_2Me$ | Me | 1 |
| 1-128 | H | H | $-CH_2SO_2Me$ | Me | 1 |
| 1-129 | Me | H | $-CH_2C(=NH)-NMe_2$ | Me | 0 |
| 1-130 | H | H | $-CH_2C(=NH)-NMe_2$ | Me | 0 |
| 1-131 | Me | -COOMe | Me | Me | 0 |
| 1-132 | H | -COOMe | Me | Me | 0 |
| 1-133 | Me | $-CH_2OH$ | Me | Me | 0 |
| 1-134 | H | $-CH_2OH$ | Me | Me | 0 |
| 1-135 | Me | $-CH_2F$ | Me | Me | 0 |
| 1-136 | H | $-CH_2F$ | Me | Me | 0 |
| 1-137 | Me | Me | Me | Me | 0 |
| 1-138 | H | Me | Me | Me | 0 |
| 1-139 | Me | -OCar | Me | Me | 0 |
| 1-140 | H | -OCar | Me | Me | 0 |

UNITED STATES PATENT AND TRADEMARK OFFICE
CERTIFICATE OF CORRECTION

PATENT NO. : 5,104,867
DATED : April 14, 1992
INVENTOR(S) : KAWAMOTO et al

It is certified that error appears in the above-identified patent and that said Letters Patent is hereby corrected as shown below:

Table 1 (cont)

| Cpd. No. | $R^1$ | $R^2$ | $R^3$ | $R^4$ | $\ell$ |
|---|---|---|---|---|---|
| 1-141 | Me | -OAc | Me | Me | O |
| 1-142 | H | -OAc | Me | Me | O |
| 1-143 | Me | Ac | Me | Me | O |
| 1-144 | H | Ac | Me | Me | O |
| 1-145 | Me | CN | Me | Me | O |
| 1-146 | H | CN | Me | Me | O |
| 1-147 | Me | $-CH_2NHAc$ | Me | Me | O |
| 1-148 | H | $-CH_2NHAc$ | Me | Me | O |
| 1-149 | Me | $-CH_2OMe$ | Me | Me | O |
| 1-150 | H | $-CH_2OMe$ | Me | Me | O |
| 1-151 | Me | $-CH_2SMe$ | Me | Me | O |
| 1-152 | H | $-CH_2SMe$ | Me | Me | O |
| 1-153 | Me | $-CH_2SOMe$ | Me | Me | O |
| 1-154 | H | $-CH_2SOMe$ | Me | Me | O |
| 1-155 | Me | $-CH_2SO_2Me$ | Me | Me | O |
| 1-156 | H | $-CH_2SO_2Me$ | Me | Me | O |
| 1-157 | Me | $-CH_2OH$ | Et | Me | O |
| 1-158 | H | $-CH_2OH$ | Et | Me | O |
| 1-159 | Me | $-CH_2OH$ | All | Me | O |
| 1-160 | H | $-CH_2OH$ | All | Me | O |
| 1-161 | Me | $-CH_2OH$ | 2-FEt | Me | O |
| 1-162 | H | $-CH_2OH$ | 2-FEt | Me | O |
| 1-163 | Me | $-CH_2OH$ | $-CH_2Car$ | Me | O |
| 1-164 | H | $-CH_2OH$ | $-CH_2Car$ | Me | O |
| 1-165 | Me | $-CH_2OH$ | $-CH_2CN$ | Me | O |
| 1-166 | H | $-CH_2OH$ | $-CH_2CN$ | Me | O |
| 1-167 | Me | H | $-CH_2SO_2NH_2$ | Me | O |
| 1-168 | H | H | $-CH_2SO_2NH_2$ | Me | O |

UNITED STATES PATENT AND TRADEMARK OFFICE
CERTIFICATE OF CORRECTION

PATENT NO. : 5,104,867
DATED : April 14, 1992
INVENTOR(S) : KAWAMOTO et al

Page 10 of 14

It is certified that error appears in the above-identified patent and that said Letters Patent is hereby corrected as shown below:

Table 1 (cont)

| Cpd. No. | $R^1$ | $R^2$ | $R^3$ | $R^4$ | $\ell$ |
|---|---|---|---|---|---|
| 1-169 | Me | H | 2-FEt | 2-FEt | 0 |
| 1-170 | H | H | 2-FEt | 2-FEt | 0 |
| 1-171 | Me | H | $-CH_2$Car | Et | 0 |
| 1-172 | H | H | $-CH_2$Car | Et | 0 |
| 1-173 | Me | H | 3-FPr | Me | 0 |
| 1-174 | H | H | 3-FPr | Me | 0 |
| 1-175 | Me | H | 2-(NHAc)Et | Me | 0 |
| 1-176 | H | H | 2-(NHAc)Et | Me | 0 |
| 1-177 | Me | H | 2-($NH_2$)Et | Me | 0 |
| 1-178 | H | H | 2-($NH_2$)Et | Me | 0 |
| 1-179 | Me | H | 2-(NH=CMe-NH-)Et | Me | 0 |
| 1-180 | H | H | 2-(NH=CMe-NH-)Et | Me | 0 |
| 1-181 | Me | H | 2-CℓEt | Me | 0 |
| 1-182 | H | H | 2-CℓEt | Me | 0 |
| 1-183 | Me | H | 2-CarEt | Me | 0 |
| 1-184 | H | H | 2-CarEt | Me | 0 |
| 1-185 | Me | 1-Pyrd-CO- | Me | Me | 0 |
| 1-186 | H | 1-Pyrd-CO- | Me | Me | 0 |
| 1-187 | Me | 1-Pip-CO- | Me | Me | 0 |
| 1-188 | H | 1-Pip-CO- | Me | Me | 0 |
| 1-189 | Me | Mor-CO- | Me | Me | 0 |
| 1-190 | H | Mor-CO- | Me | Me | 0 |
| 1-191 | Me | Thz-CO- | Me | Me | 0 |
| 1-192 | H | Thz-CO- | Me | Me | 0 |

UNITED STATES PATENT AND TRADEMARK OFFICE
CERTIFICATE OF CORRECTION

PATENT NO. : 5,104,867

DATED : April 14, 1992

INVENTOR(S) : KAWAMOTO et al

It is certified that error appears in the above-identified patent and that said Letters Patent is hereby corrected as shown below:

Table 1 (cont)

| Cpd. No. | $R^1$ | $R^2$ | $R^3$ | $R^4$ | $\ell$ |
|---|---|---|---|---|---|
| 1-193 | Me | (2-MeOEt)Car | Me | Me | 0 |
| 1-194 | H | (2-MeOEt)Car | Me | Me | 0 |
| 1-195 | Me | H | 3-FPr | Me | 0 |
| 1-196 | H | H | 3-FPr | Me | 0 |
| 1-197 | Me | $-CH_2NO_2$ | Me | Me | 0 |
| 1-198 | H | $-CH_2NO_2$ | Me | Me | 0 |
| 1-199 | Me | H | Et | Et | 0 |
| 1-200 | H | H | Et | Et | 0 |
| 1-201 | Me | H | $-CH_2Car$ | Et | 0 |
| 1-202 | H | H | $-CH_2Car$ | Et | 0 |
| 1-203 | Me | $-CH_2Car$ | Me | Me | 0 |
| 1-204 | H | $-CH_2Car$ | Me | Me | 0 |
| 1-205 | Me | H | 2-($NH_2$-CMe=N-)Et | Me | 0 |
| 1-206 | H | H | 2-($NH_2$-CMe=N-)Et | Me | 0 |
| 1-207 | Me | H | 2-(MeC-N-)Et<br>     ‖  \|<br>    HN Me | Me | 0 |
| 1-208 | H | H | 2-(MeC-N-)Et<br>     ‖  \|<br>    HN Me | Me | 0 |
| 1-209 | Me | H | $-CH_2CF_3$ | Me | 0 |
| 1-210 | H | H | $-CH_2CF_3$ | Me | 0 |
| 1-211 | Me | 1-Piz-CO- | Me | Me | 0 |
| 1-212 | H | 1-Piz-CO- | Me | Me | 0 |
| 1-213 | Me | 4-Ac-1-Piz-CO- | Me | Me | 0 |
| 1-214 | H | 4-Ac-1-Piz-CO- | Me | Me | 0 |
| 1-215 | Me | 4-Me-1-Piz-CO- | Me | Me | 0 |
| 1-216 | H | 4-Me-1-Piz-CO- | Me | Me | 0 |
| 1-217 | Me | CHO- | Me | Me | 0 |

UNITED STATES PATENT AND TRADEMARK OFFICE
CERTIFICATE OF CORRECTION

PATENT NO. : 5,104,867
DATED : April 14, 1992
INVENTOR(S) : KAWAMOTO et al

It is certified that error appears in the above-identified patent and that said Letters Patent is hereby corrected as shown below:

Table 1 (cont)

| Cpd. No. | $R^1$ | $R^2$ | $R^3$ | $R^4$ | $\underline{\mathit{l}}$ |
|---|---|---|---|---|---|
| 1-218 | H | CHO- | Me | Me | 0 |
| 1-219 | Me | Etc | Me | Me | 0 |
| 1-220 | H | Etc | Me | Me | 0 |
| 1-221 | Me | 1-Azt-CO- | Me | Me | 0 |
| 1-222 | H | 1-Azt-CO- | Me | Me | 0 |
| 1-223 | Me | 1-Azr-CO- | Me | Me | 0 |
| 1-224 | H | 1-Azr-CO- | Me | Me | 0 |
| 1-225 | Me | $-CH_2CN$ | Me | Me | 0 |
| 1-226 | H | $-CH_2CN$ | Me | Me | 0 |
| 1-227 | Me | $-CH_2F$ | Me | Me | 0 |
| 1-228 | H | $-CH_2F$ | Me | Me | 0 |
| 1-229 | Me | $-CH_2NMe_2$ | Me | Me | 0 |
| 1-230 | H | $-CH_2NMe_2$ | Me | Me | 0 |
| 1-231 | Me | $-CH_2NHSO_2Me$ | Me | Me | 0 |
| 1-232 | H | $-CH_2NHSO_2Me$ | Me | Me | 0 |
| 1-233 | Me | $-CH_2SO_2NH_2$ | Me | Me | 0 |
| 1-234 | H | $-CH_2SO_2NH_2$ | Me | Me | 0 |
| 1-235 | Me | $-CH_2C(=NH)-NMe_2$ | Me | Me | 0 |
| 1-236 | H | $-CH_2C(=NH)-NMe_2$ | Me | Me | 0 |
| 1-237 | Me | $-CH_2N=CHNH_2$ | Me | Me | 0 |
| 1-238 | H | $-CH_2N=CHNH_2$ | Me | Me | 0 |
| 1-239 | Me | $-CH_2NMe-CH=NH$ | Me | Me | 0 |
| 1-240 | H | $-CH_2NMe-CH=NH$ | Me | Me | 0 |
| 1-241 | Me | $-CH_2N=CHMe-NH_2$ | Me | Me | 0 |
| 1-242 | H | $-CH_2N=CHMe-NH_2$ | Me | Me | 0 |

UNITED STATES PATENT AND TRADEMARK OFFICE
CERTIFICATE OF CORRECTION

PATENT NO. : 5,104,867
DATED : April 14, 1992
INVENTOR(S) : KAWAMOTO et al

It is certified that error appears in the above-identified patent and that said Letters Patent is hereby corrected as shown below:

Table 1 (cont)

| Cpd. No. | $R^1$ | $R^2$ | $R^3$ | $R^4$ | $\underline{\ell}$ |
|---|---|---|---|---|---|
| 1-243 | Me | -CH$_2$NMe-CMe=NH | Me | Me | o |
| 1-244 | H | -CH$_2$NMe-CMe=NH | Me | Me | o |
| 1-245 | Me | H | 2-MeSEt | Me | o |
| 1-246 | H | H | 2-MeSEt | Me | o |
| 1-247 | Me | H | 2-MeOEt | Me | o |
| 1-248 | H | H | 2-MeOEt | Me | o |
| 1-249 | Me | Car | Et | Et | o |
| 1-250 | H | Car | Et | Et | o |
| 1-251 | Me | 3-HO-1-Pyrd-CO- | Me | Me | o |
| 1-252 | H | 3-HO-1-Pyrd-CO- | Me | Me | o |
| 1-253 | Me | 3-Me-1-Pyrd-CO- | Me | Me | o |
| 1-254 | H | 3-Me-1-Pyrd-CO- | Me | Me | o |
| 1-255 | Me | 2-oxo-1-Pyrd-CO- | Me | Me | o |
| 1-256 | H | 2-oxo-1-Pyrd-CO- | Me | Me | o |
| 1-257 | Me | 3-F-1-Pyrd-CO- | Me | Me | o |
| 1-258 | H | 3-F-1-Pyrd-CO- | Me | Me | o |
| 1-259 | Me | 2-Car-1-Pyrd-CO- | Me | Me | o |
| 1-260 | H | 2-Car-1-Pyrd-CO- | Me | Me | o |
| 1-261 | Me | 3-MeO-1-Pyrd-CO- | Me | Me | o |
| 1-262 | H | 3-MeO-1-Pyrd-CO- | Me | Me | o |
| 1-263 | Me | 3-oxo-1-Pyrd-CO- | Me | Me | o |
| 1-264 | H | 3-oxo-1-Pyrd-CO- | Me | Me | o |
| 1-265 | Me | 3-NC-1-Pyrd-CO- | Me | Me | o |
| 1-266 | H | 3-NC-1-Pyrd-CO- | Me | Me | o |
| 1-267 | Me | EtCar | Me | Me | o |
| 1-268 | H | EtCar | Me | Me | o |
| 1-269 | Me | EtCar | Et | Me | o |
| 1-270 | H | EtCar | Et | Me | o |

UNITED STATES PATENT AND TRADEMARK OFFICE
CERTIFICATE OF CORRECTION

PATENT NO. : 5,104,867
DATED : April 14, 1992
INVENTOR(S) : KAWAMOTO et al

It is certified that error appears in the above-identified patent and that said Letters Patent is hereby corrected as shown below:

Table 1 (cont)

| Cpd. No. | $R^1$ | $R^2$ | $R^3$ | $R^4$ | $\ell$ |
|---|---|---|---|---|---|
| 1-271 | Me | iPrCar | Me | Me | O |
| 1-272 | H | iPrCar | Me | Me | O |
| 1-273 | Me | iPrCar | Et | Me | O |
| 1-274 | H | iPrCar | Et | Me | O |
| 1-275 | Me | cPrCar | Me | Me | O |
| 1-276 | H | cPrCar | Me | Me | O |
| 1-277 | Me | cPrCar | Et | Me | O |
| 1-278 | H | cPrCar | Et | Me | O |

--.

Signed and Sealed this

Sixteenth Day of August, 1994

Attest:

BRUCE LEHMAN

Attesting Officer    Commissioner of Patents and Trademarks

UNITED STATES PATENT AND TRADEMARK OFFICE
CERTIFICATE OF CORRECTION

PATENT NO. : 5,104,867

DATED : April 14, 1992

INVENTOR(S) : KAWAMOTO et al

Page 1 of 3

It is certified that error appears in the above-indentified patent and that said Letters Patent is hereby corrected as shown below:

Column 87, line 38 (claim 3), change "The composition of" to read --The compound of--.

Column 89, lines 1-2 (claim 11), change "selected from the group consisting of" to read --wherein the compound is--.

Column 89, lines 5-6 (claim 12), change "selected from the group consisting of" to read --wherein the compound is--.

Column 89, lines 9-10 (claim 13), change "selected from the group consisting of" to read --wherein the compound is--.

Column 89, lines 14-15 (claim 14), change "selected from the group consisting of" to read --wherein the compound is--.

Column 89, lines 19-20 (claim 15), change "selected from the group consisting of" to read --wherein the compound is--.

Column 89, lines 23-24 (claim 16), change "selected from the group consisting of" to read --wherein the compound is--.

UNITED STATES PATENT AND TRADEMARK OFFICE
CERTIFICATE OF CORRECTION

PATENT NO. : 5,104,867
DATED : April 14, 1992
INVENTOR(S) : KAWAMOTO et al

It is certified that error appears in the above-indentified patent and that said Letters Patent is hereby corrected as shown below:

Column 90, line 52 (claim 21), after ";", insert --and--.

Column 90, line 64 (claim 22), after ";", insert --and--.

Column 92, line 38 (claim 27), after ";", insert --and--.

Column 92, line 50 (claim 28), after ";", insert --and--.

Column 92, line 23 (claim 25), change "The composition of" to read --The method of--.

Column 92, line 26 (claim 26), change "The composition of" to read --The method of--.

Column 92, line 37 (claim 27), after ";", insert --and--.

Column 92, line 50 (claim 28), after ";", insert --and--.

Column 92, after claim 28, insert

--Claim 29. The method of claim 23, wherein the antibiotic is administered orally.

--Claim 30. The method of claim 23, wherein the antibiotic is administered parenterally.--

UNITED STATES PATENT AND TRADEMARK OFFICE
CERTIFICATE OF CORRECTION

PATENT NO. : 5,104,867
DATED : April 14, 1992
INVENTOR(S) : KAWAMOTO et al

It is certified that error appears in the above-indentified patent and that said Letters Patent is hereby corrected as shown below:

Title page, right column, below Abstract, change
"28 Claims" to read --30 Claims--.

Signed and Sealed this

Fifteenth Day of August, 1995

Attest:

BRUCE LEHMAN

*Attesting Officer*  *Commissioner of Patents and Trademarks*

UNITED STATES PATENT AND TRADEMARK OFFICE
CERTIFICATE OF CORRECTION

PATENT NO. : 5,104,867
DATED : April 14, 1992
INVENTOR(S) : KAWAMOTO et al

Page 1 of 2 Pages

It is certified that error appears in the above-indentified patent and that said Letters Patent is hereby corrected as shown below:

Column 90, (Claim 21), lines 47-48: replace
"(1-hydroxymethyl)" with --(1-hydroxyethyl)--;
                   line 51: replace
"(1-hydroxymethyl)" with --(1-hydroxyethyl)--;
                   line 54: replace
"(1-hydroxymethyl)" with --(1-hydroxyethyl)--.

Column 90, (Claim 22), line 59: replace
"-1-hydroxymethyl)" with -- -1-hydroxyethyl)--;
                   lines 62-63: replace
"-1-hydroxymethyl)" with -- -1-hydroxyethyl)--;
                   lines 66-67: replace
"-1-hydroxymethyl)" with -- -1-hydroxyethyl)--;

Column 92, (Claim 27), lines 33-34: replace
"(1-hydroxymethyl)" with --(1-hydroxyethyl)--;
                   line 37: replace
"(1-hydroxymethyl)" with --(1-hydroxyethyl)--;
                   line 40: replace
"(1-hydroxymethyl)" with --(1-hydroxyethyl)--.

UNITED STATES PATENT AND TRADEMARK OFFICE
CERTIFICATE OF CORRECTION

PATENT NO.  : 5,104,867
DATED       : April 14, 1992
INVENTOR(S) : KAWAMOTO et al It is certified that error appears in the above-indentified patent and that said Letters Patent is hereby corrected as shown below:

```
Column 92, (Claim 28), line 42:   replace
"composition" with --method--;
                         line 45:   replace
"-1-hydroxymethyl)" with -- -1-hydroxyethyl)--;
                         lines 48-49:   replace
"-1-hydroxymethyl)" with -- -1-hydroxyethyl)--;
                         lines 52-53:   replace
"-1-hydroxymethyl)" with -- -1-hydroxyethyl)--.
```

Signed and Sealed this

Nineteenth Day of November, 1996

*Attest:*

BRUCE LEHMAN

*Attesting Officer*    *Commissioner of Patents and Trademarks*